(12) United States Patent
Poznansky et al.

(10) Patent No.: US 11,364,264 B2
(45) Date of Patent: Jun. 21, 2022

(54) EX VIVO ANTIGEN-PRESENTING CELLS OR ACTIVATED CD-POSITIVE T CELLS FOR TREATMENT OF CANCER

(71) Applicant: The General Hospital Corporation, Boston, MA (US)

(72) Inventors: Mark C. Poznansky, Newton Center, MA (US); Jeffrey A. Gelfand, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 463 days.

(21) Appl. No.: 16/331,846

(22) PCT Filed: Sep. 8, 2017

(86) PCT No.: PCT/US2017/050625
§ 371 (c)(1),
(2) Date: Mar. 8, 2019

(87) PCT Pub. No.: WO2018/049120
PCT Pub. Date: Mar. 15, 2018

(65) Prior Publication Data
US 2019/0374575 A1    Dec. 12, 2019

Related U.S. Application Data

(60) Provisional application No. 62/385,880, filed on Sep. 9, 2016, provisional application No. 62/385,898, filed on Sep. 9, 2016.

(51) Int. Cl.
*A61K 35/15* (2015.01)
*A61P 35/00* (2006.01)
*A61K 39/00* (2006.01)
*A61K 45/06* (2006.01)
*C07K 14/47* (2006.01)
*C07K 16/30* (2006.01)
*C12N 5/0784* (2010.01)

(52) U.S. Cl.
CPC ...... *A61K 35/15* (2013.01); *A61K 39/001168* (2018.08); *A61K 45/06* (2013.01); *A61P 35/00* (2018.01); *C07K 14/47* (2013.01); *C07K 16/3069* (2013.01); *C12N 5/0639* (2013.01); *A61K 2039/6043* (2013.01); *A61K 2039/892* (2018.08); *C07K 2319/30* (2013.01); *C12N 2501/07* (2013.01); *C12N 2501/998* (2013.01); *C12N 2502/1121* (2013.01); *C12N 2502/30* (2013.01)

(58) Field of Classification Search
None
See application file for complete search history.

(56) References Cited

U.S. PATENT DOCUMENTS

| | | | |
|---|---|---|---|
| 5,075,109 | A | 12/1991 | Tice et al. |
| 5,514,555 | A | 5/1996 | Springer et al. |
| 5,583,131 | A | 12/1996 | Bridger et al. |
| 5,994,126 | A | 11/1999 | Steinman et al. |
| 6,448,054 | B1 | 9/2002 | Poznansky et al. |
| 7,935,692 | B2 | 5/2011 | Bridger et al. |
| 7,943,133 | B2 | 5/2011 | Gelfand |
| 8,143,387 | B2 | 3/2012 | Gelfand |
| 2004/0161413 | A1 | 8/2004 | Laus et al. |
| 2006/0211112 | A1 | 9/2006 | Harris et al. |
| 2008/0112962 | A1 | 5/2008 | Palucka et al. |
| 2008/0300165 | A1 | 12/2008 | Poznansky et al. |
| 2010/0255539 | A1 | 10/2010 | Gelfand |
| 2011/0129484 | A1 | 6/2011 | Gelfand et al. |
| 2014/0219952 | A1 | 8/2014 | Cameron |

FOREIGN PATENT DOCUMENTS

| | | |
|---|---|---|
| WO | WO 2003/022885 | 3/2003 |
| WO | WO 2016/081554 | 5/2016 |
| WO | WO 2017/156461 | 9/2017 |

OTHER PUBLICATIONS

Dhodapkar et al., 2002,. J. Exp. Med. vol. 195: 125-133.*
MacAry et al., 2004, Immunity vol. 20: 95-106.*
Kabashima et al., 2007, Biochem. Biophy. Res. Comm. vol. 361: 1012-1016.*
Bayry et al., 2008, PNAS<vol. 105: 10221-10226.*
U.S. Appl. No. 62/306,168, Poznansky et al., filed Mar. 10, 2016.
Bergan et al., "Development and in vitro validation of anti-mesothelin biobodies that prevent CA125/Mesothelin-dependent cell attachment," Cancer Letters, Oct. 8, 2007, 255(2):263-74.
Debnath et al., "Small molecule inhibitors of CXCR4." Theranostics, Jan. 15, 2013 3;1:47-75 pages.
Hodge, et al. "Enhanced activation of T cells by dendritic cells engineered to hyperexpress a triad of costimulatory molecules," Journal of the National Cancer Institute, Aug. 29, 2000, 92(15):1228-39.

(Continued)

*Primary Examiner* — Amy E Juedes
(74) *Attorney, Agent, or Firm* — Fish & Richardson P.C.

(57) ABSTRACT

This disclosure is directed to methods of preparing dendritic cells or other CD40 bearing antigen-presenting cells and methods of treating cancer by using the dendritic cells or other antigen-presenting cells in combination with anti-chemorepellant agents. This disclosure is further directed to methods of preparing T cells and methods of treating cancer, by activated T cells optionally in combination with anti-chemorepellant agents. The antigen presenting cells of the disclosure are activated by incubation with cancer cells and fusion proteins. The T cells of the disclosures are activated by incubation with activated antigen-presenting cells that were activated by incubation with cancer cells and a fusion protein. In particular, the fusion protein comprises an antigen-binding domain, e.g., an antibody or antibody fragment, and a stress protein domain.

14 Claims, 22 Drawing Sheets

Specification includes a Sequence Listing.

(56) References Cited

OTHER PUBLICATIONS

Kämpgen et al., "Class II major histocompatibility complex molecules of murine dendritic cells: synthesis, sialylation of invariant chain, and antigen processing capacity are down-regulated upon culture," Proceedings of the National Academy of Sciences, Apr. 15, 1991, 88(8):3014-8.

PCT International Report on Patentability in International Appln. No. PCT/US2017/050625, dated Mar. 12, 2019, 10 pages.

PCT International Search Report and Written Opinion in International Appln. No. PCT/US2017/050625, dated Jan. 9, 2018, 14 pages.

Santambrogio et al., "Extracellular antigen processing and presentation by immature dendritic cells," Proceedings of the National Academy of Sciences, Dec. 21, 1999, 96(26):15056-61.

Santini et al., "A controlled-release microchip," Nature, Jan. 1999, 397(6717):335-8.

Yuan et al., "A novel mycobacterial Hsp70-containing fusion protein targeting mesothelin augments antitumor immunity and prolongs survival in murine models of ovarian cancer and mesothelioma," Journal of hematology & oncology, Dec. 1, 2014, 7(1):15.

Zeng et al., "Improved antitumoral efficacy of mesothelin targeted immune activating fusion protein in Murine model of ovarian cancer," International Journal of Cancer and Clinical Research, Apr. 2016, 3:051, 4 pages.

Zweerink et al., "Presentation of endogenous peptides to MHC class I-restricted cytotoxic T lymphocytes in transport deletion mutant T2 cells," The Journal of Immunology, Mar. 1, 1993, 150(5):1763-71.

\* cited by examiner

VIC-007

*GSS*QVQLQQSGPGLVTPSQTLSLTCAISGDSVSSNSATWNWIRQSPSRGLE
WLGRTYYRSKWYNDYAVSVKSRMSINPDTSKNQFSLQLNSVTPEDTAVYYC
ARGMMTYYYGMDVWGQGTTVTVSSGILGSGGGGSGGGGSGGGGSQPVLTQS
SSLSASPGASASLTCTLRSGINVGPYRIYWYQQKPGSPPQYLLNYKSDSDK
QQGSGVPSRFSGSKDASANAGVLLISGLRSEDEADYYCMIWHSSAAVFGGG
TQLTVL*SGILEQQG*GGGGSGGGGSGGGGS*AAAMRS*MARAVGIDLGTTNSVV
SVLEGGDPVVVANSEGSRTTPSIVAFARNGEVLVGQPAKNQAVTNVDRTVR
SVKRHMGSDWSIEIDGKKYTAPEISARILMKLKRDAEAYLGEDITDAVITT
PAYFNDAQRQATKDAGQIAGLNVLRIVNEPTAAALAYGLDKGEKEQRILVF
DLGGGTFDVSLLEIGEGVVEVRATSGDNHLGGDDWDQRVVDWLVDKFKGTS
GIDLTKDKMAMQRLREAAEKAKIELSSSQSTSINLPYITVDADKNPLFLDE
QLTRAEFQRITQDLLDRTRKPFQSVIADTGISVSEIDHVVLGGSTRMPAV
TDLVKELTGGKEPNKGVNPDEVVAVGAALQAGVLKGEVKDVLLLDVTPLSL
GIETKGGVMTRLIERNTTIPTKRSETFTTADDNQPSVQIQVYQGEREIAAH
NKLLGSFELTGIPPAPRGIPQIEVTFDIDANGIVHVTAKDKGTGKENTIRI
QEGSGLSKEDIDRMIKDAEAHAEEDRKRREEADVRNQAETLVYQTEKFVKE
QREAEGGSKVPEDTLNKVDAAVAEAKAALGGSDISAIKSAMEKLGQESQAL
GQAIYEAAQAASQATGAAHPGGEPGGAHPGSADDVVDAEVVDDGREAK

VIC-008

QVQLQQSGPGLVTPSQTLSLTCAISGDSVSSNSATWNWIRQSPSRGLEWLG
RTYYRSKWYNDYAVSVKSRMSINPDTSKNQFSLQLNSVTPEDTAVYYCARG
MMTYYYGMDVWGQGTTVTVSSGILGSGGGGSGGGGSGGGGSQPVLTQSSSL
SASPGASASLTCTLRSGINVGPYRIYWYQQKPGSPPQYLLNYKSDSDKQQG
SGVPSRFSGSKDASANAGVLLISGLRSEDEADYYCMIWHSSAAVFGGGTQL
TVLGGGGSGGGGSGGGGSMARAVGIDLGTTNSVVSVLEGGDPVVVANSEGS
RTTPSIVAFARNGEVLVGQPAKNQAVTNVDRTVRSVKRHMGSDWSIEIDGK
KYTAPEISARILMKLKRDAEAYLGEDITDAVITTPAYFNDAQRQATKDAGQ
IAGLNVLRIVNEPTAAALAYGLDKGEKEQRILVFDLGGGTFDVSLLEIGEG
VVEVRATSGDNHLGGDDWDQRVVDWLVDKFKGTSGIDLTKDKMAMQRLREA
AEKAKIELSSSQSTSINLPYITVDADKNPLFLDEQLTRAEFQRITQDLLDR
TRKPFQSVIADTGISVSEIDHVVLGGSTRMPAVTDLVKELTGGKEPNKGV
NPDEVVAVGAALQAGVLKGEVKDVLLLDVTPLSLGIETKGGFMTRLIERNT
TIPTKRSETFTTADDNQPSVQIQVYQGEREIAAHNKLLGSFELTGIPPAPR
GIPQIEVTFDIDANGIVHVTAKDKGTGKENTIRIQEGSGLSKEDIDRMIKD
AEAHAEEDRKRREEADVRNQAETLVYQTEKFVKEQREAEGGSKVPEDTLNK
VDAAVAEAKAALGGSDISAIKSAMEKLGQESQALGQAIYEAAQAASQATGA
AHPGGEPGGAHPGSADDVVDAEVVDDGREAK

*FIG. 1*

EX VIVO ANTIGEN-PRESENTING CELLS OR ACTIVATED CD-POSITIVE T CELLS FOR TREATMENT OF CANCER

STATEMENT OF PRIORITY

This application is a 35 U.S.C. § 371 atonal phase application of PCT Application PCT/US2017/050625 filed Sep. 8, 2017, which claims the benefit of U.S. Provisional Application Ser. No. 62/385,880, filed Sep. 9, 2016 and U.S. Provisional Application Ser. No. 62/385,898, filed Sep. 9, 2016, the entire contents of each of which are incorporated by reference herein in its entirety.

STATEMENT OF GOVERNMENT SUPPORT

This invention was made with government support. The U.S. Government has certain rights in this invention.

STATEMENT REGARDING ELECTRONIC FILING OF A SEQUENCE LISTING

A Sequence Listing, in ASCII text format, submitted under 37 C.F.R. § 1.821, entitled 1417-17_ST25.txt, 16,074 bytes in size, generated on Mar. 7, 2019 and filed via EFS-Web, is provided in lieu of a paper copy. This Sequence Listing is hereby incorporated by reference into the specification for its disclosures.

FIELD OF THE INVENTION

This disclosure is directed to methods of preparing dendritic cells or other CD40 bearing antigen-presenting cells and methods of treating cancer by using the dendritic cells or other antigen-presenting cells in combination with anti-chemorepellant agents. This disclosure is further directed to methods of preparing T cells and methods of treating cancer by using activated T cells optionally in combination with anti-chemorepellant agents. The antigen presenting cells of the disclosure are activated by incubation with cancer cells and fusion proteins. The T cells of the disclosures are activated by incubation with activated antigen-presenting cells that were activated by incubation with cancer cells and a fusion protein. In particular, the fusion protein comprises an antigen-binding domain, e.g., an antibody or antibody fragment, and a stress protein domain.

BACKGROUND OF THE INVENTION

Conventional treatments for cancers, e.g., surgery, radiation, and chemotherapy, are often accompanied by substantial side effects, cancer relapses, and physical suffering. For example, chemotherapies, which are intended to kill aggressively dividing cancer cells, may also nonspecifically target normal cells that are rapidly proliferating, e.g., the cells in blood, intestinal tract, and hair. This leads to severe side effects, e.g., anemia, diarrhea, fatigue, and hair loss.

Immunotherapy is a promising treatment for cancers as well as other diseases. The immunotherapy treats disease by inducing, enhancing, augmenting, or suppressing an immune response in a patient. Using immunotherapy, the immune system can be stimulated to recognize cancer cells, thereby creating long-lasting therapeutic effects against cancer recurrence or relapse. Moreover, by focusing on enhancing the immune system rather than targeting proliferating cells, immunotherapies are more specific and cause fewer side effects compared to conventional cancer treatments.

Therefore, there is a need for a more effective immunotherapy to promote an immune response against cancer.

SUMMARY OF THE INVENTION

Immunotherapy is becoming an increasingly important tool in the armamentarium against cancers. However, efficacy of immunotherapy has not been robust as was hoped, due in part to reduced antigenicity of the antigens and the subsequently weakened immunological response. One potential solution is to increase a patient's own immune response to disease-associated antigens by contacting T cells with antigen-presenting cells that express tumor-specific immunogenic antigens on the cell surface. Either the antigen-presenting cells or the resulting activated T cells may be administered to the patient.

Stress proteins are very efficient at activating antigen-presenting cells to provoke a T cell response. They have been particularly effective at eliciting cell mediated immune and humoral immune responses by this pathway.

In one aspect, the present invention is directed to a method for preparing activated antigen-presenting cells ("APCs") by incubating immune cells ex vivo in the presence of tumor cells (or other tumor-specific antigen(s)) and a fusion protein for a time period sufficient to produce the activated APCs.

In another aspect, the present invention is directed to a method for preparing tumor-specific T cells via activated APCs by incubating immune cells ex vivo in the presence of tumor cells (or other tumor-specific antigen(s)) and a fusion protein for a time period sufficient to produce the activated APCs, optionally isolating the APCs from the tumor cells/antigens and fusion protein, then incubating the T cells and activated APCs for a time period sufficient to produce activated, tumor-specific T cells, particularly CD3-positive T cells.

The fusion protein binds to antigens with high affinity, is highly immunogenic, exhibits MHC class I priming, provokes a T cell response, and is able to be produced in non-mammalian systems such as $E.\ coli$. The fusion protein is thus suitable for use as a highly immunogenic vaccine for the prevention or treatment of infectious, inflammatory, autoimmune, or malignant disease. The fusion protein may also act as a potential candidate presented to APCs to ultimately provoke T cell responses and increase the specificity of immunotherapy against tumors. Non-limiting examples of fusion proteins can be found in U.S. Pat. Nos. 8,143,387 and 7,943,133; U.S. Patent Pub. No. 20110129484; and PCT Application Number PCT/US2017/021911; each of which is incorporated herein by reference in its entirety.

Some tumor cells secrete concentrations of chemokines that are sufficient to repel immune cells from the site of a tumor, thus creating a "chemorepellant wall" or "fugetactic wall" around the tumor. The chemorepellant wall reduces the immune system's ability to target and eradicate the tumor. For example, repulsion of tumor antigen-specific T cells, e.g., from a tumor expressing high levels of CXCL12 or interleukin 8 (IL-8), allows the tumor cells to evade immune control. Anti-chemorepellant agents may inhibit the chemorepellant activity of tumor cells and allow the patient's immune system to target the tumor. Anti-chemorepellant agents and the systemic delivery of anti-chemorepellant agents are known in the art (see, for example, U.S. Patent Application Publication No. 2008/0300165, incorporated herein by reference in its entirety).

Without being bound by theory, it is believed that the antigen-binding domain of the fusion protein will bind to the target (e.g., cancer cells or tumor), and the stress protein domain will induce maturation of antigen-presenting cells (e.g., dendritic cells). In combination, the anti-chemorepellant agent will inhibit the chemorepellant activity of the cancer cells with regard to the antigen-presenting cells and/or T cells, such that the immune cells are able to penetrate the "chemorepellant wall" and access the target. In some embodiments, the combination results in additive or synergistic effects.

In one aspect, this invention relates to methods of preparing activated APCs, which comprises incubating immune cells ex vivo in the presence of cancer or tumor cells and a fusion protein for a time period sufficient to produce the activated APCs, wherein at least one activated APC displays an antigen derived from the cancer or tumor cells. In one embodiment, the method further comprises isolating the activated APCs, wherein the isolated activated APCs are free or substantially free of the cancer or tumor cells and/or the fusion protein.

In one aspect, this invention relates to methods of preparing activated T cells, which comprises incubating T cells with activated APCs for a period of time sufficient to produce activated T cells, wherein the APCs were prepared by incubating immune cells ex vivo in the presence of cancer or tumor cells and a fusion protein for a time period sufficient to produce the activated APCs, wherein at least one activated APC displays an antigen derived from the cancer or tumor cells. In one embodiment, the method further comprises isolating the activated T cells. In one embodiment, the isolated activated T cells are free or substantially free of the activated APCs, cancer or tumor cells and/or the fusion protein. In one embodiment, the APCs comprise dendritic cells.

In one aspect, the fusion protein comprises an antigen-binding component and a heat shock protein component. While the antigen-binding component binds to the tumor cells, the heat shock protein component activates the APCs. In one embodiment, the antigen-binding component of the fusion protein may be any antibody or other molecule that recognizes a tumor or cancer cell of interest. In one embodiment, the antigen-binding component is a single chain antibody, a variable domain, or a fragment antigen-binding ("Fab") domain of an antibody.

In one aspect, the tumor cells are obtained from a patient.

In one aspect, the antigen-binding binding component is specific for a cancer antigen (e.g., a tumor-specific antigen or a tumor-associated antigen). The cancer antigen may be any identifiable cell surface antigen that is expressed by a cancer of interest. In one embodiment, the cancer antigen is mesothelin, alphafetoprotein, CEA, CA-125, MUC-1, Her2Neu, ETA, NY-ESO-1, VEGF, VEGFR1, VEGFR2, PSMA, prostate specific antigen, HPV17E7, mutant p53, surviving, ras, MAGE, gp100, tyrosinase, WT1, PR1, folate-binding protein, CA-19-9, FAP, G250, or A33. In one embodiment, the antibody is specific for mesothelin. Fusion proteins that recognize and bind to mesothelin are described, for example, in U.S. Pat. No. 7,943,133, which is incorporated herein by reference in its entirety. Additional fusion proteins are described in PCT Application No. PCT/US2017/021911, which is incorporated herein by reference in its entirety.

In one embodiment, the antigen-presenting cells include, but are not limited to, dendritic cells, B lymphocytes, and mononuclear phagocytes. The mononuclear phagocytes may include monocytes and/or macrophages. In some aspects, the APCs comprise at least one CD40. In another aspect, the APCs are dendritic cells.

In one embodiment, the heat shock protein component includes but is not limited to HSP70 and/or an immune activating fragment and/or modified sequence thereof. In another aspect, the HSP70 or the immune activating fragment and/or modified sequence thereof is from *Mycobacterium tuberculosis*.

In one embodiment, the method of preparing the APCs further comprises expanding the immune cells in the presence of a growth factor. In one embodiment, the method of preparing the APCs further comprises expanding the activated APCs in the presence of a growth factor. In one aspect, the growth factor is a cytokine. In another aspect, the growth factor includes, but is not limited to, Flt-3 ligand, GM-CSF, IL-4, M-CSF, IFNα, IL-1β, IL-4, IL-6, IL-13, IL-15, TNFα, or any combination thereof.

The APCs (e.g., dendritic cells) may be used to treat any cancers. More preferably, the cancer exhibits a chemorepellant effect. Therefore, the method of preparing the APCs may further comprise contacting the isolated antigen-presenting dendritic cells with an effective amount of an anti-chemorepellant agent. Anti-chemorepellant agents may include, without limitation, molecules that inhibit expression of CXCL12 or CXCR4 or CXCR7 (e.g., antisense or siRNA molecules), molecules that bind to CXCL12 or CXCR4 or CXCR7 and inhibit their function (e.g., antibodies or aptamers), molecules that inhibit dimerization of CXCL12 or CXCR4 or CXCR7, and antagonists of CXCR4 or CXCR7. In one embodiment, the inhibitor of CXCL12 signaling is a CXCR4 antagonist. In one aspect, the anti-chemorepellant agents include but are not limited to AMD3100 or a derivative thereof, AMD11070 (also called AMD070), AMD12118, AMD11814, AMD13073, FAMD3465, C131, BKT140, CTCE-9908, KRH-2731, TC14012, KRH-3955, BMS-936564/MDX-1338, LY2510924, GSK812397, KRH-1636, T-20, T-22, T-140, TE-14011, T-14012, TN14003, TAK-779, AK602, SCH-351125, tannic acid, NSC 651016, thalidomide, GF 109230X, an antibody that interferes with dimerization of a chemorepellant chemokine, such as CXCL12, an antibody that interferes with dimerization of a receptor for a chemorepellant chemokine, such as CXCR4 or CXCR7, or a combination thereof. In another aspect, the anti-chemorepellant agent is AMD3100. AMD3100 is described in U.S. Pat. No. 5,583,131, which is incorporated by reference herein in its entirety. In one embodiment, the anti-chemorepellant agent is a CXCR7 antagonist. The CXCR7 antagonist can be but is not limited to CCX771, CCX754, or an antibody that interferes with the dimerization of CXCR7. In certain embodiments, the anti-chemorepellant agent is not an antibody. In certain embodiments, the anti-chemorepellant agent is not a heparinoid. In certain embodiments, the anti-chemorepellant agent is not a peptide. In one embodiment, the amount of anti-chemorepellant agent is sufficient to bind to at least a subset of receptors, e.g., CXCR4 and/or CXCR7, on the surface of the T cells.

In one embodiment, the APCs are allogeneic, autologous, or derived from a cell line. In another embodiment, the APCs are collected from a patient having a tumor. In one aspect, either the APCs or the tumor cells are immobilized on a solid support. The solid support includes but is not limited to a surface of a column, a sepharose bead, a gel, a matrix, a magnetic bead, a plastic surface, or any combination thereof.

In another embodiment, the dendritic cells are differentiated or matured from dendritic cell precursors. The dendritic cell precursors may be activated, or not be activated. In another aspect, the dendritic cell precursors are free or substantially free of neutrophils, macrophages, lymphocytes, or a combination thereof. In one aspect, the dendritic cell precursors are differentiated in the presence of a growth factor. The growth factor may be a cytokine. In another aspect, the growth factor is selected from a group consisting of Flt-3 ligand, GM-CSF, IL-4, M-CSF, IFNα, IL-1β, IL-4, IL-6, IL-13, IL-15 and TNFα.

Another aspect of the invention relates to a method for treating a cancer, e.g., a tumor, in a patient, which comprises administering an effective amount of ex vivo prepared APCs to the patient, wherein the APCs are prepared by incubating immune cells with cancer cells and a fusion protein, wherein the fusion protein comprises a target or antigen binding component and a heat shock protein component. In particular, the target or antigen binding component of the fusion protein may bind to the cancer cells, and the heat shock protein component may activate the APCs. The target or antigen binding component may be any antibody or other molecule that recognizes a cancer cell of interest. In one aspect, the target or antigen binding component is a single chain antibody, a variable domain fragment, or a Fab portion of an antibody. In another aspect, the target or antigen binding component is specific for a cancer antigen (e.g., a tumor-specific antigen or a tumor-associated antigen). The cancer antigen may be any identifiable cell surface antigen that is expressed by a cancer of interest. In one embodiment, the tumor antigen is mesothelin, alphafetoprotein, CEA, CA-125, MUC-1, Her2Neu, ETA, NY-ESO-1, VEGF, VEGFR1, VEGFR2, PSMA, prostate specific antigen, HPV17E7, mutant p53, surviving, ras, MAGE, gp100, tyrosinase, WT1, PR1, folate-binding protein, CA-19-9, FAP, G250, or A33. In one embodiment, the antibody is specific for mesothelin. Fusion proteins that recognize and bind to mesothelin are described, for example, in U.S. Pat. No. 7,943,133, which is incorporated herein by reference in its entirety.

In one embodiment, the non-limiting examples of the immune cells include, but are not limited to, dendritic cells, B lymphocytes, mononuclear phagocytes, and/or a combination thereof. The mononuclear phagocytes may be monocytes or macrophages. In another aspect, the immune cells bear at least a CD40 receptor. In another aspect, the immune cells are dendritic cells.

The methods described herein may be used to treat the cancer. In one embodiment, the cancer exhibits a chemorepellant effect. In one embodiment, the chemorepellant effect is mediated by overexpression of CXCL12 (e.g., at a concentration of 100 nM or greater) or other chemorepellant chemokine.

In one embodiment, the cancer comprises breast cancer, head and neck cancer, leukocytic cancer, liver cancer, ovarian cancer, bladder cancer, prostatic cancer, skin cancer, bone cancer, brain cancer, leukemia cancer, lung cancer, colon cancer, anal cancer, CNS cancer, melanoma cancer, renal cancer, cervical cancer, esophageal cancer, testicular cancer, spleenic cancer, kidney cancer, lymphatic cancer, pancreatic cancer, stomach cancer or thyroid cancer. In one embodiment, the cancer is mesothelioma. In one embodiment, the cancer is a hematological malignancy. Hematological malignancies include tumors of the blood, bone marrow, lymph, and lymphatic system, including, but not limited to, leukemias, lymphomas, and myelomas. In one embodiment, the cancer is a human papilloma virus (HPV)-positive cancer.

In one embodiment, the method further comprises selecting a patient having a cancer that exhibits a chemorepellant effect. In another embodiment, the invention further comprises administering to the patient an effective amount of an anti-chemorepellant agent. The anti-chemorepellant agent and the APCs, including dendritic cells, may be administered separately, simultaneously, and/or sequentially. In another aspect, the anti-chemorepellant agent is administered after the administration of the APCs, including dendritic cells. In another aspect, the anti-chemorepellant agent is administered before and/or during the administration of the APCs (e.g., dendritic cells). In one aspect, the anti-chemorepellant agent is administered via injection. In one embodiment, the anti-chemorepellant agent is administered directly or proximal to the tumor. In one embodiment, the anti-chemorepellant agent is administered systemically.

In one embodiment, the APCs have an anti-chemorepellant agent bound thereto via one or more cell surface receptors. The non-limiting examples of the anti-chemorepellant agents include but are not limited to AMD3100 or a derivative thereof, AMD11070 (also called AMD070), AMD12118, AMD11814, AMD13073, FAMD3465, C131, BKT140, CTCE-9908, KRH-2731, TC14012, KRH-3955, BMS-936564/MDX-1338, LY2510924, GSK812397, KRH-1636, T-20, T-22, T-140, TE-14011, T-14012, TN14003, TAK-779, AK602, SCH-351125, tannic acid, NSC 651016, thalidomide, GF 109230X, an antibody that interferes with dimerization of a chemorepellant chemokine, an antibody that interferes with dimerization of a receptor for a chemorepellant chemokine, and/or a combination thereof. In one aspect, the anti-chemorepellant agent is AMD3100.

In one embodiment, the heat shock protein component may be HSP70 or an immune activating fragment and/or modified sequence thereof. The HSP70 or the immune activating fragment and/or modified sequence thereof may be from *Mycobacterium tuberculosis*. In another aspect, the target or antigen binding component comprises a single chain antibody, a variable domain, or a Fab domain.

In another embodiment, the method of treating cancer in a patient further comprises expanding the immune cells, e.g., dendritic cells, in the presence of a growth factor. In one aspect, the growth factor is a cytokine. In another aspect, the non-limiting examples of the growth factors include Flt-3 ligand, GM-CSF, IL-4, M-CSF, IFNα, IL-1β, IL-4, IL-6, IL-13, IL-15, TNFα, and a combination thereof.

In one embodiment, the tumor cells are obtained from the patient. In another embodiment, the tumor cells derive from breast cancer, head and neck cancer, leukocytic cancer, liver cancer, ovarian cancer, bladder cancer, prostatic cancer, skin cancer, bone cancer, brain cancer, leukemia cancer, lung cancer, colon cancer, anal cancer, CNS cancer, melanoma cancer, renal cancer, cervical cancer, esophageal cancer, testicular cancer, spleenic cancer, kidney cancer, lymphatic cancer, pancreatic cancer, stomach cancer or thyroid cancer. In one embodiment, the tumor cells derive from mesothelioma. In one embodiment, the tumor cells are from a hematological malignancy. In one embodiment, the cancer is a HPV-positive cancer.

In one embodiment, the APCs (e.g., dendritic cells) are allogeneic, autologous, or derived from a cell line. In one aspect, the APCs (e.g., dendritic cells) are collected from a patient having a tumor.

In another embodiment, the immune cells, APCs (e.g., dendritic cells), or the tumor cells are immobilized on a solid support. In one aspect, the solid support comprises a column, a sepharose bead, a gel, a matrix, a magnetic bead, or a plastic surface.

In one embodiment, the dendritic cells are differentiated or matured from dendritic cell precursors. In another aspect, the dendritic cell precursors are non-activated or activated. In one aspect, the dendritic cell precursors are free or substantially free of neutrophils, macrophages, lymphocytes, or a combination thereof. In another aspect, the dendritic cell precursors are differentiated in the presence of a growth factor. The growth factor may be a cytokine. In another aspect, the non-limiting examples of the growth factor include but are not limited to Flt-3 ligand, GM-CSF, IL-4, M-CSF, IFNα, IL-1β, IL-4, IL-6, IL-13, IL-15, and TNFα.

In one aspect, this disclosure relates to a method for preparing activated T cells, the method comprising:
a) providing activated antigen-presenting cells that were activated in presence of cancer or tumor cells and a fusion protein ex vivo for a time period sufficient to produce activated antigen-presenting cells, wherein at least one activated antigen-presenting cell displays an antigen derived from the cancer or tumor cells;
b) contacting the activated antigen-presenting cells with T cells for a period of time sufficient to activate the T cells; and
c) isolating the activated T cells;
wherein the fusion protein comprises a cancer or tumor binding component and a heat shock protein component, wherein said cancer or tumor binding component binds to the cancer tumor cells and said heat shock protein component activates antigen-presenting cells. In one embodiment, the isolated activated T cells are free or substantially free of the dendritic cells, cancer or tumor cells and the fusion protein.

In one embodiment, the heat shock protein component comprises HSP70 or an immune activating fragment and/or modified sequence thereof. In one embodiment, the HSP70 or the immune activating fragment and/or modified sequence thereof is from *Mycobacterium tuberculosis*. In one embodiment, the tumor binding component is a single chain antibody, a variable domain, or a Fab domain.

In one embodiment, the APCs were expanded in the presence of a growth factor. In one embodiment, the growth factor is a cytokine. In one embodiment, the growth factor is selected from the group consisting of Flt-3 ligand, GM-CSF, IL-4, M-CSF, IFNα, IL-1β, IL-4, IL-6, IL-13, IL-15 and TNFα.

In one embodiment, the tumor cells are obtained from a patient. In one embodiment, the tumor cells are derived from a patient to be treated as described herein. In one embodiment, the tumor cells are derived from a different patient. In one embodiment, the tumor cells comprise a cancer cell line.

In one embodiment, the term "tumor cells" that are incubated with the immune cells and fusion protein refers to any tumor sample, including but not limited to intact cells, viable cells, non-viable cells, tumor-specific antigen (e.g., isolated antigen, partially isolated antigen, recombinant antigen, etc.), and/or other cellular material derived from a tumor or cancer cell or cell line. In some embodiments, the tumor sample comprises at least a subset of antigens that are identical or similar to antigens associated with a patient's tumor, e.g., that will result in a T cell response against the patient's tumor.

Anti-chemorepellant agents may include, without limitation, molecules that inhibit expression of CXCL12 or CXCR4 or CXCR7 (e.g., antisense or siRNA molecules), molecules that bind to CXCL12 or CXCR4 or CXCR7 and inhibit their function (e.g., antibodies or aptamers), molecules that inhibit dimerization of CXCL12 or CXCR4 or CXCR7, and antagonists of CXCR4 or CXCR7. In one embodiment, the inhibitor of CXCL12 signaling is a CXCR4 antagonist. In one embodiment, the isolated activated T cells are contacted with an effective amount of an anti-chemorepellant agent. In one embodiment, the anti-chemorepellant agent is selected from the group consisting of AMD3100 or a derivative thereof, AMD11070 (also called AMD070), AMD12118, AMD11814, AMD13073, FAMD3465, C131, BKT140, CTCE-9908, KRH-2731, TC14012, KRH-3955, BMS-936564/MDX-1338, LY2510924, GSK812397, KRH-1636, T-20, T-22, T-140, TE-14011, T-14012, TN14003, TAK-779, AK602, SCH-351125, tannic acid, NSC 651016, thalidomide, GF 109230X, an antibody that interferes with dimerization of a chemorepellant chemokine, such as CXCL12, and an antibody that interferes with dimerization of a receptor for a chemorepellant chemokine, such as CXCR4 or CXCR7. In one embodiment, the anti-chemorepellant agent is AMD3100. AMD3100 is described in U.S. Pat. No. 5,583,131, which is incorporated by reference herein in its entirety. In one embodiment, the anti-chemorepellant agent is a CXCR7 antagonist. The CXCR7 antagonist can be but is not limited to CCX771, CCX754, or an antibody that interferes with the dimerization of CXCR7. In certain embodiments, the anti-chemorepellant agent is not an antibody. In certain embodiments, the anti-chemorepellant agent is not a heparinoid. In certain embodiments, the anti-chemorepellant agent is not a peptide. In one embodiment, the amount of anti-chemorepellant agent is sufficient to bind to at least a subset of receptors, e.g., CXCR4 and/or CXCR7, on the surface of the T cells.

In one embodiment, the APCs are allogeneic, autologous, or derived from a cell line. In one embodiment, the T cells are allogeneic, autologous, or derived from a cell line. In one embodiment, the APCs and/or the T cells are isolated from a patient having cancer. In some embodiments, the APCs and T cells are derived from the same source, e.g., the same patient.

In one embodiment, either the APCs or the tumor cells are immobilized on a solid support. In one embodiment, the activated APCs are isolated by isolating the solid support from the tumor cells and fusion protein.

In one embodiment, the T cells are immobilized on a solid support. In one embodiment, the activated T cells are isolated by isolating the solid support from the APCs.

In one embodiment, the solid support comprises a surface of a column, a sepharose bead, a gel, a matrix, a magnetic bead, or a plastic surface.

In one embodiment, this disclosure relates to a method for treating a cancer, e.g., a tumor, in a patient, the method comprising administering an effective amount of activated T cells to the patient, wherein the activated T cells were prepared by:
providing activated APCs prepared by incubating APCs with cancer cells and a fusion protein, wherein the fusion protein comprises a cancer cell binding component and a heat shock protein component, wherein said cancer binding component binds to the cancer cells and said heat shock protein component activates APCs; and
contacting the activated APCs with T cells for a period of time sufficient to activate the T cells.

In one embodiment, provided herein is a method for treating a cancer, e.g., a tumor, in a patient, the method comprising:

a) providing activated APCs that were activated by incubating APCs in the presence of cancer cells and a fusion protein ex vivo for a time period sufficient to produce activated APCs, wherein at least one activated APC displays an antigen derived from the cancer cells;

b) contacting the activated APCs with T cells for a period of time sufficient to activate the T cells;

c) isolating the activated T cells; and d) administering an effective amount of the activated T cells to the patient;

wherein the fusion protein comprises a cancer cell binding component and a heat shock protein component, wherein said cancer cell binding component binds to the cancer cells and said heat shock protein component activates APCs. In one embodiment, the isolated activated T cells are free or substantially free of the activated APCs, cancer cells and the fusion protein.

In one embodiment, the method further comprises administering to the patient an effective amount of an anti-chemorepellant agent. In one embodiment, the activated T cells have an anti-chemorepellant agent bound thereto via one or more cell surface receptors. In one embodiment, the one or more cell surface receptors comprise CXCR4 and/or CXCR7.

In one embodiment, the anti-chemorepellant agent is one described above, e.g., AMD3100 or a derivative thereof, AMD11070 (also called AMD070), AMD12118, AMD11814, AMD13073, FAMD3465, C131, BKT140, CTCE-9908, KRH-2731, TC14012, KRH-3955, BMS-936564/MDX-1338, LY2510924, GSK812397, KRH-1636, T-20, T-22, T-140, TE-14011, T-14012, TN14003, TAK-779, AK602, SCH-351125, tannic acid, NSC 651016, thalidomide, GF 109230X, an antibody that interferes with dimerization of a chemorepellant chemokine, or an antibody that interferes with dimerization of a receptor for a chemorepellant chemokine. In one embodiment, the anti-chemorepellant agent is an AMD3100 derivative. In one embodiment, the anti-chemorepellant agent is AMD3100.

The methods described herein may be used to treat the cancer. In one embodiment, the cancer exhibits a chemorepellant effect. In one embodiment, the chemorepellant effect is mediated by overexpression of CXCL12 or other chemorepellant chemokine.

In one embodiment, the cancer comprises breast cancer, leukocytic cancer, liver cancer, ovarian cancer, head and neck cancer, bladder cancer, prostatic cancer, skin cancer, bone cancer, brain cancer, leukemia cancer, lung cancer, colon cancer, anal cancer, CNS cancer, melanoma cancer, renal cancer, cervical cancer, esophageal cancer, testicular cancer, spleenic cancer, kidney cancer, lymphatic cancer, pancreatic cancer, stomach cancer or thyroid cancer. In one embodiment, the cancer is mesothelioma. In one embodiment, the cancer is a hematological malignancy. Hematological malignancies include cancers of the blood, bone marrow, lymph, and lymphatic system, including, but not limited to, leukemias, lymphomas, and myelomas. In one embodiment, the cancer is a HPV-positive cancer.

In one embodiment, this invention relates to a composition comprising immune cells and an effective amount of a fusion protein, said fusion protein comprising a cancer cell binding component and a stress protein component.

In one embodiment, this invention relates to a pharmaceutical composition comprising activated antigen presenting cells and an anti-chemorepellant agent.

In one embodiment, the term "tumor cells" that are incubated with the immune cells and fusion protein refers to any tumor sample, including but not limited to intact cells, viable cells, non-viable cells, tumor-specific antigen (e.g., isolated antigen, partially isolated antigen, recombinant antigen, etc.), and/or other cellular material derived from a tumor or cancer cell or cell line. In some embodiments, the tumor sample comprises at least a subset of antigens that are identical or similar to antigens associated with a patient's tumor, e.g., that will result in a T cell response against the patient's tumor.

In one embodiment, provided herein is a pharmaceutical composition comprising activated APCs and an anti-chemorepellant agent. In one embodiment, the APCs were activated by a method as described herein.

In one embodiment, the activated APCs have an anti-chemorepellant agent bound thereto via one or more cell surface receptors. In one embodiment, the one or more cell surface receptors comprise CXCR4 and/or CXCR7.

In one embodiment, provided herein is a pharmaceutical composition comprising activated T cells and an anti-chemorepellant agent. In one embodiment, the T cells were activated by a method as described herein.

In one embodiment, the activated T cells have an anti-chemorepellant agent bound thereto via one or more cell surface receptors. In one embodiment, the one or more cell surface receptors comprise CXCR4 or CXCR7.

In one embodiment, the composition further comprises a pharmaceutically acceptable excipient. In one embodiment, the composition further comprises an effective amount of a fusion protein as described herein.

In one embodiment is provided a composition comprising a complex including an activated APC, a fusion protein, and a T cell. In one embodiment, the fusion protein comprises a cancer cell binding component and a stress protein component. In one embodiment, the T cell is activated by the interaction with the activated APC and/or fusion protein. In one embodiment, the APC comprises an antigen derived from a cancer sample on the cell surface.

BRIEF DESCRIPTION OF THE DRAWINGS

FIG. 1 shows the peptide sequence of VIC-007 (SEQ ID NO.: 1) and VIC-008 (SEQ ID NO.: 2).

DETAILED DESCRIPTION

Figure 2A:
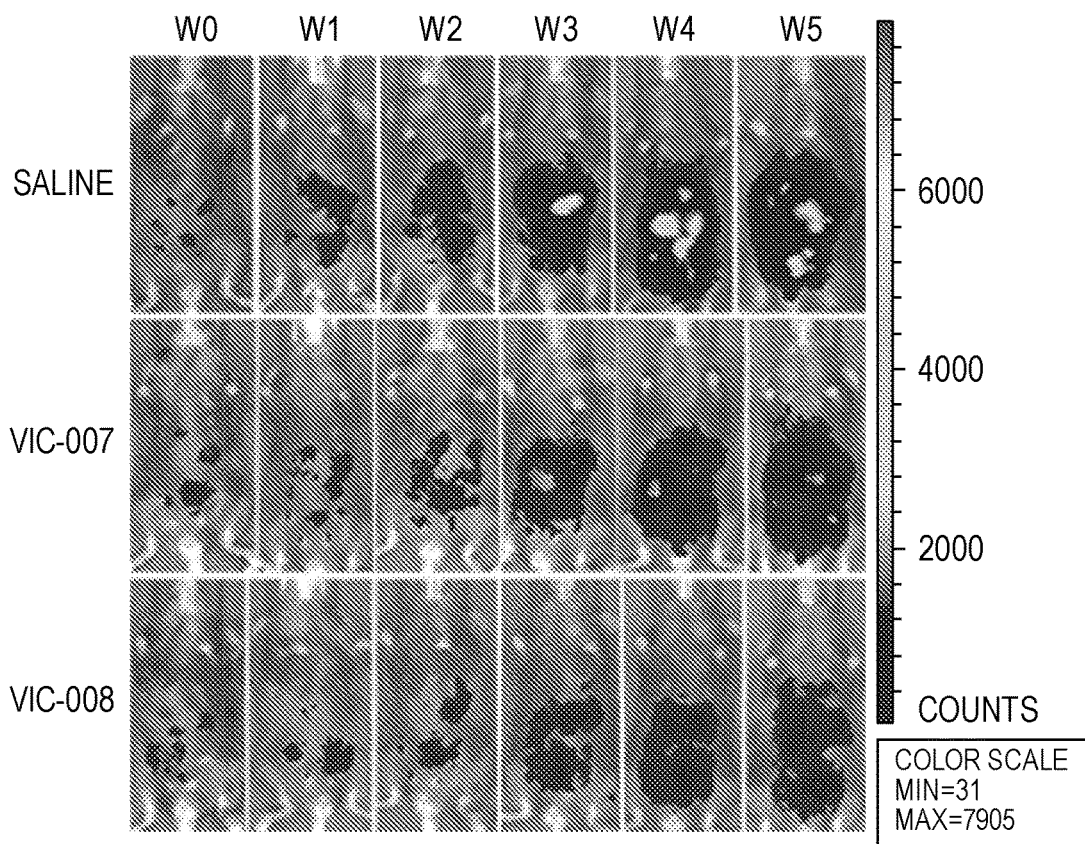
FIG. 2A indicates intraperitoneal ovarian tumor growth using bioluminescence signals for each treatment (saline, VIC-007, or VIC-008) at weeks 0 (W0), 1 (W1), 2 (W2), 3 (W3), 4 (W4) and 5 (W5).

After reading this description, it will become apparent to one skilled in the art how to implement the invention in various alternative embodiments and alternative applications. However, not all embodiments of the present invention are described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

Definitions

Unless defined otherwise, all technical and scientific terms used herein have the same meaning as commonly understood by one of ordinary skill in the art to which this invention belongs.

In this specification and in the claims that follow, reference will be made to a number of terms that shall be defined to have the following meanings:

The terminology used herein is for the purpose of describing particular embodiments only and is not intended to be limiting the invention. As used herein, the singular forms "a," "an" and "the" are intended to include the plural forms as well, unless the context clearly indicates otherwise.

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

The term "antigen-presenting cell" or "APC" refers to an immune cell that is capable of presenting an antigen to the immune system including dendritic cells, mononuclear phagocytes (e.g., monocytes and macrophages), B lymphocytes, and the like, from a mammal (e.g., human or mouse). The antigen may be presented on the surfaces of the antigen-presenting cells.

The term "dendritic cell" refers to one type of antigen-presenting cell capable of activating T cells and/or stimulating the differentiation of B cells.

The term "CD40 receptor" refers to a costimulatory protein, peptide, or polypeptide, or a nucleic acid encoding the peptide, polypeptide or protein. The CD40 receptor may be present in immune cells, including but not limited to APCs.

"Optional" or "optionally" means that the subsequently described event or circumstance can or cannot occur, and that the description includes instances where the event or circumstance occurs and instances where it does not.

The term "comprising" or "comprises" is intended to mean that the compositions and methods include the recited elements, but not excluding others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

The terms "patient," "subject," "individual," and the like are used interchangeably herein, and refer to any animal, or cells thereof whether in vitro or in situ, amenable to the methods described herein. In one embodiment, the patient, subject, or individual is a mammal. In some embodiments, the mammal is a mouse, a rat, a guinea pig, a non-human primate, a dog, a cat, or a domesticated animal (e.g., horse, cow, pig, goat, sheep). In some embodiments, the patient, subject or individual is a human.

The term "treating" or "treatment" covers the treatment of a disease or disorder described herein, in a subject, such as a human, and includes: (i) inhibiting a disease or disorder, i.e., arresting its development; (ii) relieving a disease or disorder, i.e., causing regression of the disease or disorder; (iii) slowing progression of the disease or disorder; and/or (iv) inhibiting, relieving, or slowing progression of one or more symptoms of the disease or disorder. For example, treatment of a cancer or tumor includes, but is not limited to, reduction in size of the tumor, elimination of the tumor and/or metastases thereof, remission of the cancer, inhibition of metastasis of the tumor, reduction or elimination of at least one symptom of the cancer, and the like.

The term "administering" or "administration" of an agent to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

"Pharmaceutically acceptable composition" refers to a composition that is suitable for administration to a mammal, particularly, a human.

It is also to be appreciated that the various modes of treatment or prevention of medical diseases and conditions as described are intended to mean "substantial," which includes total but also less than total treatment or prevention, and wherein some biologically or medically relevant result is achieved.

The phrase "concurrently administering" refers to administration of at least two agents to a patient over a period of time. As used herein, the word "concurrently" means sufficiently close in time to produce a combined effect (that is, concurrently can be simultaneously, or it can be two or more events occurring within a short time period before or after each other). Concurrent administration includes, without limitation, separate, sequential, and simultaneous administration.

The term "separate" administration refers to an administration of at least two active ingredients at the same time or substantially the same time by different routes or in different compositions.

The term "sequential" administration refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients.

The term "simultaneous" administration refers to the administration of at least two active ingredients by the same route and at the same time or at substantially the same time.

The term "therapeutic" as used herein means a treatment. A therapeutic effect is obtained by suppression, remission, or eradication of a disease state.

The term "prevent" or "preventative" as used herein means a prophylactic treatment. A preventative effect is obtained by delaying the onset of a disease state or decreasing the severity of a disease state when it occurs.

The term "therapeutically effective amount," "prophylactically effective amount," or "effective amount" refers to an amount of the agent that, when administered, is sufficient to cause the desired effect. For example, an effective amount of an anti-chemorepellant agent may be an amount sufficient to have an anti-chemorepellant effect on a cancer cell or tumor (e.g., to attenuate a chemorepellant effect from the tumor or cancer cell). The therapeutically effective amount of the agent may vary depending on the tumor being treated and its severity as well as the age, weight, etc., of the patient to be treated. The skilled artisan will be able to determine appropriate dosages depending on these and other factors. The compositions can also be administered in combination with one or more additional therapeutic compounds. In the methods described herein, the therapeutic compounds may be administered to a subject having one or more signs or symptoms of a disease or disorder.

The term "kill" with respect to a cell/cell population is directed to include any type of manipulation that will lead to the death of that cell/cell population.

The terms "antibodies" and "antibody" as used herein include polyclonal, monoclonal, single chain, chimeric, humanized and human antibodies, prepared according to conventional methodology.

The term "CXCR4/CXCL12 antagonist" or "CXCR7/CXCL12 antagonist" refers to a compound that antagonizes CXCL12 binding to CXCR4 and/or CXCR7 or otherwise reduces the fugetactic effect of CXCL12.

By "chemorepellant activity" or "chemorepellant effect" it is meant the ability of an agent to repel (or chemorepel) a eukaryotic cell with migratory capacity (i.e., a cell that can move away from a repellant stimulus), as well as the chemorepellant effect of a chemokine secreted by a cell, e.g., a tumor cell. Usually, the chemorepellant effect is present in an area around the cell wherein the concentration of the chemokine is sufficient to provide the chemorepellant effect. Some chemokines, including interleukin 8 and CXCL12, may exert chemorepellant activity at high concentrations (e.g., over about 100 nM), whereas lower concentrations exhibit no chemorepellant effect and may even be chemoattractant.

Accordingly, an agent with chemorepellant activity is a "chemorepellant agent." Such activity can be detected using any of a variety of systems well known in the art (see, e.g., U.S. Pat. No. 5,514,555 and U.S. Patent Application Pub. No. 2008/0300165, each of which is incorporated by reference herein in its entirety). A preferred system for use herein is described in U.S. Pat. No. 6,448,054, which is incorporated herein by reference in its entirety.

The term "anti-chemorepellant effect" refers to the effect of the anti-chemorepellant agent to attenuate or eliminate the chemorepellant effect of the chemokine.

The term "autogeneic" or "autologous" refers to the origin of a cell, when the cell administered to an individual is derived from the individual or a genetically identical individual (i.e., an identical twin of the individual). An autogeneic cell can also be a progeny of an autogeneic cell. The term also indicates that cells of different cell types are derived from the same individuals or genetically identical individuals.

The term "allogeneic" or "allogenic" also refers to the origin of a cell, when the cell being administered to an individual is derived from an individual not genetically identical to the recipient but from the same species, including a progeny of an allogeneic cell. Cells are still called allogeneic when they are of different cell types but are derived from genetically non-identical donors, or when they are progenies of cells derived from genetically non-identical donors.

"Immune cells" as used herein are cells of hematopoietic origin that are involved in the specific recognition of antigens. Immune cells include APCs, such as dendritic cells or macrophages, B cells, T cells, etc.

The term "anti-cancer therapy" as used herein refers to traditional cancer treatments, including chemotherapy and radiotherapy, as well as immunotherapy and vaccine therapy.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (e.g., IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

A "fusion protein" or "fusion polypeptide" refers to a hybrid polypeptide which comprises polypeptide portions from at least two different polypeptides. The portions may be from proteins of the same organism, in which case the fusion protein is said to be "intraspecies," "intragenic," etc. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. A first polypeptide may be fused to the N-terminus, the C-terminus, or the N- and C-terminus of a second polypeptide. Furthermore, a first polypeptide may be inserted within the sequence of a second polypeptide.

The term "immunogenic" refers to the ability of a substance to elicit an immune response. An "immunogenic composition" or "immunogenic substance" is a composition or substance which elicits an immune response. An "immune response" refers to the reaction of a subject to the presence of an antigen, which may include at least one of the following: making antibodies, developing immunity, developing hypersensitivity to the antigen, and developing tolerance.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

As used herein, a "stress protein" also known as a "heat shock protein" or "HSP" is a protein that is encoded by a stress gene, and is therefore typically produced in significantly greater amounts upon the contact or exposure of the stressor to the organism. The term "stress protein" as used herein is intended to include such portions and peptides of a stress protein. A "stress gene," also known as "heat shock gene," as used herein, refers to a gene that is activated or otherwise detectably upregulated due to the contact or exposure of an organism (containing the gene) to a stressor, such as but not limited to heat shock, hypoxia, glucose deprivation, heavy metal salts, inhibitors of energy metabolism and electron transport, and protein denaturants, or to certain benzoquinone ansamycins. Nover, L., Heat Shock Response, CRC Press, Inc., Boca Raton, Fla. (1991). "Stress gene" also includes homologous genes within known stress gene families, such as certain genes within the HSP70 and HSP90 stress gene families, even though such homologous genes are not themselves induced by a stressor. Each of the terms stress gene and stress protein as used in the present specification may be inclusive of the other, unless the context indicates otherwise.

The term "vaccine" refers to a substance that elicits an immune response and also confers protective immunity upon a subject.

Activated Antigen-Presenting Cells (APCs)
Antigen-Presenting Cells (APCs)

The antigen-presenting cells (APCs) may include dendritic cells, B lymphocytes, mononuclear phagocytes (e.g., monocytes and/or macrophages), and/or other cell types expressing the necessary MHC/co-stimulatory molecules. In one aspect, the APCs comprise a costimulatory protein, e.g., CD40, which is important for the activation of the APCs. In one embodiment, the APCs may be presented with antigens by pulsing, in which the APCs are exposed to antigenic proteins or polypeptides. The proteins or peptides may be recombinant or natural products. In another embodiment, APCs are exposed to the nucleic acids encoding the proteins or peptides in the presence of transfection agents known in the art, including but not limited to cationic lipids.

Transfected or pulsed APCs can subsequently be administered to the host via an intravenous, subcutaneous, intranasal, intramuscular, or intraperitoneal route of delivery. Protein/peptide antigens can also be delivered in vivo with adjuvant via the intravenous, subcutaneous, intranasal, intramuscular or intraperitoneal route of delivery.

According to the invention, foster antigen-presenting cells may also be used as a substitute for the antigen-presenting cells. The foster antigen-presenting cells lack antigen processing activity, whereby they express MHC molecules free of bound peptides. In one aspect, foster APCs are derived from the human cell line 174X CEM.T2, referred to as T2, which contains a mutation in its antigen processing pathway that restricts the association of endogenous peptides with cell surface MHC class I molecules. Zweerink et al., *J. Immunol.* 150:1763-1771(1993). Transduction of T2 cells with specific recombinant MHC alleles allows for redirection of the MHC restriction profile. Libraries tailored to the recombinant allele will be preferentially presented by them because the anchor residues will prevent efficient binding to the endogenous allele. High level expression of MHC molecules makes the APCs more visible to the CTLs. Expressing the MHC allele of interest in T2 cells using a powerful transcriptional promoter (e.g., the CMV promoter) results in a more reactive APC.

In one embodiment, the APCs are modified to express or over-express co-stimulatory molecules. Co-stimulatory molecules include, but are not limited to, CD40, MHC class I and/or class II, B7-1 (CD80), B7-2 (CD86), ICAM-1, interleukin 1 (IL-1), and LFA-3. See, e.g., Hodge et al. J Natl Cancer Inst (2000) 92 (15): 1228-1239, which is incorporated herein by reference in its entirety.

Dendritic Cells

As one type of antigen-presenting cells, dendritic cells are effective in presenting antigens and initiating immune responses, particularly the immune responses associated with T cells. Dendritic cells are present in skin, nose, lung, intestines, blood, and many other tissues and organs. The immunogenicity of the dendritic cells is partly due to their ability to process antigen materials and present them on the cell surface.

After capturing the antigens, the dendritic cells can present the antigen to T cells. The dendritic cells become mature with increased surface expression of class II MHC and costimulatory molecules. Santambrogio et al., PNAS, 96(26): 15056-15061 (1999). Mature dendritic cells may lose the ability to further process exogenous antigens. Maturation of the dendritic cells may also be accompanied with the loss of acidic organelles, where the antigens were processed. Kampgen et al., PNAS, 88: 3014-3018 (1991).

The efficiency of the dendritic cells may be limited by the small number of the cells in any given organs. For example, around 0.1% of the white cells exist as dendritic cells in human blood. Dendritic cells from some organs (e.g., spleen and afferent lymphatic) arise from precursors. Thus, in one aspect of the invention, dendritic cells are obtained or expanded from dendritic cell precursors. The methods of expanding or obtaining dendritic cells are described in U.S. Pat. No. 5,994,126, which is incorporated herein by reference in its entirety.

Methods of Making Activated Antigen-Presenting Cells

The activated APCs used in the methods described herein to activate T cells are activated using a fusion protein and tumor cells or a tumor sample.

In one embodiment, the APCs used in the methods described herein are activated by incubating an effective amount of a fusion protein with immune cells and tumor cells or sample under conditions so as to produce activated APCs. In one embodiment, the APCs are activated by a method which comprises incubating immune cells ex vivo in the presence of tumor cells and a fusion protein for a time period sufficient to produce the activated APCs, wherein at least one activated APC displays an antigen derived from the tumor cells. In one embodiment, the method further comprises isolating the activated APCs. In one embodiment, the isolated activated APCs are free or substantially free of the tumor cells and/or the fusion protein.

The term "substantially free" as used herein refers to nearly complete removal of the tumor cells and/or fusion protein. In one embodiment, the activated APCs are free of the tumor cells and/or fusion protein. In one embodiment, the activated APCs are free of the tumor cells. In one embodiment, at least about 90%, at least about 91%, at least about 92%, at least about 93%, at least about 94%, at least about 95%, at least about 96%, at least about 97%, at least about 98%, at least about 99%, or at least about 99.9% of the tumor cells are removed from the activated APCs by isolation. In one embodiment, at least about 90%, at least about 91%, at least about 92%, at least about 93%, at least about 94%, at least about 95%, at least about 96%, at least about 97%, at least about 98%, at least about 99%, or at least about 99.9% of the fusion protein is removed from the activated APCs by isolation.

In one aspect, the fusion protein comprises an antigen-binding component and a heat shock protein component. While the antigen-binding component binds to the tumor cell, the heat shock protein component activates the APCs.

In one embodiment, the antigen-binding component of the fusion protein may be any antibody or other molecule that recognizes a tumor or cancer cell of interest. In one embodiment, the antigen-binding component is a single chain antibody, a variable domain, or a fragment antigen-binding ("Fab") domain of an antibody.

In one aspect, the tumor cells are obtained from a patient.

In one aspect, the antigen-binding component is specific for a cancer antigen (e.g., a tumor-specific antigen or a tumor-associated antigen). The cancer antigen may be any identifiable cell surface antigen that is expressed by a cancer of interest. In one embodiment, the cancer antigen is mesothelin, alphafetoprotein, CEA, CA-125, MUC-1, Her2Neu, ETA, NY-ESO-1, VEGF, VEGFR1, VEGFR2, PSMA, prostate specific antigen, HPV17E7, mutant p53, surviving, ras, MAGE, gp100, tyrosinase, WT1, PR1, folate-binding protein, CA-19-9, FAP, G250, or A33. In one embodiment, the antibody is specific for mesothelin. Fusion proteins that recognize and bind to mesothelin are described, for example, in U.S. Pat. No. 7,943,133, which is incorporated herein by reference in its entirety.

In one embodiment, the immune cells (APCs) include, but are not limited to, dendritic cells, B lymphocytes, and mononuclear phagocytes. The mononuclear phagocytes may include monocytes and/or macrophages. In some aspects, the immune cells comprise at least one CD40. In another aspect, the immune cells are dendritic cells.

In one embodiment, the heat shock protein component includes but is not limited to HSP70 and/or an immune activating fragment and/or modified sequence thereof. In another aspect, the HSP70 or the immune activating fragment and/or modified sequence thereof is from *Mycobacterium tuberculosis*.

In one embodiment, the method of preparing the APCs further comprises expanding the immune cells in the presence of a growth factor. In one embodiment, the method of preparing the APCs further comprises expanding the activated APCs in the presence of a growth factor. In one aspect, the growth factor is a cytokine. In another aspect, the growth factor includes, but is not limited to, Flt-3 ligand, GM-CSF, IL-4, M-CSF, IFNα, IL-1β, IL-4, IL-6, IL-13, IL-15, TNFα, or any combination thereof.

In one embodiment, the APCs are allogeneic, autologous, or derived from a cell line. In another embodiment, the APCs are collected from a patient having a tumor. In one aspect, either the APCs or the tumor cells are immobilized on a solid support. The solid support includes but is not limited to a surface of a column, a sepharose bead, a gel, a matrix, a magnetic bead, a plastic surface, or any combination thereof.

In another embodiment, the dendritic cells are differentiated or matured from dendritic cell precursors. The dendritic cell precursors may be activated, or not be activated. In another aspect, the dendritic cell precursors are free or substantially free of neutrophils, macrophages, lymphocytes, or a combination thereof. In such an aspect, the term "substantially free" indicates that neutrophils, macrophages, and/or lymphocytes comprise less than about 10%, e.g., less than about 5%, e.g., less than about 2%, e.g., less than about 1% of the total cells in a dendritic cell precursor composition.

In one aspect, the dendritic cell precursors are differentiated in the presence of a growth factor. The growth factor may be a cytokine. In another aspect, the growth factor is selected from a group consisting of Flt-3 ligand, GM-CSF, IL-4, M-CSF, IFNα, IL-1β, IL-4, IL-6, IL-13, IL-15 and TNFα.

In one embodiment, the APCs are modified to express or over-express co-stimulatory molecules. Co-stimulatory molecules include, but are not limited to, CD40, MHC class I and/or class II, B7-1 (CD80), B7-2 (CD86), ICAM-1, interleukin 1 (IL-1), and LFA-3. See, e.g., Hodge et al. J Natl Cancer Inst (2000) 92 (15): 1228-1239, which is incorporated herein by reference in its entirety.

Anti-Chemorepellant Agents

Many tumors have chemorepellant effects, e.g., on immune cells, due to chemokines secreted by the tumor cells. High concentrations of the chemokines secreted by the tumor cells can have chemorepellant effects on cells, whereas lower concentrations do not have such effects or even result in chemoattraction. For example, T cells are repelled by CXCL12 (SDF-1) by a concentration-dependent and CXCR4 receptor-mediated mechanism.

The anti-chemorepellant agent may be any such agent known in the art, for example an anti-chemorepellant agent as described in U.S. Patent Application Publication No. 2008/0300165, which is hereby incorporated by reference in its entirety.

Anti-chemorepellant agents include any agents that specifically inhibit chemokine and/or chemokine receptor dimerization, thereby blocking the chemorepellant response to a chemorepellant agent. Certain chemokines, including IL-8 and CXCL12 can also serve as chemorepellants at high concentrations (e.g., above 100 nM) where many of the chemokines exist as a dimer. Dimerization of the chemokines elicits a differential response in cells, causing dimerization of chemokine receptors, an activity which is interpreted as a chemorepellant signal. Blocking the chemorepellant effect of high concentrations of chemokines secreted by a tumor can be accomplished, for example, by anti-chemorepellant agents which inhibit chemokine dimer formation or chemokine receptor dimer formation. For example, antibodies that target and block chemokine receptor dimerization, e.g., by interfering with the dimerization domains or ligand binding, can be anti-chemorepellant agents. Anti-chemorepellant agents that act via other mechanisms of action, e.g., that reduce the amount of chemorepellant cytokine secreted by the cells, inhibit dimerization, and/or inhibit binding of the chemokine to a target receptor, are also encompassed by the present invention. Where desired, this effect can be achieved without inhibiting the chemotactic action of monomeric chemokine.

In other embodiments, the anti-chemorepellant agent is a CXCR4 antagonist, CXCR7 antagonist, CXCR3 antagonist, CXCR4/CXCL12 antagonist, CXCR7/CXCL12 antagonist, or selective PKC inhibitor. Anti-chemorepellant agents may include, without limitation, molecules that inhibit expression of CXCL12 or CXCR4 or CXCR7 (e.g., antisense or siRNA molecules), molecules that bind to CXCL12 or CXCR4 or CXCR7 and inhibit their function (e.g., antibodies or aptamers), molecules that inhibit dimerization of CXCL12 or CXCR4 or CXCR7, and antagonists of CXCR4 or CXCR7.

The CXCR4 antagonist can be but is not limited to AMD3100 (plerixafor) or a derivative thereof, AMD11070 (also called AMD070), AMD12118, AMD11814, AMD13073, FAMD3465, C131, BKT140, CTCE-9908, KRH-2731, TC14012, KRH-3955, BMS-936564/MDX-1338, LY2510924, GSK812397, KRH-1636, T-20, T-22, T-140, TE-14011, T-14012, or TN14003, derivatives thereof, or an antibody that interferes with the dimerization of CXCR4. Additional CXCR4 antagonists are described, for example, in U.S. Patent Pub. No. 2014/0219952 and Debnath et al. *Theranostics,* 2013; 3(1): 47-75, each of which is incorporated herein by reference in its entirety, and include TG-0054 (burixafor), AMD3465, NIBR1816, AMD070, and derivatives thereof.

The CXCR3 antagonist can be but is not limited to TAK-779, AK602, or SCH-351125, or an antibody that interferes with the dimerization of CXCR3.

The CXCR4/CXCL12 antagonist can be but is not limited to tannic acid, NSC 651016, or an antibody that interferes with the dimerization of CXCR4 and/or CXCL12.

The CXCR7/CXCL12 antagonist can be but is not limited to CCX771, CCX754, or an antibody that interferes with the dimerization of CXCR7 and/or CXCL12.

The selective PKC inhibitor can be but is not limited to thalidomide or GF 109230X.

In one embodiment, the anti-chemorepellant agent is AMD3100 (plerixafor). AMD3100 is described in U.S. Pat. No. 5,583,131, which is incorporated by reference herein in its entirety.

In one embodiment, the anti-chemorepellant agent is an AMD3100 derivative. AMD3100 derivatives include, but are not limited to, those found in U.S. Pat. Nos. 7,935,692 and 5,583,131 (USRE42152), each of which is incorporated herein by reference in its entirety.

In certain embodiments, the anti-chemorepellant agent is not an antibody. In certain embodiments, the anti-chemorepellant agent is not a heparinoid. In certain embodiments, the anti-chemorepellant agent is not a peptide.

In one embodiment, the anti-chemorepellant agent is coupled with a molecule that allows targeting of a tumor. In one embodiment, the anti-chemorepellant agent is coupled with (e.g., bound to) an antibody specific for the tumor to be targeted. In one embodiment, the anti-chemorepellant agent coupled to the molecule that allows targeting of the tumor is administered systemically.

In one embodiment, the anti-chemorepellant agent is administered in combination with an additional compound that enhances the anti-chemorepellant activity of the agent. In one embodiment, the additional compound is granulocyte colony stimulating factor ("G-CSF"). In one embodiment, G-CSF is not administered.

Fusion Protein

This disclosure relates to fusion proteins comprising a stress protein component and a target or antigen binding component, and methods of using the same. In particular, this disclosure relates to treating a patient having a disease, e.g., a cancer or a disease caused by a pathogen, that can be recognized by a fusion protein as described herein. Preferably, the disease expresses a chemorepellant activity such that immune cells are inhibited in the vicinity of the diseased cells, pathogen, or tumor cells.

Examples and methods of making fusion proteins contemplated in the present invention are described in U.S. Pat. Nos. 8,143,387 and 7,943,133 and PCT Application Number PCT/US2017/021911, each of which is incorporated herein by reference in its entirety.

Stress Protein Component

The stress protein component (also referred to as the stress protein domain) may comprise any polypeptide sequence that activates APCs. In some embodiments, the polypeptide sequence is derived from a stress protein. However, any APC-activating polypeptide is contemplated.

Any suitable stress protein (e.g., heat shock protein) can be used in the fusion polypeptides of the present invention. For example, HSP60 and/or HSP70 can be used. Turning to stress proteins generally, cells respond to a stressor (typically heat shock treatment) by increasing the expression of a group of genes commonly referred to as stress, or heat shock, genes. Heat shock treatment involves exposure of cells or organisms to temperatures that are one to several degrees Celsius above the temperature to which the cells are adapted. In coordination with the induction of such genes, the levels of corresponding stress proteins increase in stressed cells.

In bacteria, the predominant stress proteins are proteins with molecular sizes of about 70 kDa and 60 kDa, which are commonly referred to as HSP70 and HSP60, respectively. Stress proteins appear to participate in important cellular processes such as protein synthesis, intracellular trafficking, and assembly and disassembly of protein complexes. It appears that the increased amounts of stress proteins synthesized during stress serve primarily to minimize the consequences of induced protein unfolding. Indeed, the pre-exposure of cells to mildly stressful conditions that induce the synthesis of stress proteins affords protection to the cells from the deleterious effects of a subsequent, more extreme stress.

The major stress proteins appear to be expressed in every organism and tissue type examined so far. Also, it appears that stress proteins represent the most highly conserved group of proteins identified to date. For example, when stress proteins in widely diverse organisms are compared, HSP90 and HSP70 exhibit 50% or higher identity at the amino acid level and share many similarities at non-identical positions. Similar or higher levels of homology exist between different members of a particular stress protein family within species.

The stress proteins, particularly HSP 70, HSP 60, HSP 20-30 and HSP 10, are among the major determinants recognized by the host immune system in the immune response to infection by *Mycobacterium tuberculosis* and *Mycobacterium leprae*. However, individuals, including healthy individuals with no history of mycobacterial infection or autoimmune disease, also carry T cells that recognize both bacterial and human HSP 60 epitopes. This system recognizing stress protein epitopes presumably constitutes an "early defense system" against invading organisms. The system may be maintained by frequent stimulation by bacteria and viruses.

Families of stress genes and proteins for use in the fusion polypeptides are those well known in the art and include, for example, HSP 100-200, HSP 100, HSP 90, Lon, HSP 70, HSP 60, TF55, HSP 40, FKBPs, cyclophilins, HSP 20-30, ClpP, GrpE, HSP 10, ubiquitin, calnexin, and protein disulfide isomerases. In certain embodiments, the stress protein is HSP 70 or HSP 60. In certain embodiments, the stress protein is a fragment of Hsp70 or Hsp60 and/or a modified sequence of Hsp70 or Hsp60. As use herein, a "modified sequence" of a stress protein such as Hsp70 is a sequence comprising one or more additions, deletion, or substitutions that retains at least 50% of at least one of the biological activity of the stress protein, e.g., the ability to stimulate antigen presenting cells, e.g., at least 50%, 60%, 70%, 80%, or more of the biological activity. In some embodiments, the modified sequence has an enhanced biological activity compared to the wild-type sequence. In some embodiments, the modified sequence is one disclosed in PCT Application No. PCT/US2017/021911, incorporated by reference herein in its entirety.

The examples of HSP 100-200 include Grp170 (for glucose-regulated protein). HSP 100 examples include mammalian HSP 110, yeast HSP 104, ClpA, ClpB, ClpC, ClpX and ClpY. HSP 90 examples include HtpG in *E. coli*, HSP 83 and Hsc83 in yeast, and HSP 90alpha, HSP 90beta and Grp94 in humans. HSP 70 examples include HSP 72 and Hsc73 from mammalian cells, DnaK from bacteria, particularly mycobacteria such as *Mycobacterium leprae, Mycobacterium tuberculosis*, and *Mycobacterium bovis* (such as Bacille-Calmette Guerin, referred to herein as Hsp71), DnaK from *Escherichia coli*, yeast, and other prokaryotes, and BiP and Grp78. HSP 60 examples include HSP 65 from mycobacteria. Bacterial HSP 60 is also commonly known as GroEL, such as the GroEL from *E. coli*. TF55 examples include Tep1, TRiC and thermosome. HSP 40 examples include DnaJ from prokaryotes such as *E. coli* and mycobacteria and HSJ1, HDJ1 and HSP 40. FKBPs examples include FKBP12, FKBP13, FKBP25, and FKBP59, Fpr1 and Nep1. Cyclophilin examples include cyclophilinsA, Band C. HSP 10 examples include GroES and Cpn10.

In particular embodiments, the stress proteins of the present invention are obtained from enterobacteria, mycobacteria (particularly *M. leprae, M. tuberculosis, M. vaccae, M. smegmatis* and *M. bovis*), *E. coli*, yeast, *Drosophila*, vertebrates, avians, chickens, mammals, rats, mice, primates, or humans.

In one embodiment, the stress protein comprises *Mycobacterium tuberculosis*-derived heat shock protein 70 (MtbHsp70). MtbHsp70 is well characterized and functions as a potent immune-activating adjuvant. It stimulates monocytes and dendritic cells (DCs) to produce CC-chemokines, which attract antigen processing and presenting macrophages, DCs, and effector T and B cells.

A fusion polypeptide may comprise an amino acid sequence that is at least about 80%, 85%, 90%, 95%, 98%, or 99% identical to a stress protein described herein.

A fusion polypeptide may comprise an amino acid sequence which is a fragment and/or modification of the stress protein as described herein.

Target Binding Component

The target binding component of the fusion protein may be any molecule that specifically binds an antigen associated with the disease to be treated. In certain embodiments, the target binding component is an antibody or a fragment thereof. The terms "antigen-binding," "target binding," and "tumor-binding" are used interchangeably herein.

In one aspect, the target binding component is a single chain antibody. In one aspect, the target binding component is a variable domain fragment. In one aspect, the target binding component is a Fab portion of an antibody.

In one aspect, the target binding component is specific for a cancer antigen (e.g., a tumor-specific antigen or a tumor-associated antigen), and may be referred to as an antigen binding component. The cancer antigen may be any identifiable cell surface antigen that is expressed by a cancer of interest. In one embodiment, the cancer antigen is mesothelin, alphafetoprotein, CEA, CA-125, MUC-1, Her2Neu, ETA, NY-ESO-1, VEGF, VEGFR1, VEGFR2, PSMA, prostate specific antigen, HPV17E7, mutant p53, surviving, ras, MAGE, gp100, tyrosinase, WT1, PR1, folate-binding protein, CA-19-9, FAP, G250, or A33. In one embodiment, the antibody is specific for mesothelin. Fusion proteins that recognize and bind to mesothelin are described, for example, in U.S. Pat. No. 7,943,133, which is incorporated herein by reference in its entirety.

Fusion Proteins Targeting Mesothelin

In one embodiment, the target binding component is specific for mesothelin. MSLN is highly overexpressed on the surface of common epithelial cancers, including epithelial malignant mesothelioma and ovarian cancer, while expressed at relatively low levels only in mesothelial cells lining the pleura, pericardium, and peritoneum in healthy individuals.

In theory, fusion of anti-MSLN scFv and MtbHsp70 takes advantage of the immune-activating action of MtbHsp70 and the tumor-targeting activity of the scFv, which will yield anti-tumor responses against the broadest profile of tumor antigens.

In one embodiment, the fusion protein comprises a peptide having at least about 85% sequence homology to the peptide sequence of SEQ ID NO.: 1 or SEQ ID NO.: 2. In one embodiment, the fusion protein comprises a peptide having at least about 90% sequence homology to the peptide sequence of SEQ ID NO.: 1 or SEQ ID NO.: 2. In one embodiment, the fusion protein comprises a peptide having at least about 91% sequence homology to the peptide sequence of SEQ ID NO.: 1 or SEQ ID NO.: 2. In one embodiment, the fusion protein comprises a peptide having at least about 92% sequence homology to the peptide sequence of SEQ ID NO.: 1 or SEQ ID NO.: 2. In one embodiment, the fusion protein comprises a peptide having at least about 93% sequence homology to the peptide sequence of SEQ ID NO.: 1 or SEQ ID NO.: 2. In one embodiment, the fusion protein comprises a peptide having at least about 94% sequence homology to the peptide sequence of SEQ ID NO.: 1 or SEQ ID NO.: 2. In one embodiment, the fusion protein comprises a peptide having at least about 95% sequence homology to the peptide sequence of SEQ ID NO.: 1 or SEQ ID NO.: 2. In one embodiment, the fusion protein comprises a peptide having at least about 96% sequence homology to the peptide sequence of SEQ ID NO.: 1 or SEQ ID NO.: 2. In one embodiment, the fusion protein comprises a peptide having at least about 97% sequence homology to the peptide sequence of SEQ ID NO.: 1 or SEQ ID NO.: 2. In one embodiment, the fusion protein comprises a peptide having at least about 98% sequence homology to the peptide sequence of SEQ ID NO.: 1 or SEQ ID NO.: 2. In one embodiment, the fusion protein comprises a peptide having at least about 99% sequence homology to the peptide sequence of SEQ ID NO.: 1 or SEQ ID NO.: 2. In one embodiment, the fusion protein comprises a peptide having a sequence disclosed in PCT Application No. PCT/US2017/021911, incorporated by reference herein in its entirety, or a sequence having at least 85%, 90%, 91%, 92%, 93%, 94%, 95%, 96%, 97%, 98%, or 99% sequence homology to a sequence disclosed therein.

In one embodiment, the fusion protein retains the ability to bind a cancer antigen. In one embodiment, the fusion protein retains the ability to activate APCs. In one embodiment, the fusion protein retains the ability to facilitate production of activated APCs having cancer-specific antigens on the APC cell surface.

In one embodiment, the fusion protein comprises the peptide sequence of SEQ ID NO.: 1. In one embodiment, the fusion protein comprises the peptide sequence of SEQ ID NO.: 2.

Activated T Cells

In one aspect, this disclosure relates to methods of preparing activated, cancer-targeting T cells from APCs that were activated using a fusion protein as described herein.

In one embodiment, this invention relates to methods of preparing activated T cells, which comprises incubating T cells with activated antigen-presenting cells (APCs) for a period of time sufficient to produce activated T cells, wherein the APCs were prepared by incubating immune cells ex vivo in the presence of tumor cells and a fusion protein for a time period sufficient to produce the activated APCs, wherein at least one activated APC displays an antigen derived from the tumor cells. In one embodiment, the method further comprises isolating the activated T cells, wherein the isolated activated T cells are free or substantially free of the activated APCs, tumor cells and/or the fusion protein. In one embodiment, the APCs comprise dendritic cells.

The term "substantially free" as used with respect to the activated T cells refers to nearly complete removal of the APCs and/or tumor cells and/or fusion protein. In one embodiment, the activated T cells are free of the APCs and/or tumor cells and/or fusion protein. In one embodiment, the activated T cells are free of the tumor cells. In one embodiment, at least about 90%, at least about 91%, at least about 92%, at least about 93%, at least about 94%, at least about 95%, at least about 96%, at least about 97%, at least about 98%, at least about 99%, or at least about 99.9% of the tumor cells are removed from the activated T cells by isolation. In one embodiment, at least about 90%, at least about 91%, at least about 92%, at least about 93%, at least about 94%, at least about 95%, at least about 96%, at least about 97%, at least about 98%, at least about 99%, or at least about 99.9% of the fusion protein is removed from the activated T cells by isolation. In one embodiment, at least about 90%, at least about 91%, at least about 92%, at least about 93%, at least about 94%, at least about 95%, at least about 96%, at least about 97%, at least about 98%, at least about 99%, or at least about 99.9% of the APCs are removed from the activated T cells by isolation.

In one aspect, the fusion protein comprises an antigen-binding component and a heat shock protein component. While the antigen-binding component binds to the tumor cells, the heat shock protein component activates the APCs. In one embodiment, the antigen-binding component of the fusion protein may be any antibody or other molecule that recognizes a tumor or cancer cell of interest. In one embodiment, the antigen-binding component is a single chain antibody, a variable domain, or a fragment antigen-binding ("Fab") domain of an antibody.

In one aspect, the tumor cells are obtained from a patient.

In one aspect, the antigen-binding binding component is specific for a cancer antigen (e.g., a tumor-specific antigen or a tumor-associated antigen). The cancer antigen may be any identifiable cell surface antigen that is expressed by a cancer of interest. In one embodiment, the cancer antigen is mesothelin, alphafetoprotein, CEA, CA-125, MUC-1, Her2Neu, ETA, NY-ESO-1, VEGF, VEGFR1, VEGFR2, PSMA, prostate specific antigen, HPV17E7, mutant p53, surviving, ras, MAGE, gp100, tyrosinase, WT1, PR1, folate-binding protein, CA-19-9, FAP, G250, or A33. In one embodiment, the antibody is specific for mesothelin. Fusion proteins that recognize and bind to mesothelin are described, for example, in U.S. Pat. No. 7,943,133, which is incorporated herein by reference in its entirety.

In one embodiment, the antigen-presenting cells include, but are not limited to, dendritic cells, B lymphocytes, and mononuclear phagocytes. The mononuclear phagocytes may include monocytes and/or macrophages. In some aspects, the APCs comprise at least one CD40. In another aspect, the APCs are dendritic cells.

In one embodiment, the heat shock protein component includes but is not limited to HSP70 and/or an immune activating fragment and/or modified sequence thereof. In another aspect, the HSP70 or the immune activating fragment and/or modified sequence thereof is from *Mycobacterium tuberculosis*.

In one embodiment, this disclosure relates to a method for preparing activated T cells, the method comprising:

a) providing activated antigen-presenting cells that were activated in presence of tumor cells and a fusion protein ex vivo for a time period sufficient to produce activated antigen-presenting cells, wherein at least one activated antigen-presenting cell displays an antigen derived from the tumor cells;

b) contacting the activated antigen-presenting cells with T cells for a period of time sufficient to activate the T cells; and c) isolating the activated T cells; wherein the fusion protein comprises a tumor binding component and a heat shock protein component, wherein said tumor binding component binds to the tumor cells and said heat shock protein component activates antigen-presenting cells. In one embodiment, the isolated activated T cells are free or substantially free of the dendritic cells, tumor cells and the fusion protein.

In one embodiment, the heat shock protein component comprises HSP70 or an immune activating fragment and/or modified sequence thereof. In one embodiment, the HSP70 or the immune activating fragment and/or modified sequence thereof is from *Mycobacterium tuberculosis*. In one embodiment, the tumor binding component is a single chain antibody, a variable domain, or a Fab domain.

In one embodiment, the APCs were expanded in the presence of a growth factor. In one embodiment, the growth factor is a cytokine. In one embodiment, the growth factor is selected from the group consisting of Flt-3 ligand, GM-CSF, IL-4, M-CSF, IFNα, IL-1β, IL-4, IL-6, IL-13, IL-15 and TNFα.

In one embodiment, the tumor cells are obtained from a patient. In one embodiment, the tumor cells are derived from a patient to be treated as described herein. In one embodiment, the tumor cells are derived from a different patient. In one embodiment, the tumor cells comprise a cancer cell line.

In one embodiment, the term "tumor cells" that are incubated with the immune cells and fusion protein refers to any tumor sample, including but not limited to intact cells, viable cells, non-viable cells, tumor-specific antigen (e.g., isolated antigen, partially isolated antigen, recombinant antigen, etc.), and/or other cellular material derived from a tumor or cancer cell or cell line. In some embodiments, the tumor sample comprises at least a subset of antigens that are identical or similar to antigens associated with a patient's tumor, e.g., that will result in a T cell response against the patient's tumor.

In one embodiment, the isolated activated T cells are contacted with an effective amount of an anti-chemorepellant agent. In one embodiment, the anti-chemorepellant agent is any of the agents disclosed previously, e.g., selected from the group consisting of AMD3100 or a derivative thereof, AMD11070 (also called AMD070), AMD12118, AMD11814, AMD13073, FAMD3465, C131, BKT140, CTCE-9908, KRH-2731, TC14012, KRH-3955, BMS-936564/MDX-1338, LY2510924, GSK812397, KRH-1636, T-20, T-22, T-140, TE-14011, T-14012, TN14003, TAK-779, AK602, SCH-351125, tannic acid, NSC 651016, thalidomide, GF 109230X, an antibody that interferes with dimerization of a chemorepellant chemokine, and an antibody that interferes with dimerization of a receptor for a chemorepellant chemokine. In one embodiment, the anti-chemorepellant agent is AMD3100. In one embodiment, the amount of anti-chemorepellant agent is sufficient to bind to at least a subset of receptors, e.g., CXCR4 and/or CXCR7, on the surface of the T cells.

In one embodiment, the APCs are allogeneic, autologous, or derived from a cell line. In one embodiment, the T cells are allogeneic, autologous, or derived from a cell line. In one embodiment, the APCs and/or the T cells are isolated from a patient having cancer. In certain embodiments, the APCs and T cells are derived from the same source. e.g., the same patient.

In one embodiment, either the APCs or the tumor cells are immobilized on a solid support. In one embodiment, the activated APCs are isolated by isolating the solid support from the tumor cells and fusion protein.

In one embodiment, the T cells are immobilized on a solid support. In one embodiment, the activated T cells are isolated by isolating the solid support from the APCs.

In one embodiment, the solid support comprises a surface of a column, a sepharose bead, a gel, a matrix, a magnetic bead, or a plastic surface.

Methods of Treatment

The fusion protein as described herein can be used in combination with an anti-chemorepellant agent to treat a disease which is associated with a chemorepellant effect. In one embodiment, the disease is an abnormal cell or a tumor. In one embodiment, the disease is a cancer.

In one aspect, this invention relates to a method for treating a cancer, e.g., a tumor, in a patient wherein the cancer or tumor expresses chemorepellant properties, the method comprising administering to the patient: (a) an effective amount of APCs (e.g., dendritic cells) prepared by incubating the APCs with cancer or tumor cells and a fusion protein; and (b) concurrently administering to the patient an effective amount of an anti-chemorepellant agent; wherein the combination of the APCs and the anti-chemorepellant agent treat the cancer or tumor. In one embodiment, the fusion protein comprises a antigen (or target) binding component and a stress protein component, wherein the antigen (or target) binding component binds to the cancer or tumor and the stress protein component activates APCs (e.g., dendritic cells), leading to the generation of CD3 positive T cells that target cancer antigens.

In one embodiment, the anti-chemorepellant agent and the APCs (e.g., dendritic cells) are administered separately. In one embodiment, the anti-chemorepellant agent and the APCs (e.g., dendritic cells) are administered simultaneously. In one embodiment, the anti-chemorepellant agent and the APCs (e.g., dendritic cells) are administered sequentially.

In one embodiment, the anti-chemorepellant agent is administered prior to administration of the APCs (e.g., dendritic cells). In one embodiment, the anti-chemorepellant agent is administered after administration of the APCs (e.g., dendritic cells). In one embodiment, the anti-chemorepellant agent is administered before, during and/or after administration of the APCs (e.g., dendritic cells).

In some embodiments, the anti-chemorepellant agent is administered between one minute and 24 hours prior to administration of the APCs (e.g., dendritic cells). In some embodiments, the anti-chemorepellant agent is administered 1, 2, 3, 4, 5, 6, or 7 days prior to administration of the APCs (e.g., dendritic cells).

In some embodiments, the anti-chemorepellant agent is administered for a period of time sufficient to reduce or attenuate the chemorepellant effect of the tumor, e.g., such that the anti-chemorepellant agent has an anti-chemorepellant effect; the APCs (e.g., dendritic cells) can then be administered for a period of time during which the chemorepellant effect of the tumor is reduced or attenuated.

In some embodiments, the anti-chemorepellant agent is administered between one minute and 24 hours after administration of the APCs (e.g., dendritic cells). In some embodiments, the anti-chemorepellant agent is administered 1, 2, 3, 4, 5, 6, or 7 days after administration of the APCs (e.g., dendritic cells).

In one embodiment, the anti-chemorepellant agent and/or the APCs (e.g., dendritic cells) is administered intravenously, subcutaneously, orally, or intraperitoneally. In one embodiment, the anti-chemorepellant agent is administered proximal to (e.g., near or within the same body cavity as) the tumor. In one embodiment, the anti-chemorepellant agent is administered directly into the tumor or into a blood vessel feeding the tumor. In one embodiment, the anti-chemorepellant agent is administered systemically. In a further embodiment, the anti-chemorepellant agent is administered by microcatheter, an implanted device, or an implanted dosage form.

In one embodiment, the anti-chemorepellant agent is administered in a continuous manner for a defined period. In another embodiment, the anti-chemorepellant agent is administered in a pulsatile manner. For example, the anti-chemorepellant agent may be administered intermittently over a period of time.

Cancers or tumors that can be treated by the compounds and methods described herein include, but are not limited to: anal cancer, biliary tract cancer; brain cancer, including glioblastomas and medulloblastomas; breast cancer; cervical cancer; choriocarcinoma; colon cancer; endometrial cancer; esophageal cancer, gastric cancer; head and neck cancer, hematological neoplasms, including acute lymphocytic and myelogenous leukemia; multiple myeloma; AIDS associated leukemias and adult T cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; mesotheliomas, neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. In important embodiments, cancers or tumors escaping immune recognition include glioma, colon carcinoma, colorectal cancer, anal cancer, head and neck cancer, ovarian cancer, lymphoid cell-derived leukemia, choriocarcinoma, and melanoma. In one embodiment, the tumor cells derive from mesothelioma. In one embodiment, the tumor cells are from a hematological malignancy. In some embodiments, the cancer is a HPV-positive cancer.

In one embodiment, the term "tumor cells" refers to a tumor sample, including but not limited to intact cells, viable cells, non-viable cells, tumor-specific antigen (e.g., isolated antigen, partially isolated antigen, recombinant antigen, etc.), and/or other cellular material derived from a tumor or cancer cell.

In one embodiment, the cancer is a solid tumor. In one embodiment, the cancer is a leukemia. In one embodiment, the cancer over-expresses CXCL12, e.g., expresses an amount of CXCL12 in the tumor microenvironment sufficient to have a chemorepellant effect. In one embodiment, cancer expression of CXCL12 can be evaluated prior to administration of a composition as described herein. For example, a patient having a cancer that is determined to express or over-express CXCL12, e.g., a concentration of about 100 nM or higher, e.g., about 100, 150, 200, 250, 300, 350, 400, 450, or 500 nM, will be treated using a method and/or composition as described herein.

In one embodiment, the patient is also administered an effective amount of a fusion protein. The fusion protein may be administered before, at approximately the same time as, or after administration of the activated APCs and/or anti-chemorepellant agent. Dosages and routes of administration of the fusion protein are provided, for example in U.S. Pat. Nos. 8,143,387 and 7,943,133; U.S. Patent Pub. No. 20110129484; and U.S. Provisional Application No. 62/306,168; each of which is incorporated herein by reference in its entirety.

The activated T cells as described herein can be used to treat a cancer, cancer cell, or tumor in a patient that expresses an antigen recognized by the activated T cells.

The activated T cells as described herein can be used in combination with an anti chemorepellant agent to treat a cancer, cancer cell, or tumor which is associated with a chemorepellant effect. For example, the cancer cell, cancer, or tumor expresses an amount of a chemorepellant cytokine, e.g., CXCL12, e.g., at a level of about 100 nM or more, that is sufficient to repel or otherwise prevent access of immune cells to the cancer.

In one aspect, this invention relates to a method for treating a cancer, e.g., a tumor, in a patient, the method comprising administering to the patient: (a) an effective amount of APCs (e.g., dendritic cells) prepared by incubating the APCs with cancer or tumor cells and a fusion protein; and (b) concurrently administering to the patient an effective amount of an anti-chemorepellant agent; wherein the combination of the APCs and the anti-chemorepellant agent treat the cancer or tumor. In one embodiment, the fusion protein comprises an antigen-binding component and a stress protein component, wherein the antigen-binding component binds to the cancer or tumor and the stress protein component activates APCs (e.g., dendritic cells).

In one embodiment, the method comprises selecting a patient having a tumor that exhibits a chemorepellant effect. In one embodiment, the tumor overexpresses CXCL12.

In one embodiment, the anti-chemorepellant agent and the activated T cells are administered separately, e.g., by the same or different routes. In one embodiment, the anti-chemorepellant agent and the activated T cells are administered simultaneously, in the same or different compositions, e.g., by the same or different routes. In one embodiment, the anti-chemorepellant agent and the activated T cells are administered sequentially, e.g., by the same or different routes.

In one embodiment, the anti-chemorepellant agent is administered prior to administration of the activated T cells. In one embodiment, the anti-chemorepellant agent is administered after administration of the activated T cells. In one embodiment, the anti-chemorepellant agent is administered before, during and/or after administration of the activated T cells.

In some embodiments, the anti-chemorepellant agent is administered between one minute and 24 hours prior to administration of the activated T cells. In some embodiments, the anti-chemorepellant agent is administered 1, 2, 3, 4, 5, 6, or 7 days prior to administration of the activated T cells.

In some embodiments, the anti-chemorepellant agent is administered for a period of time sufficient to reduce or attenuate the chemorepellant effect of the tumor, e.g., such that the anti-chemorepellant agent has an anti-chemorepellant effect; the activated T cells can then be administered for a period of time during which the chemorepellant effect of the tumor is reduced or attenuated.

In some embodiments, the anti-chemorepellant agent is administered between one minute and 24 hours after administration of the activated T cells. In some embodiments, the anti-chemorepellant agent is administered 1, 2, 3, 4, 5, 6, or 7 days after administration of the activated T cells.

In one embodiment, the anti-chemorepellant agent and/or the activated T cells is administered intravenously, subcutaneously, orally, or intraperitoneally. In one embodiment, the anti-chemorepellant agent is administered proximal to (e.g., near or within the same body cavity as) the tumor. In one embodiment, the anti-chemorepellant agent is administered directly into the tumor or into a blood vessel feeding the tumor. In one embodiment, the anti-chemorepellant agent is administered systemically. In a further embodiment, the anti-chemorepellant agent is administered by microcatheter, an implanted device, or an implanted dosage form.

In one embodiment, the anti-chemorepellant agent is administered in a continuous manner for a defined period. In another embodiment, the anti-chemorepellant agent is administered in a pulsatile manner. For example, the anti-chemorepellant agent may be administered intermittently over a period of time.

Cancers or tumors that can be treated by the compounds and methods described herein include, but are not limited to: anal cancer, biliary tract cancer; brain cancer, including glioblastomas and medulloblastomas; breast cancer; cervical cancer; choriocarcinoma; colon cancer; endometrial cancer; esophageal cancer, gastric cancer; head and neck cancer, hematological neoplasms, including acute lymphocytic and myelogenous leukemia; multiple myeloma; AIDS associated leukemias and adult T cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; mesothelioma, neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. In important embodiments, cancers or tumors escaping immune recognition include glioma, colon carcinoma, colorectal cancer, anal cancer, head and neck cancer, ovarian cancer, lymphoid cell-derived leukemia, choriocarcinoma, and melanoma. In one embodiment, the tumor cells derive from mesothelioma. In one embodiment, the tumor cells are from a hematological malignancy. In one embodiment, the cancer is HPV-positive.

In one embodiment, the cancer is a solid tumor. In one embodiment, the cancer is a leukemia. In one embodiment, the caner over-expresses CXCL12. In one embodiment, cancer expression of CXCL12 can be evaluated prior to administration of a composition as described herein. For example, a patient having a cancer that is determined to express or over-express CXCL12 will be treated using a method and/or composition as described herein.

In one embodiment, the patient is also administered an effective amount of a fusion protein. The fusion protein may be administered before, at approximately the same time as, or after administration of the activated T cells and/or anti-chemorepellant agent. Dosages and routes of administration of the fusion protein are provided, for example in U.S. Pat. Nos. 8,143,387 and 7,943,133; U.S. Patent Pub. No. 20110129484; and PCT Application No. PCT/US2017/021911; each of which is incorporated herein by reference in its entirety.

Dose and Administration

The compositions, as described herein, are administered in effective amounts. The effective amount will depend upon the mode of administration, the particular condition being treated and the desired outcome. It will also depend upon, as discussed above, the stage of the condition, the age and physical condition of the subject, the nature of concurrent therapy, if any, and like factors well known to the medical practitioner. For therapeutic applications, it is that amount sufficient to achieve a medically desirable result.

Generally, the dose of the anti-chemorepellant agent of the present invention is from about 0.001 to about 100 mg/kg body weight per day, e.g., about 5 mg/kg body weight per day to about 50 mg/kg per day, e.g., about 5, 10, 15, 20, 25, 30, 35, 40, 45, or 50 mg/kg per day inclusive of all values and ranges therebetween, including endpoints. In one embodiment, the dose is from about 10 mg/kg to about 50 mg/kg per day. In one embodiment, the dose is from about 10 mg/kg to about 40 mg/kg per day. In one embodiment, the dose is from about 10 mg/kg to about 30 mg/kg per day. In one embodiment, the dose is from about 10 mg/kg to about 20 mg/kg per day. In one embodiment, the dose does not exceed about 50 mg/kg per day.

In one embodiment, the dose of the anti-chemorepellant agent is from about 50 mg/kg per week to about 350 mg/kg per week, inclusive of all values and ranges therebetween, including endpoints. In one embodiment, the dose of the anti-chemorepellant agent is about 50 mg/kg per week. In one embodiment, the dose of the anti-chemorepellant agent is about 60 mg/kg per week. In one embodiment, the dose of the anti-chemorepellant agent is about 70 mg/kg per week. In one embodiment, the dose of the anti-chemorepellant agent is about 80 mg/kg per week. In one embodiment, the dose of the anti-chemorepellant agent is about 90 mg/kg per week. In one embodiment, the dose of the anti-chemorepellant agent is about 100 mg/kg per week. In one embodiment, the dose of the anti-chemorepellant agent is about 110 mg/kg per week. In one embodiment, the dose of the anti-chemorepellant agent is about 120 mg/kg per week. In one embodiment, the dose of the anti-chemorepellant agent is about 130 mg/kg per week. In one embodiment, the dose of the anti-chemorepellant agent is about 140 mg/kg per week. In one embodiment, the dose of the anti-chemorepellant agent is about 150 mg/kg per week. In one embodiment, the dose of the anti-chemorepellant agent is about 160 mg/kg per week. In one embodiment, the dose of the anti-chemorepellant agent is about 170 mg/kg per week. In one embodiment, the dose of the anti-chemorepellant agent is about 180 mg/kg per week. In one embodiment, the dose of the anti-chemorepellant agent is about 190 mg/kg per week. In one embodiment, the dose of the anti-chemorepellant agent is about 200 mg/kg per week. In one embodiment, the dose of the anti-chemorepellant agent is about 210 mg/kg per week. In one embodiment, the dose of the anti-chemorepellant agent is about 220 mg/kg per week. In one embodiment, the dose of the anti-chemorepellant agent is about 230 mg/kg per week. In one embodiment, the dose of the anti-chemorepellant agent is about 240 mg/kg per week. In one embodiment, the dose of the anti-chemorepellant agent is about 250 mg/kg per week. In one embodiment, the dose of the anti-chemorepellant agent is about 260 mg/kg per week. In one embodiment, the dose of the anti-chemorepellant agent is about 270 mg/kg per week. In one embodiment, the dose of the anti-chemorepellant agent is about 280 mg/kg per week. In one embodiment, the dose of the anti-chemorepellant agent is about 290 mg/kg per week. In one embodiment, the dose of the anti-chemorepellant agent is about 300 mg/kg per week. In one embodiment, the dose of the anti-chemorepellant agent is about 310 mg/kg per week. In one embodiment, the dose of the anti-chemorepellant agent is about 320 mg/kg per week. In one embodiment, the dose of the anti-chemorepellant agent is about 330 mg/kg per week. In one embodiment, the dose of the anti-chemorepellant agent is about 340 mg/kg per week. In one embodiment, the dose of the anti-chemorepellant agent is about 350 mg/kg per week.

In one aspect of the invention, administration of the anti-chemorepellant agent is pulsatile. In one embodiment, an amount of anti-chemorepellant agent is administered every 1 hour to every 24 hours, for example every 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In one embodiment, an amount of anti-chemorepellant agent is administered every 1 day, 2 days, 3 days, 4 days, 5 days, 6 days, 7 days, 8 days, 9 days, or 10 days.

In one aspect of the invention, doses of the anti-chemorepellant agent are administered in a pulsatile manner for a period of time sufficient to have an anti-chemorepellant effect (e.g., to attenuate the chemorepellant effect of the tumor cell). In one embodiment, the period of time is between about 1 day and about 10 days. For example, the period of time may be 1 day, 2 days, 3 days, 4 days, 5 days, 6 days, 7 days, 8 days, 9 days, or 10 days. In some embodiments, the APCs or T cells are administered after the anti-chemorepellant effect has occurred, e.g., one or more days after the anti-chemorepellant agent has been administered. In some embodiments, administration of the chemorepellant agent is continued while the APCs or T cells are being administered.

A variety of administration routes are available. The methods of the invention, generally speaking, may be practiced using any mode of administration that is medically acceptable, meaning any mode that produces effective levels of the active compounds without causing clinically unacceptable adverse effects.

Modes of administration include oral, rectal, topical, nasal, intradermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule. When peptides are used therapeutically, in certain embodiments a desirable route of administration is by pulmonary aerosol. Techniques for preparing aerosol delivery systems containing peptides are well known to those of skill in the art. Generally, such systems should utilize components which will not significantly impair the biological properties of the antibodies, such as the paratope binding capacity (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing antibody or peptide aerosols without resort to undue experimentation.

Compositions suitable for oral administration may be presented as discrete units, such as capsules, tablets, lozenges, each containing a predetermined amount of the active agent(s). Other compositions include suspensions in aqueous liquids or non-aqueous liquids such as a syrup, elixir or an emulsion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed 25 oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In one embodiment, the anti-chemorepellant agent is administered parenterally. In one embodiment, the anti-chemorepellant agent is administered via microcatheter into a blood vessel proximal to a tumor. In one embodiment, the anti-chemorepellant agent is administered via microcatheter into a blood vessel within a tumor. In one embodiment, the anti-chemorepellant agent is administered subcutaneously. In one embodiment, the anti-chemorepellant agent is administered intradermally.

Other delivery systems can include time-release, delayed release or sustained release delivery systems. Such systems can avoid repeated administrations of the anti-chemorepellant agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and tri-glycerides; hydrogel release systems; sylastic systems; peptide based systems; wax coatings; compressed tablets using conventional binders and excipients; partially fused implants; and the like.

In one embodiment, the anti-chemorepellant agent or the APCs (e.g., dendritic cells) or activated T cells is administered in a time-release, delayed release or sustained release delivery system. In one embodiment, the time-release, delayed release or sustained release delivery system comprising the anti-chemorepellant agent or the APCs (e.g., dendritic cells) or activated T cells is inserted directly into the tumor. In one embodiment, the time-release, delayed release or sustained release delivery system comprising the anti-chemorepellant agent or the APCs (e.g., dendritic cells) or activated T cells is implanted in the patient proximal to the tumor. Additional implantable formulations are described, for example, in U.S. Patent App. Pub. No. 2008/0300165, which is incorporated herein by reference in its entirety.

In addition, important embodiments of the invention include pump-based hardware delivery systems, some of which are adapted for implantation. Such implantable pumps include controlled-release microchips. An exemplary controlled-release microchip is described in Santini, J T Jr. et al., Nature, 1999, 397:335-338, the contents of which are expressly incorporated herein by reference.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Pharmaceutical Compositions

In one aspect, this invention relates to a pharmaceutical composition comprising an anti-chemorepellant agent and APCs (e.g., dendritic cells) or activated T cells as described herein. In one embodiment, the APCs (e.g., dendritic cells) or T cells are derived from the patient to be treated. In one embodiment, the APCs (e.g., dendritic cells) or T cells express CXCR4 and/or CXCR7 on the cell surface.

In one embodiment, the composition further comprises a fusion protein as described herein.

In one embodiment, the composition comprises an effective amount of the fusion protein to activate the antigen-presenting cells. In one embodiment, the composition comprises an effective amount of the anti-chemorepellant agent to reduce the chemorepellant effect of the cancer. In one embodiment, the composition comprises an effective amount of the antigen presenting cells to result in activation of T cells against the cancer.

In one embodiment, the pharmaceutical composition is formulated for injection.

In one embodiment, the composition comprises a pharmaceutically acceptable excipient. Acceptable excipients are non-toxic, aid administration, and do not adversely affect the therapeutic benefit of the claimed compounds. Such excipient may be any solid, liquid, semi-solid or gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutical excipients and their formulations are described in Remington's Pharmaceutical Sciences, edited by E. W. Martin (Mack Publishing Company, 22nd ed., 2013).

In order to ensure that the dendritic cells and fusion protein interact once administered to a patient, the cells and protein may be combined prior to administration. In one embodiment, the cells and protein are combined immediately (e.g., seconds to one or two hours) prior to administration to the patient.

Without being bound by theory, it is believed that combination of the APCs or T cells and the anti-chemorepellant agent prior to administration to the patient will allow binding of the anti-chemorepellant agent to cell surface receptors (e.g., CXCR4 and/or CXCR7), thereby allowing the cells to overcome the chemorepellant effect of the tumor. In contrast, it is contemplated that the systemic delivery of an anti-chemorepellant agent results in indiscriminate binding of that agent to CXCR4 receptors and/or CXCR7 throughout the body.

In one embodiment, this invention relates to an ex vivo device or container comprising activated APCs and T cells as described herein. The device or container is preferably capable of being maintained under controlled, reproducible conditions such that the activated APCs and T cells can interact to activate the T cells. For example, the device or container may be, without limitation, a cell culture dish or plate, a bag (e.g., a culture bag), or any other device or container that is suitable for growing and/or maintaining cells; a tube or column; a bioreactor; etc.

Kit of Parts

In one aspect, this invention relates to a kit of parts for treatment of a disease, the kit comprising a fusion protein and an anti-chemorepellant agent.

In one embodiment is provided a kit of parts for treatment of a cancer, e.g., a tumor, in a patient, the kit comprising a therapeutically effective amount of an anti-chemorepellant agent and/or the APCs (e.g., dendritic cells) or activated T cells prepared by the methods described herein.

In one embodiment, the anti-chemorepellant agent is selected from the group consisting of AMD3100 or a derivative thereof, AMD11070 (also called AMD070), AMD12118, AMD11814, AMD13073, FAMD3465, C131, BKT140, CTCE-9908, KRH-2731, TC14012, KRH-3955, BMS-936564/MDX-1338, LY2510924, GSK812397, KRH-1636, T-20, T-22, T-140, TE-14011, T-14012, TN14003, TAK-779, AK602, SCH-351125, tannic acid, NSC 651016, thalidomide, GF 109230X, an antibody that interferes with dimerization of a chemorepellant chemokine, and an antibody that interferes with dimerization of a receptor for a chemorepellant chemokine. In one embodiment, the anti-chemorepellant agent is AMD3100 or a derivative thereof. In one embodiment, the anti-chemorepellant agent is AMD3100.

In one embodiment, the activated T cells and/or the anti-chemorepellant agent are formulated for injection.

In one embodiment, the activated T cells and the anti-chemorepellant agent are in the same formulation.

In one embodiment, the kit further comprises instructions for treating the cancer or tumor. In one embodiment, the kit of parts comprises instructions in a readable medium for dosing and/or administration of the anti-chemorepellant agent and the activated T cells.

The term "readable medium" as used herein refers to a representation of data that can be read, for example, by a human or by a machine. Non-limiting examples of human-readable formats include pamphlets, inserts, or other written forms. Non-limiting examples of machine-readable formats include any mechanism that provides (i.e., stores and/or transmits) information in a form readable by a machine (e.g., a computer, tablet, and/or smartphone). For example, a machine-readable medium includes read-only memory ("ROM"); random access memory ("RAM"); magnetic disk storage media; optical storage media; and flash memory devices. In one embodiment, the machine-readable medium is a CD-ROM. In one embodiment, the machine-readable medium is a USB drive. In one embodiment, the machine-readable medium is a Quick Response Code ("QR Code") or other matrix barcode.

EXAMPLES

Example 1. Construction of VIC-008 Fusion Protein

The fusion protein scFv-MtbHsp70 was constructed with VH and VL from anti-MSLN p4 scFv (Bergan L, et al. Development and in vitro validation of anti-mesothelin biobodies that prevent CA125/Mesothelin-dependent cell attachment. *Cancer Letters.* 2007; 255(2):263-74) fused to full length MtbHsp70 with a (G4S)3 linker in between, which has been shown in our previous study (Yuan J, et al. A novel mycobacterial Hsp70-containing fusion protein targeting mesothelin augments antitumor immunity and prolongs survival in murine models of ovarian cancer and mesothelioma. *Journal of Hematology & Oncology.* 2014; 7:15). The original fusion protein VIC-007, on which VIC-008 was based, achieved significant control of tumor growth and prolongation of the survival of tumor-bearing mice, but the antitumoral efficacy of the treatment regimen was not optimal. Antigenic peptides bind to MtbHsp70 through non-covalent interactions and can elicit both MHC class I-restricted CD8+ and MHC class II-restricted CD4+ T-cell responses. A new version of the scFv-MtbHsp70 fusion protein, VIC-008, was developed, which was modified from the original VIC-007 by the elimination of redundant amino acids and the introduction of a single amino acid mutation, phenylalanine (F) in place of valine (V), at position 381 of MtbHsp70 (FIG. 1). This change is designed to prevent peptide binding while retaining the immune-stimulatory capacity of the protein, in order to reduce the possibility that MtbHsp70 might incidentally bind and deliver other antigens that could result in off target effects or the induction of tolerance or autoimmunity.

The fusion proteins were constructed and expressed by WuXi App Tech (Shanghai, China) in CHO cells and provided at a purity of above 95% by HPLC and an endotoxin level of less than 1.0 EU/mg. VIC-008 is further described in Zeng Y., et al. (Improved Antitumoral Efficacy of Mesothelin Targeted Immune Activating Fusion Protein in Murine Model of Ovarian Cancer. Int J Cancer Clin Res 2016; 3:05) and U.S. Provisional Application No. 62/306,168, each of which is incorporated herein by reference in its entirety.

Example 2. VIC-008 Enhances Control of Tumor Growth

Ovarian cancer was established by intraperitoneal (i.p.) injection of syngeneic cancer cells, Luc-ID8 ($5\times10^6$ cells per mouse), into 6-week-old female C57BL/6 mice. All mice were purchased from Jackson laboratories. Mice were observed daily for 1 week after inoculation of tumor cells. Tumor generations were consistently first evident via abdominal distension secondary to malignant ascites, and tumor-bearing mice were euthanized at the endpoint when there were signs of distress, including fur ruffling, rapid respiratory rate, hunched posture, reduced activity, and progressive ascites formation.

Mice with ovarian tumors were treated 7 days after tumor cell inoculation with i.p. injections of VIC-007 (4 µg per mouse), VIC-008 (4 µg per mouse), or normal saline. This was followed by 3 further treatments at 7-day intervals.

Intraperitoneal tumor growth was monitored weekly after tumor cell inoculation using in vivo live imaging by IVIS Spectrum (PerkinElmer). Mice were injected intraperitoneally with 150 mg/kg body weight of D-luciferin 10 min in advance and subsequently imaged by IVIS Spectrum.

Figure 2B:
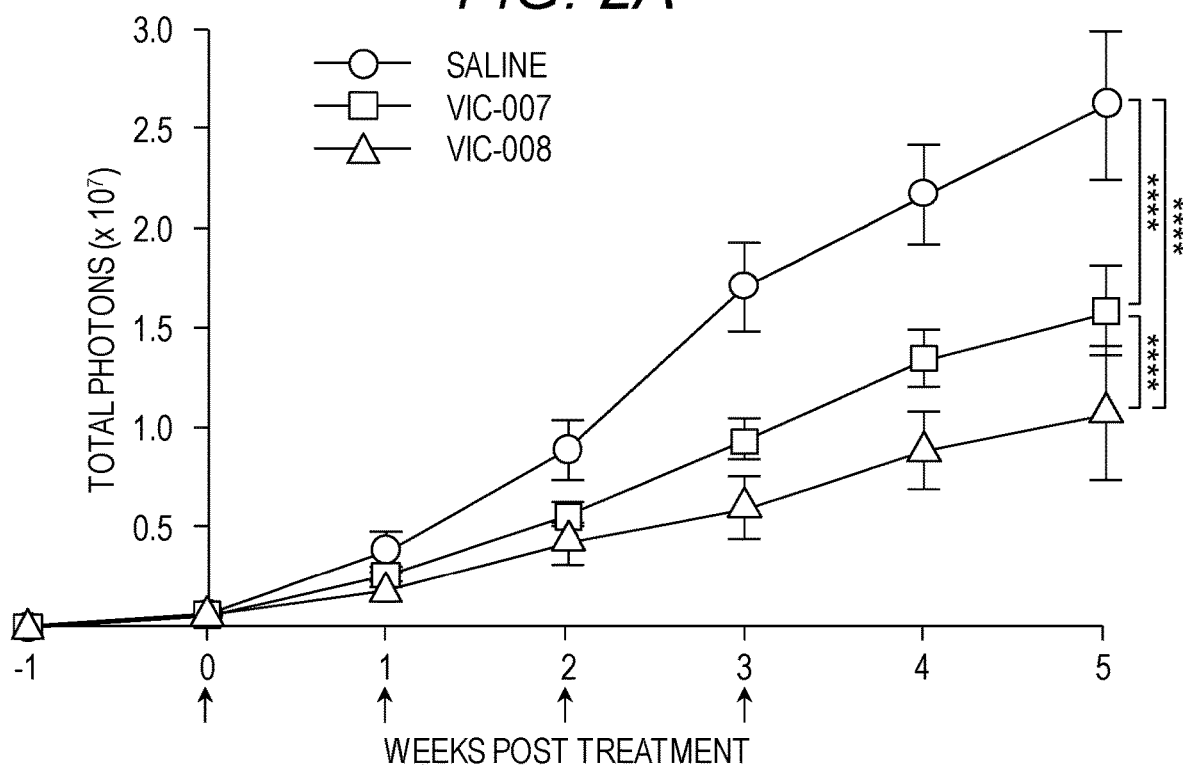
FIG. 2B is a graphical representation of the tumor growth shown in FIG. 2A.

As shown in FIG. 2, both VIC-007 and VIC-008 significantly slowed tumor growth as recorded by bioluminescence signals compared to saline ($p<0.0001$ and $p<0.0001$) while VIC-008 further significantly delayed tumor growth compared to VIC-007 ($p<0.0001$). Statistical differences between three or more experimental groups were analyzed using Two-Way ANOVA, followed by Tukey's multiple comparison tests when mean of each group is compared with that of every other group.

Example 3. VIC-008 Enhances the Prolongation of Mouse Survival

The efficacy of VIC-007 and VIC-008 to prolong survival in the tumor-bearing mice was evaluated in the mice treated as described in Example 2.

Figure 3:
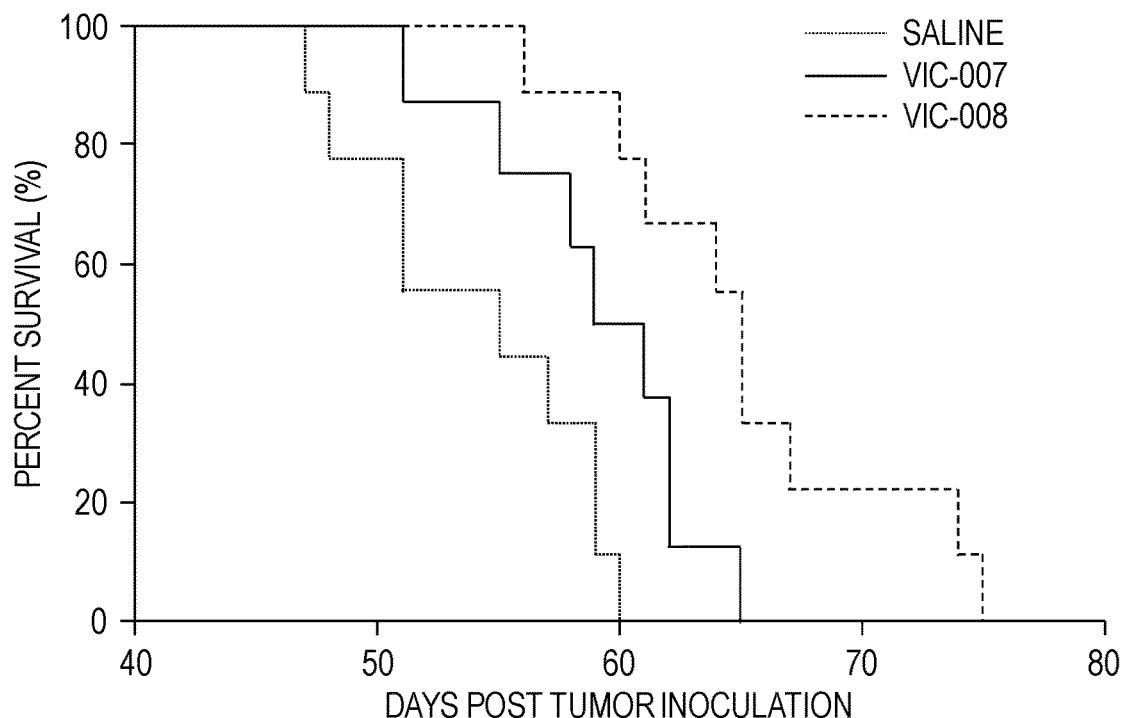
FIG. 3 shows percent survival of the mice inoculated with ovarian cancer cells, after administration of saline, VIC-007, or VIC-008.

As shown in FIG. 3, both VIC-007 and VIC-008 significantly enhanced the survival of tumor-bearing mice compared to saline ($p=0.0253$ and $p=0.0002$), with increased median survival of 55 days from saline to 60 days from VIC-007 and further to 65 days from VIC-008. VIC-008 further significantly prolonged the survival of the tumor-bearing mice compared to VIC-007 ($p=0.0301$). Survival was analyzed with the Log-rank test.

Taken together, these data showed that the new version of the fusion protein VIC-008 significantly delayed the tumor growth and prolonged the survival in a syngeneic murine model of ovarian cancer. Improved mouse survival of VIC-008 compared to VIC-007 is likely related to the changes made to the protein sequences.

Figure 4:
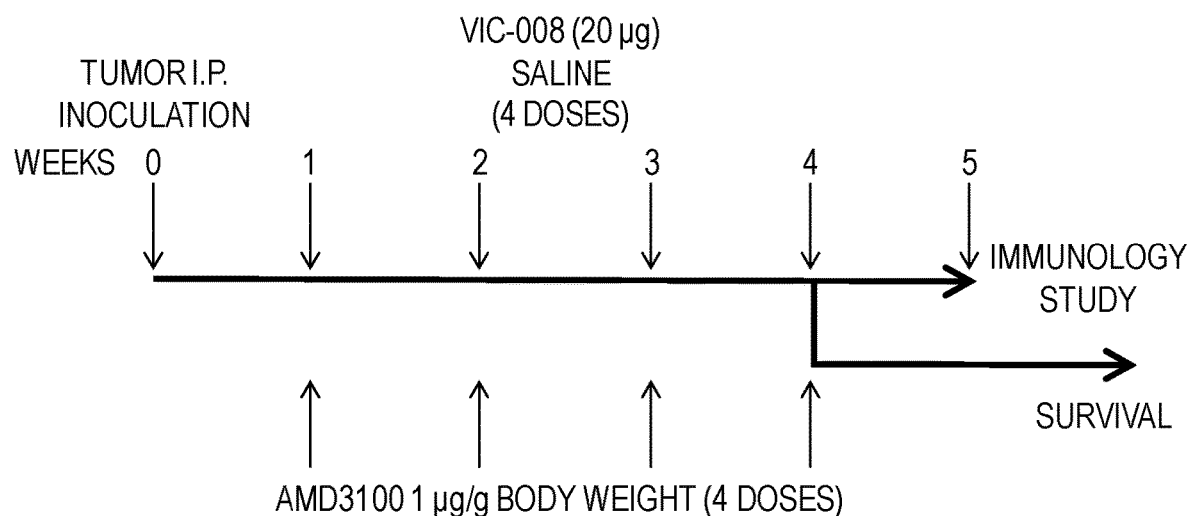
FIG. 4 shows the treatment protocol for tumor inoculation (mesothelioma) followed by administration of saline, VIC-008 alone, AMD3100 alone, or VIC-008 with AMD3100.

Example 4. Combination Treatment of VIC-008 with AMD3100 Further Prolongs Mouse Survival Mesothelioma tumor was established by i.p. injection of cancer cells, Luc-40L or Luc-AE17, into C57BL/6 mice. One week later, saline, VIC-008 (20 µg), and/or AMD3100 (1 µg/g body weight) were administered once a week for four weeks, as indicated in FIG. 4.

Figure 5:
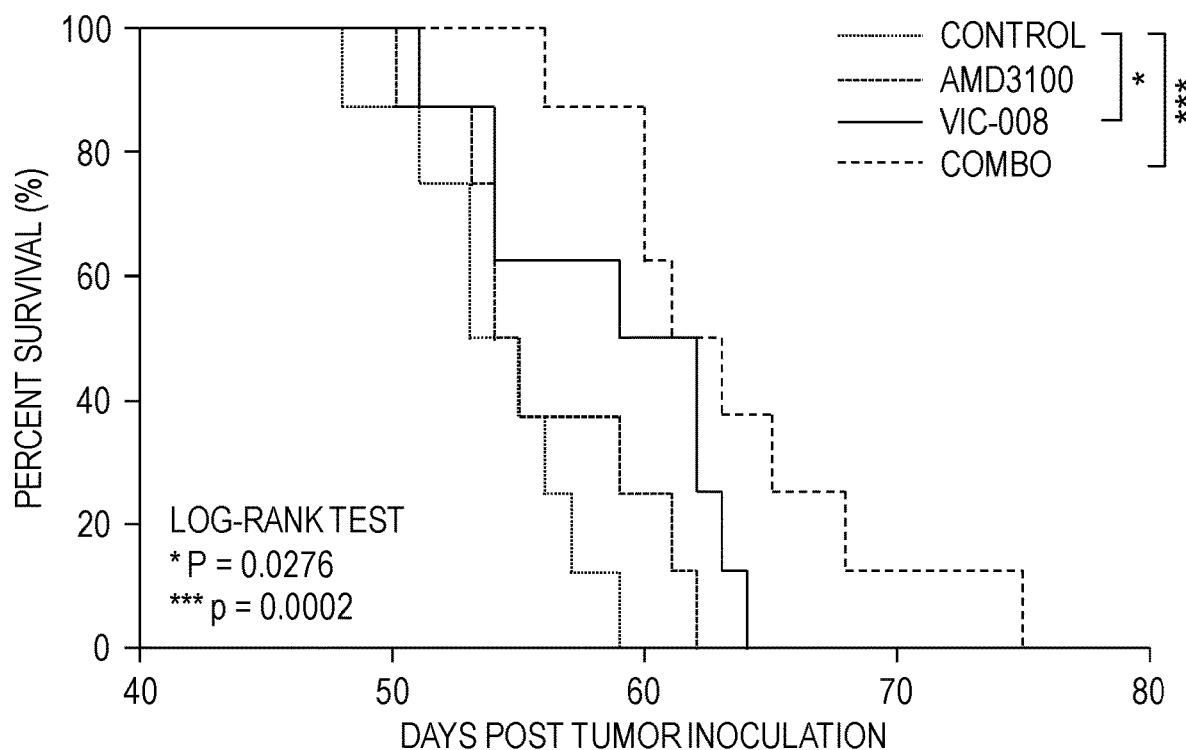
FIG. 5 shows percent survival of the mice inoculated with mesothelioma cancer cells, Luc-40L, after administration of saline, VIC-008 alone, AMD3100 alone, or VIC-008 with AMD3100.
Figure 6:
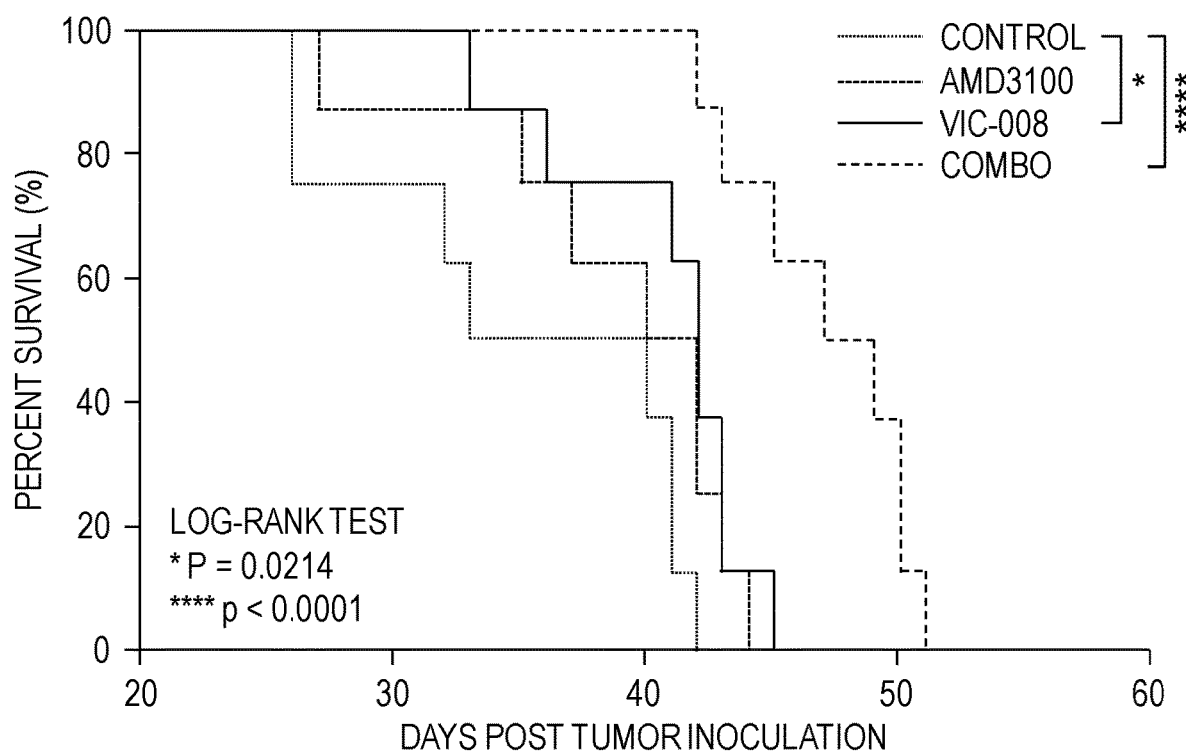
FIG. 6 shows percent survival of the mice inoculated with mesothelioma cancer cells, Luc-AE17, after administration of saline, VIC-008 alone, AMD3100 alone, or VIC-008 with AMD3100.

As shown in FIG. 5 (Luc-40L), VIC-008 significantly enhanced the survival of tumor-bearing mice compared to saline ($p=0.0214$), while the combination of VIC-008 and AMD3100 further enhanced survival ($p<0.0001$ versus saline). Similar results were observed with Luc-AE17 (FIG. 6). AMD3100 had a slight effect on survival, but this effect did not reach significance in this study.

These data show that VIC-008 alone is able to prolong survival in both models of mesothelioma, and AMD3100 alone slightly benefits survival. Combination treatment with VIC-008 and AMD3100 significantly suppresses mesothelioma proliferation and prolongs survival of mice with mesothelioma tumors.

Example 5. Combination Treatment of VIC-008 with AMD3100 For Mesothelioma

Materials and Methods
Reagents

The fusion proteins were constructed as described above and expressed by WuXi Biologics (Shanghai, China) in CHO cells and provided at a purity of above 95% by HPLC and an endotoxin level of less than 1.0 EU/mg. AMD3100 was purchased from Abcam (#ab120718).

Tumor Cells 40L and AE17 mouse mesothelioma cell lines were kind gifts from Dr. Agnes Kane in Department of Pathology and Laboratory Medicine at Brown University. Cells were cultured at 37° C. in DMEM supplemented with 1% L-glutamine, 1% penicillin-streptomycin, and 10% fetal bovine serum.

Animal Models

Five-week-old female C57BL/6 mice were obtained from the Jackson Laboratory and maintained in the gnotobiotic animal facility of Massachusetts General Hospital (MGH) in compliance with institutional guidelines and policies. After one week acclimatization, tumors were initiated with $4 \times 10^6$ 40L cells or $2 \times 10^6$ AE17 cells per mouse administered intraperitoneally (i.p.). A subset of the mice from each group were euthanized with i.p. administration of Ketamine (9 mg/ml in saline) and Xylazine (0.9 mg/ml in saline) 7 days after the last treatment, and samples harvested for immune profiling of tumors, lymph nodes and spleens. The remaining animals in each group were monitored for survival. For survival studies, the mice were observed daily after inoculation of tumor cells. Tumor generation was consistently first evident via the appearance of abdominal distension secondary to malignant ascites, and tumor-bearing mice were euthanized at the endpoint when there were signs of distress, including fur ruffling, rapid respiratory rate, hunched posture, reduced activity, and progressive ascites formation.

Splenocytes from transgenic T-Red/FoxP3 GFP mice were used as a source of fluorescently tagged $T_g$ cells by cell sorting as described below. T-Red/FoxP3 GFP mice are a fully backcrossed C57BL/6 line of transgenic mice that produced by crossing T-red mice with FoxP3 GFP mice. T-red mice express dsRedII under the control of the CD4 promoter modified to lack the negative control element thereby allowing expression in both $CD4^+$ and $CD8^+$ T cells. In FoxP3 GFP mice, GFP is expressed from under control of the FoxP3 promoter with internal deletions to FoxP3 to prevent over expression. All animal studies were approved by the Institutional Animal Care and Use Committee of MGH.

Treatment

Beginning seven days after tumor inoculation, treatments were administrated by i.p. injection once a week for four successive weeks. VIC-008 was administrated i.p. at 20 μg in 100 μl of saline per mouse once a week and AMD3100 was given once a week by i.p. injection at 1 mg/kg of body weight in 100 μl of saline.

Immune Profiling by Flow Cytometry

Tumors were mechanically disaggregated using sterile razor blades and digested at 37° C. for 2 hours in RPMI 1640 with collagenase type IV for 40L tumors or type I for AE17 tumors (2 mg/ml, Sigma), DNase (0.1 mg/ml, Sigma), hyaluronidase (0.1 mg/ml, Sigma), and BSA (2 mg/ml, Sigma). Cell suspensions were passed through 100 μm filters to remove aggregates. Lymph nodes and spleens were mashed and filtered through 40 μm strainers. Cells were washed with staining buffer (#420201, Biolegend) and stained with the conjugated antibodies for surface markers. Total live cells were determined by LIVE/DEAD® staining (ThermoFisher, #L23105).

For intracellular cytokine detection, after staining of surface markers, cells were fixed and permeabilized with fixation/permeabilization reagents from BioLegend (#424401) or eBioscience (#00-5521-00) and stained with the conjugated antibodies for intracellular markers.

Conjugated antibodies from eBioscience were as follows: CD40L (clone MR1), and PD-1 (clone J43). The following conjugated antibodies were purchased from BioLegend: CD3 (clone 17A2), CD4 (clone GK1.5), CD8a (clone 53-6.7), Foxp3 (clone MF-14), IL-2 (clone JES6-5H4), and IFN-γ (clone XMG1.2). CD25 (clone PC61) antibody was from BD Biosciences.

Flow cytometric analyses were performed using BD LSR-Fortessa X-20 (BD Biosciences). Gating strategies were determined by the Fluorescence Minus One. Flow data were analyzed by FlowJo V10 (TreeStar).

Ex-Vivo Culturing of Splenocytes and Cytokine Detection

The splenocytes were harvested from mashed spleens, filtered through 40 μm cell strainers and treated with red blood cell lysis buffer. $2 \times 10^6$ splenocytes were placed per well in 24-well plates in RPMI 1640 medium supplemented with L-glutamine and stimulated with 2 μg/ml of recombinant mouse mesothelin (BioLegend, #594006) for 72 hours. Brefeldin A and Monesin (BioLegend, #420601 and #420701) were added into the culture medium during the last five hours. Splenocytes were then harvested and intracellular cytokine staining performed using the corresponding antibodies for cytometric analysis.

In vitro Reprogramming of $T_{reg}$ Cells rGH-ffLuc-eGFP transgenic mice express Green Fluorescent Protein (GFP) in $Foxp3^+$ $T_{reg}$ cells. Spleens were collected from these mice and mashed and filtered through 40 μm strainers. Cells expressing GFP-Foxp3 from $CD4^+$ splenocytes were sorted on a FACSAria (BD Biosciences) and then exposed to AMD3100 (5 μg/ml) in the presence or absence of anti-CD3/CD28 antibody (1 μg/ml) for 24 hours. Brefeldin A and Monesin (BioLegend, #420601 and #420701) were added into the culture medium during the last five hours. The cells were then harvested and stained with the conjugated antibodies specific for CD3, CD4, CD25, Foxp3, IL-2 and CD40L, and analyzed by flow cytometry.

Statistical Analyses

P values were calculated by GraphPad Prism 6. Unless described otherwise, the P values for comparison among groups were obtained by One-way ANOVA with Dunnett's multiple comparisons test or unpaired t-test with Welch's correction. The Kaplan-Meier method and log-rank test were used to compare survival among groups. $P<0.05$ is considered statistically significant. Data are presented as mean±SEM.

Results

Figure 7A:
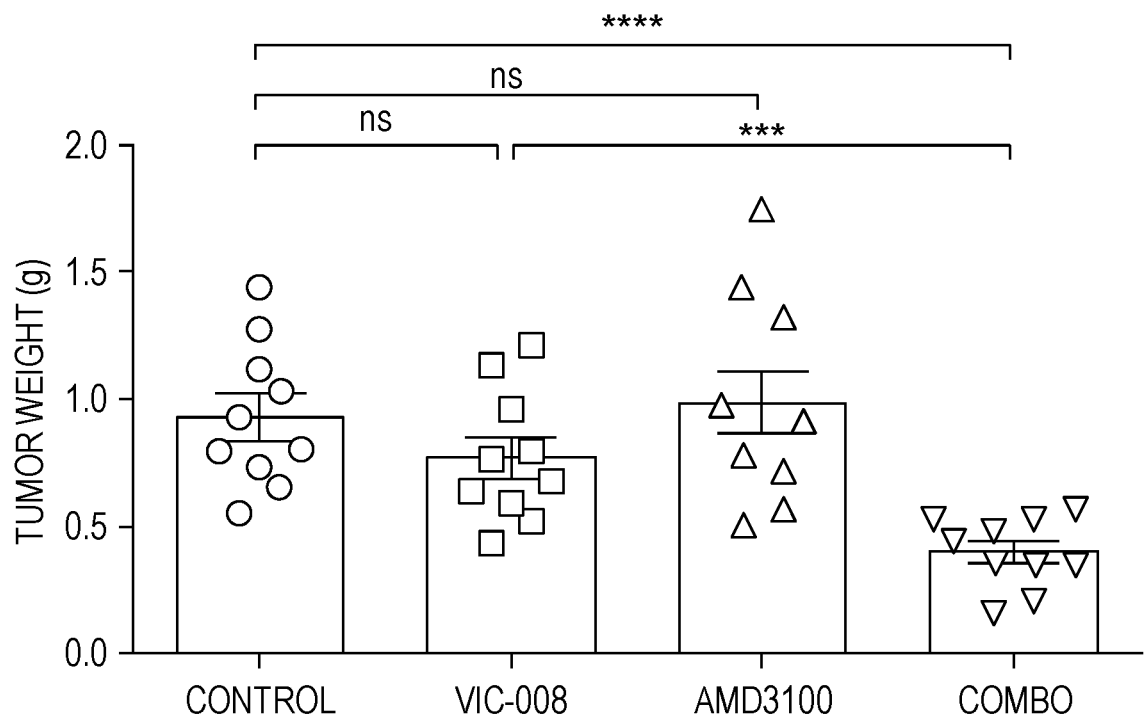
FIGS. 7A-7D show tumor growth and mice survival in different treatment groups. All the intraperitoneal tumors were collected at day 7 after the last treatment and weighed in 40L (n=10) (A) and AE17 (n=10) (B) mice. The survival of 40L (n=12) (C) and AE17 (n=12) (D) tumor bearing mice. Numbers on X axis represented days of mouse survival after inoculation of tumor cells into mice. NS, not significant, *P<0.05,P<0.01, *P<0.001 and ****P<0.0001. Data were presented as mean±SEM.
Figure 7B:
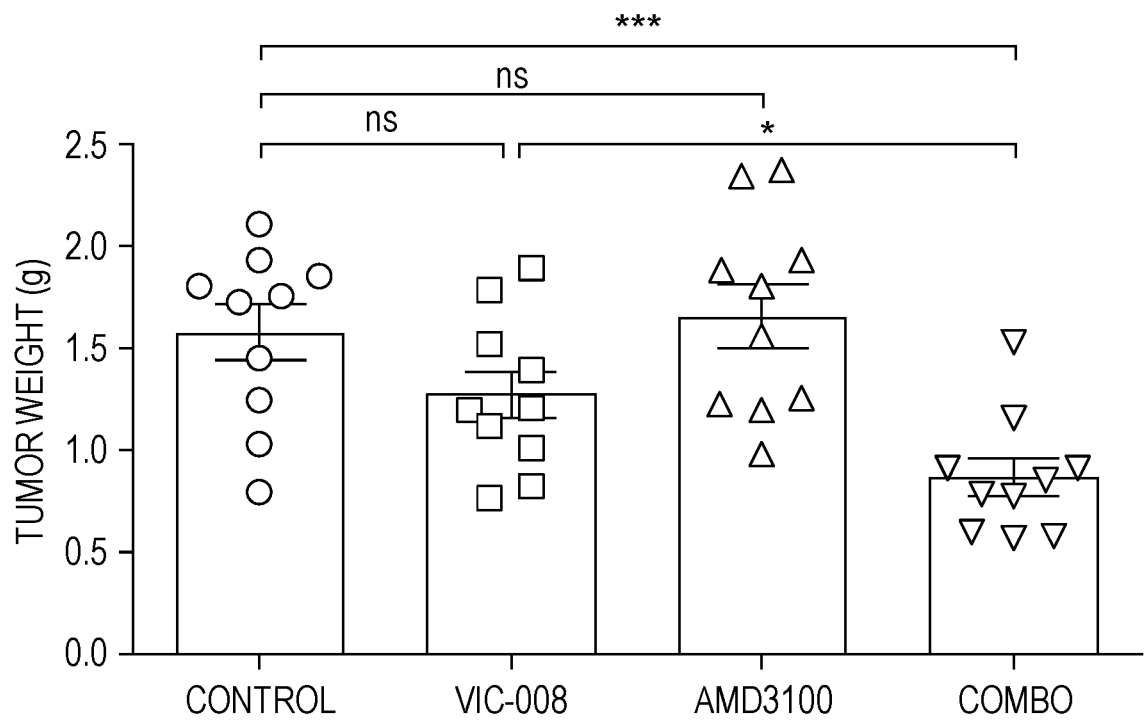
Figure 7C:
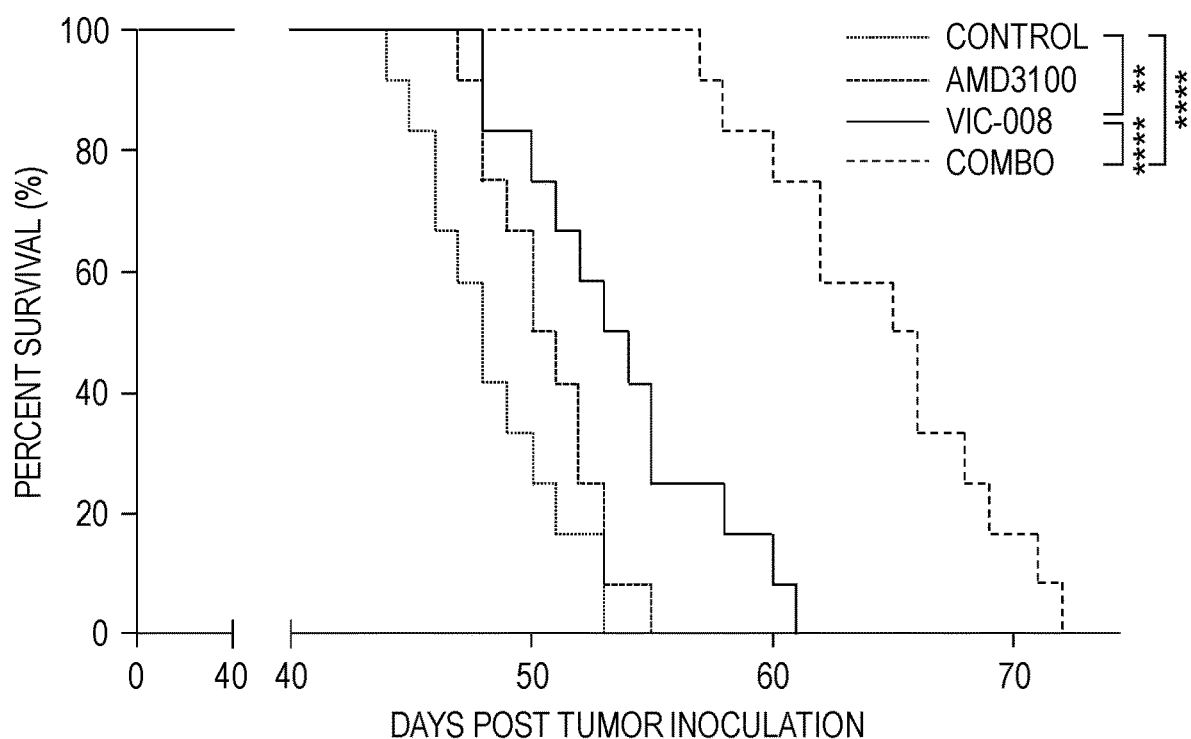
Figure 7D:
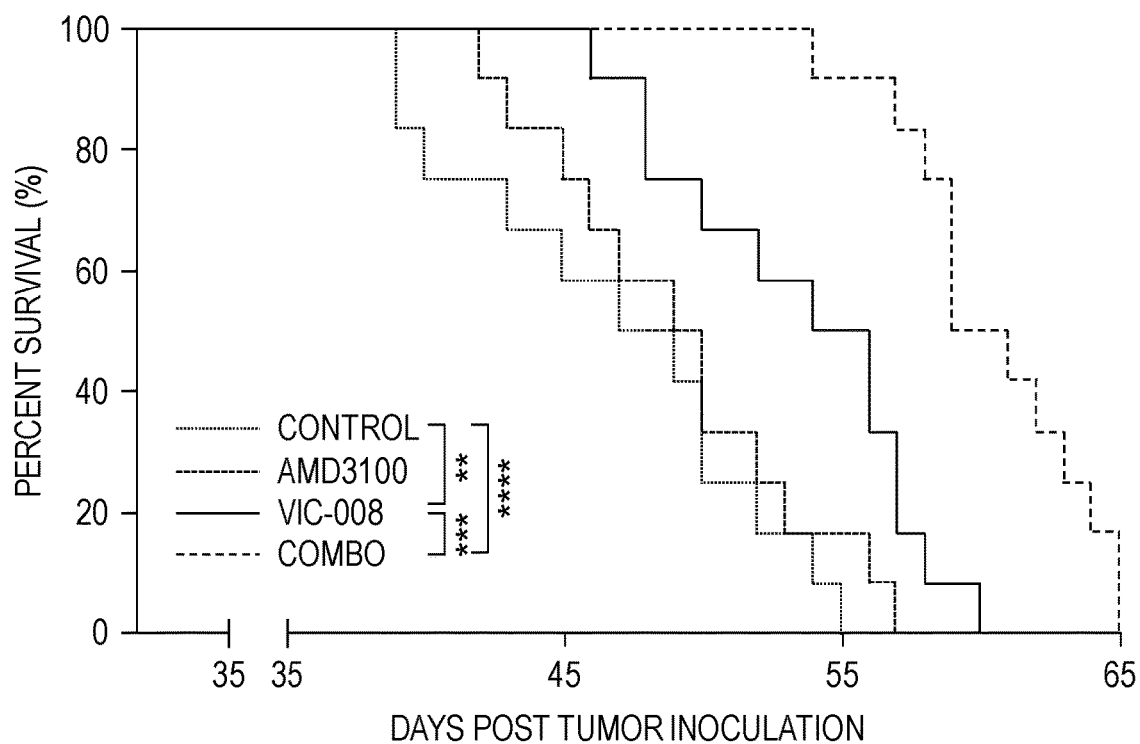

Combination Therapy with AMD3100 and VIC-008 Augments Tumor Control and Mouse Survival Two intraperitoneal malignant mesothelioma models were established in immunocompetent C57BL/6 mice, separately using the syngeneic 40L and AE17 cell lines. Here, the effect of AMD3100 and VIC-008 was tested, used singly or in combination, on tumor growth and animal survival in mesothelioma-bearing mice. In animals treated with VIC-008 alone (20 μg per mouse), the total weight of intraperitoneal tumors collected one week after the last treatment was generally reduced (FIGS. 7A-7B) and animal survival was significantly prolonged (FIGS. 7C-7D) compared to saline control treatment in both the 40L and AE17 models (P<0.01 and P<0.01, respectively). AMD3100 alone at 1 mg/kg of mouse body weight conferred only modest benefit to survival in both 40L and AE17 mouse MM models compared to saline control treatment. However, the combination treatment with VIC-008 and AMD3100 significantly enhanced tumor control (P<0.0001 and P<0.001, respectively) and prolonged animal survival (P<0.0001 and P<0.0001, respectively) compared to saline control in both 40L and AE17 models. Moreover, the combination treatment showed further significantly improved antitumor efficacy on inhibition of tumor growth (P<0.001 and P<0.05, respectively) and prolongation of mouse survival (P<0.0001 and P<0.001, respectively) compared to VIC-008 monotherapy in both 40L and AE17 models. These data indicate that when combined, AMD3100 significantly enhances the antitumor effect of VIC-008 in both 40L and AE17 MM mouse models compared to monotherapy with either agent.

VIC-008 Increases Lymphocyte Infiltration in Spleens, Lymph Nodes and Tumors

Figure 8A:
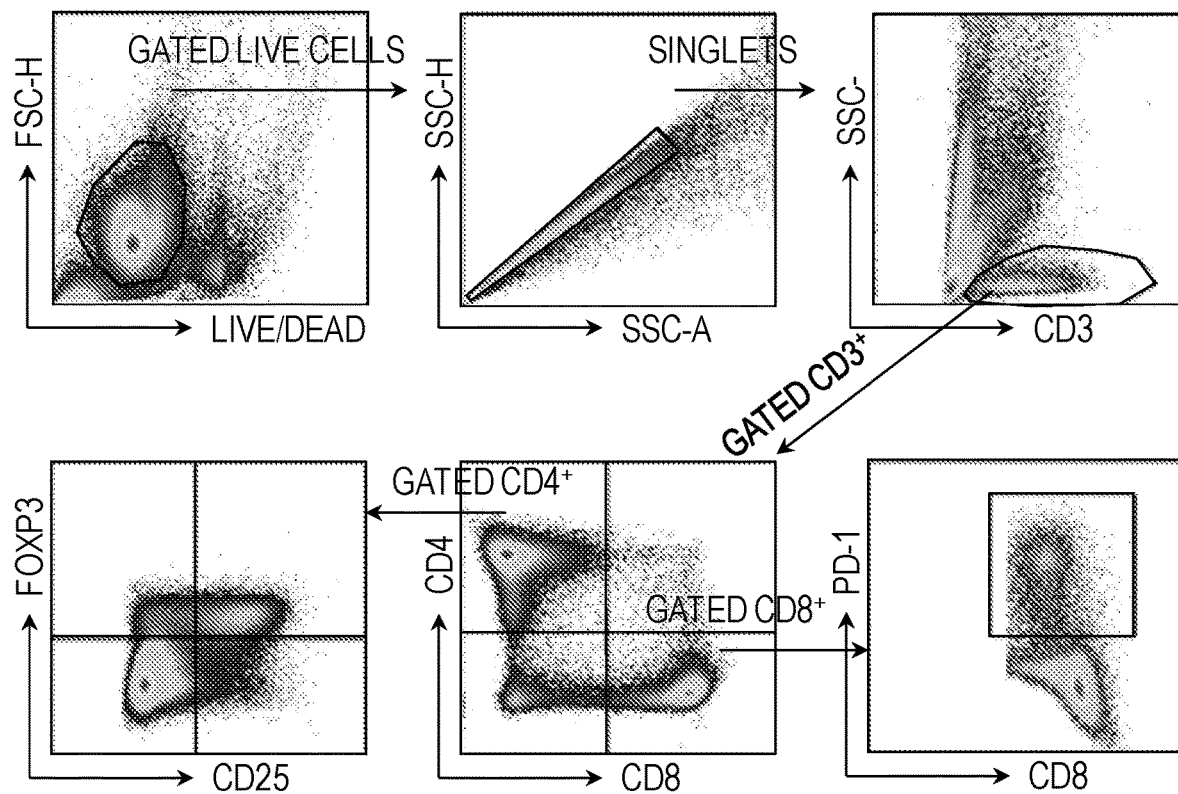
FIGS. 8A-8F show VIC-008 facilitates lymphocyte infiltration. (A) Gating strategy for infiltrated lymphocytes. The proportion of CD8$^+$ T cells in total live splenocytes in 40L (n=6) (B) and AE17 (n=5) (C) mice. The proportion of CD8$^+$ T cells in total live cells in lymph nodes of AE17 mice (n=5) (D). The proportion of CD8$^+$ T cells in total live cells in tumors of 40L (n=6) (E) and AE17 (n=5) (F) mice. *P<0.05, P<0.01 and *P<0.001. Data are presented as mean±SEM.
Figure 8B:
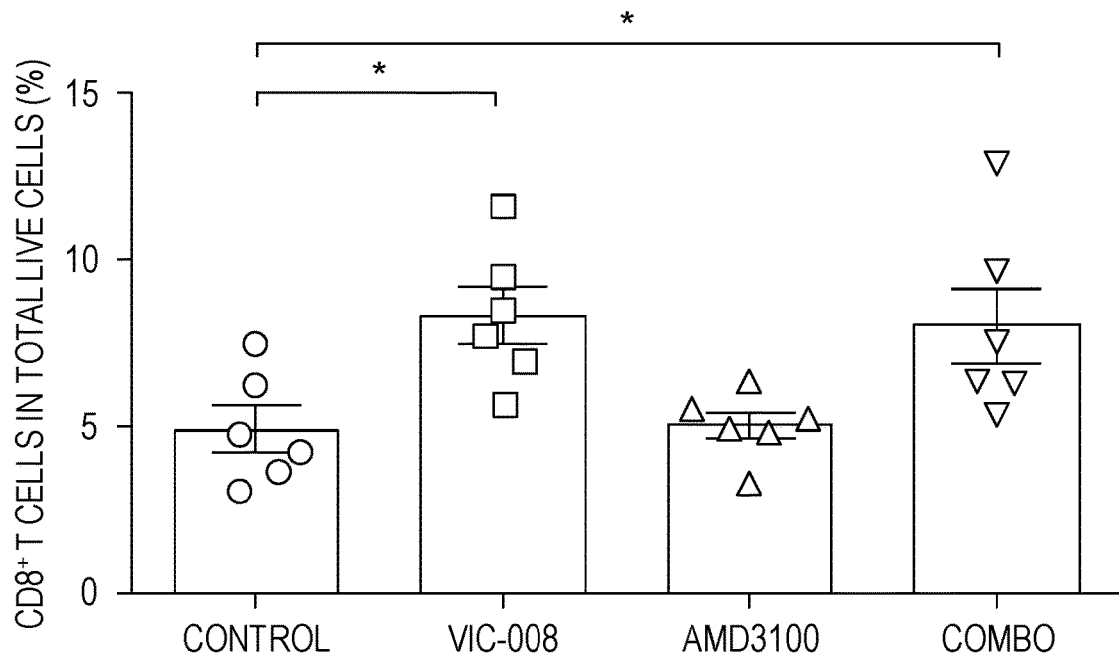
Figure 8C:
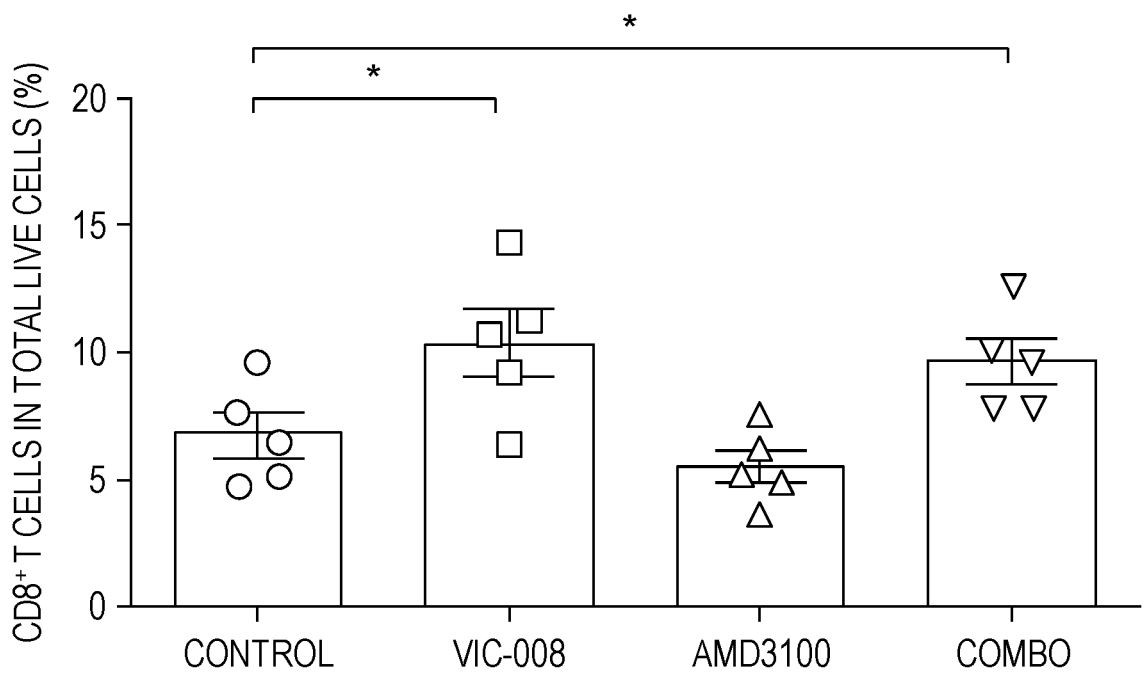
Figure 8D:
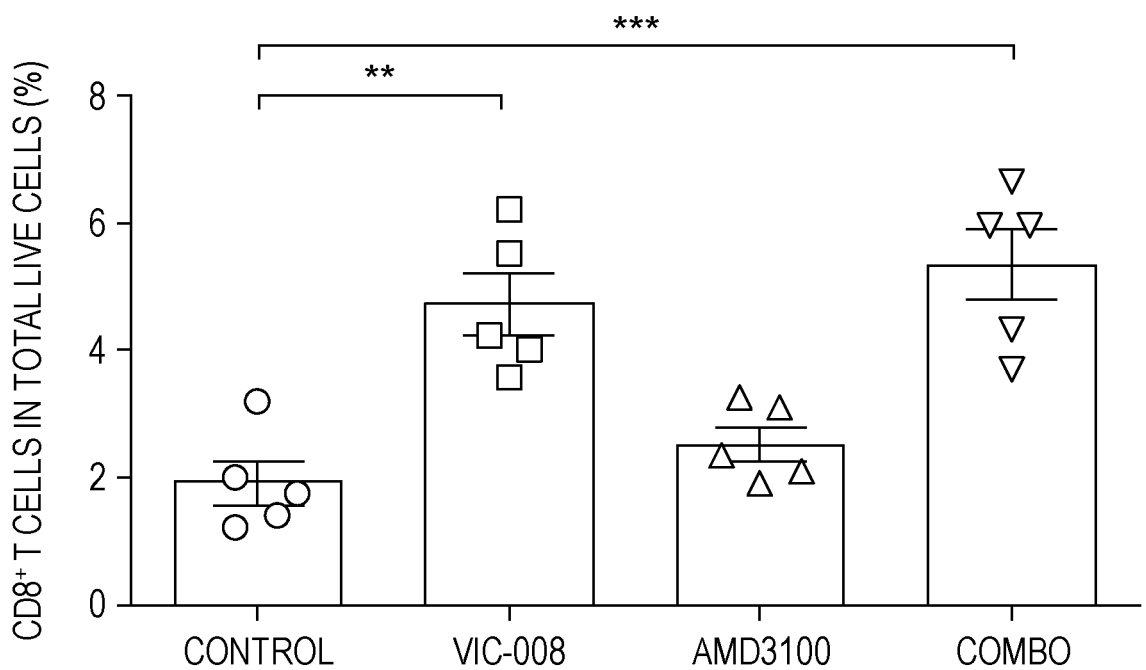
Figure 8E:
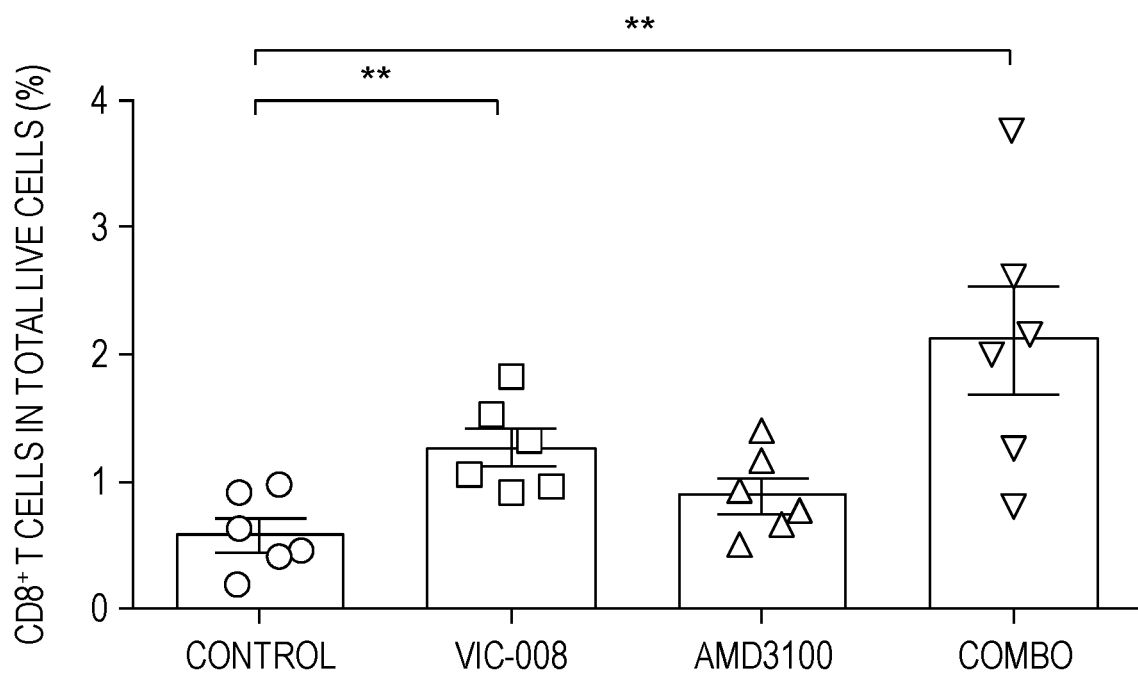
Figure 8F:
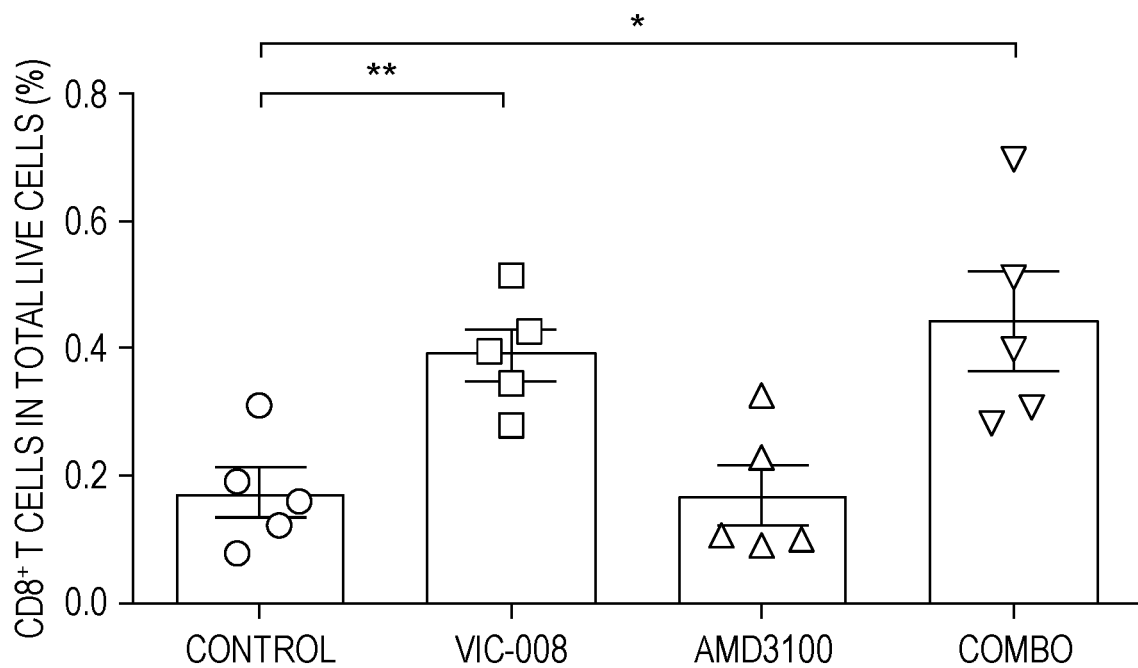
Figure 9A:
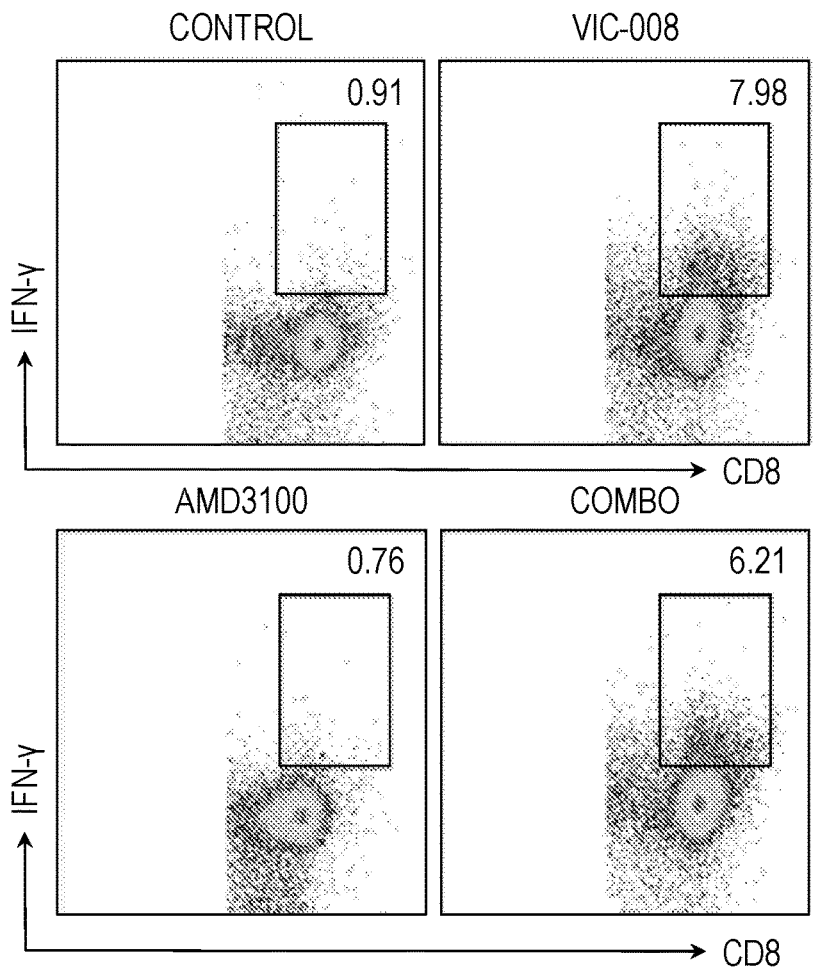
FIGS. 9A-9D show VIC-008 promoted CD8$^+$ T-cell IFN-γ secretion. (A) Representative dot plots of IFN-γ secreting cells in different treatment groups. The proportion of IFN-γ secreting cells in CD8$^+$ T cells in spleens of 40L (n=6) (B) and AE17 (n=5) (C) mice. The proportion of IFN-γ secreting cells in CD8$^+$ T cells in lymph nodes of AE17 mice (n=5) (D). P<0.01 and *P<0.001. Data are presented as mean±SEM.
Figure 9B:
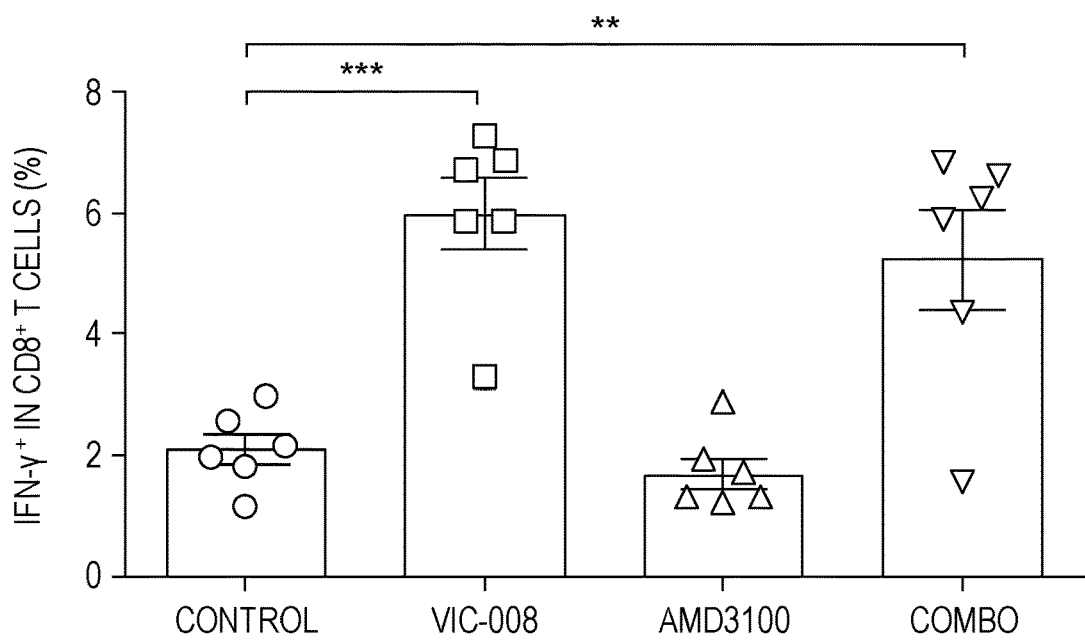
Figure 9C:
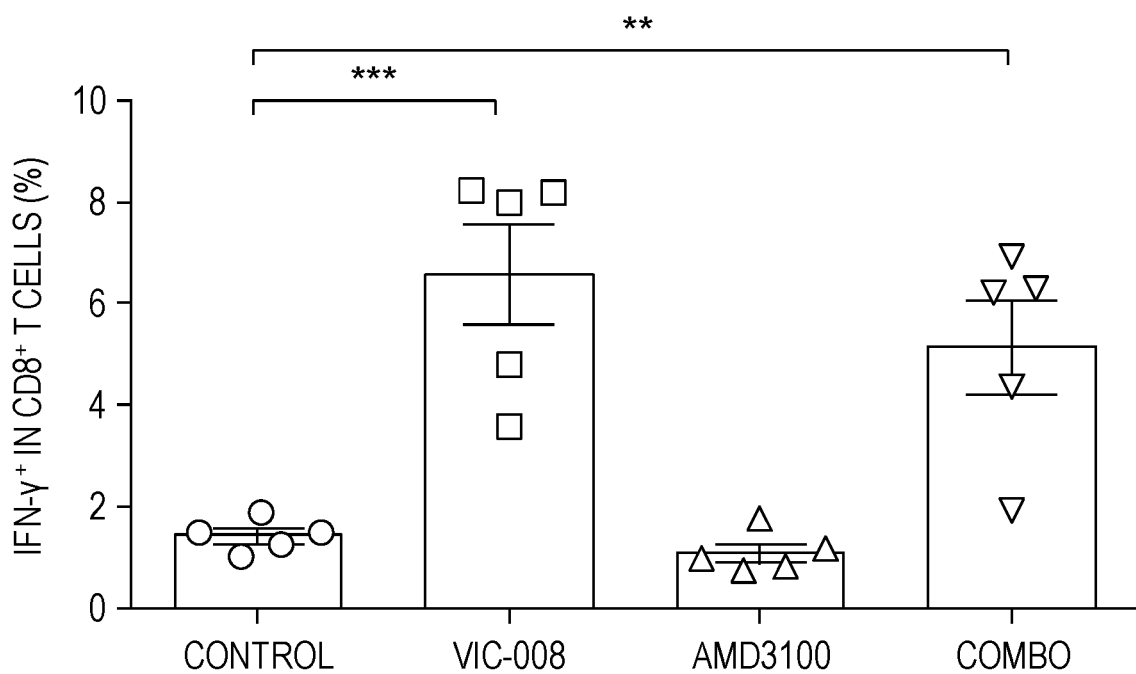
Figure 9D:
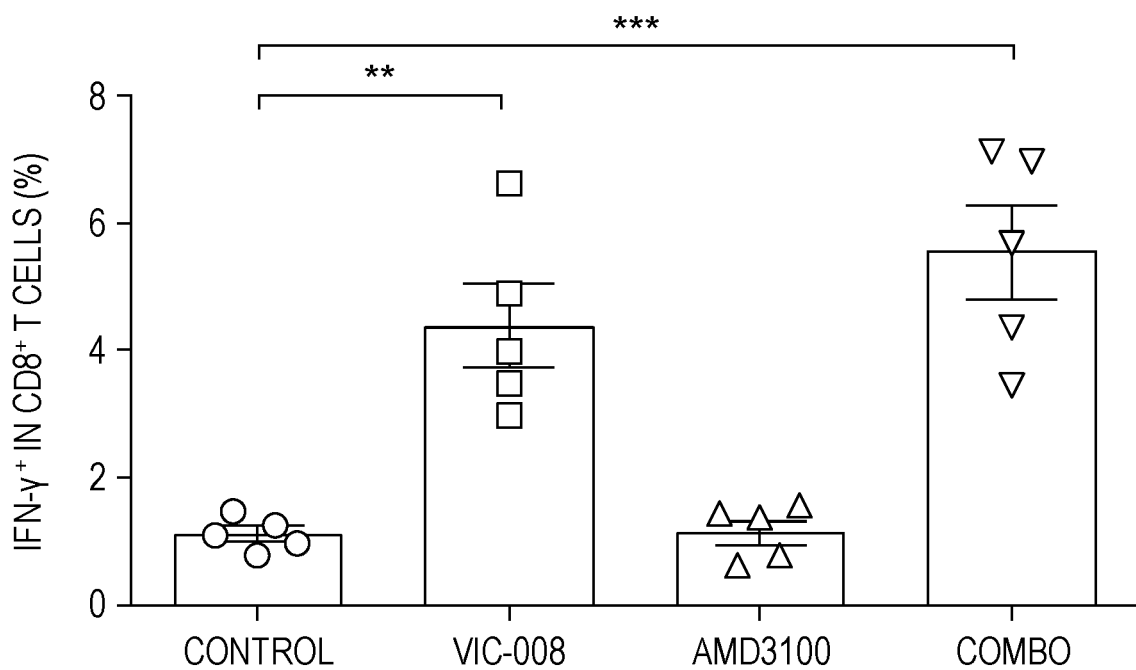

Spleens, axillary and inguinal lymph nodes, and intraperitoneal tumors were collected from tumor-bearing mice one week after the last treatment. Single cells were prepared from these tissues and analyzed by flow cytometry (FIG. 8A). The proportions of $CD8^+$ T cells in the total live cells recovered from spleens (P<0.05 and P<0.05, respectively) and tumors (P<0.01 and P<0.01, respectively) for both the 40L and AE17 models, and from lymph nodes (P<0.01) in AE17 model were significantly increased in the VIC-008 treatment group compared to that in the saline control group (FIGS. 8B-8F). In VIC-008 and AMD3100 combination treatment group, the proportions of $CD8^+$ T cells in the total live cells recovered from spleens (P<0.05 and P<0.05, respectively) and tumors (P<0.01 and P<0.05, respectively) for both the 40L and AE17 models, and from lymph nodes (P<0.001) in AE17 model were significantly increased compared to that in the saline control group. AMD3100 treatment did not increase the proportion of $CD8^+$ T cells in these tissues. Moreover, there was no difference in the proportion of $CD8^+$ T cells between the VIC-008 and combination treatment groups, indicating that VIC-008 increased lymphocyte infiltration of these tissues.

VIC-008 Enhances Tumor Antigen-Specific $CD8^+$ T-Cell Responses

Next, single cells isolated from spleens and lymph nodes from tumor-bearing mice were restimulated with recombinant mesothelin ex vivo and analyzed intracellular IFN-γ in $CD8^+$ T cells. Mesothelin-specific IFN-γ expression in splenic $CD8^+$ T cells both in 40L (P<0.001) and AE17 (P<0.001) models, and in lymph node $CD8^+$ T cells in the AE17 model (P<0.01), were significantly greater in mice treated with VIC-008 alone compared to that in mice treated with saline (FIGS. 9A-9D). In VIC-008 and AMD3100 combination treatment group, mesothelin-specific IFN-γ expression in splenic $CD8^+$ T cells both in 40L (P<0.01) and AE17 (P<0.01) models, and in lymph node $CD8^+$ T cells in the AE17 model (P<0.001), were significantly greater compared to that in mice treated with saline. AMD3100 treatment by itself did not enhance antigen-specific IFN-γ secretion in $CD8^+$ T cells. Together, these data support the view that VIC-008 treatment enhances antitumor $CD8^+$ T-cell responses in both the 40L and AE17 mesothelioma mouse models.

AMD3100 Decreases PD-1 Expression on $CD8^+$ T Cells

Figure 10A:
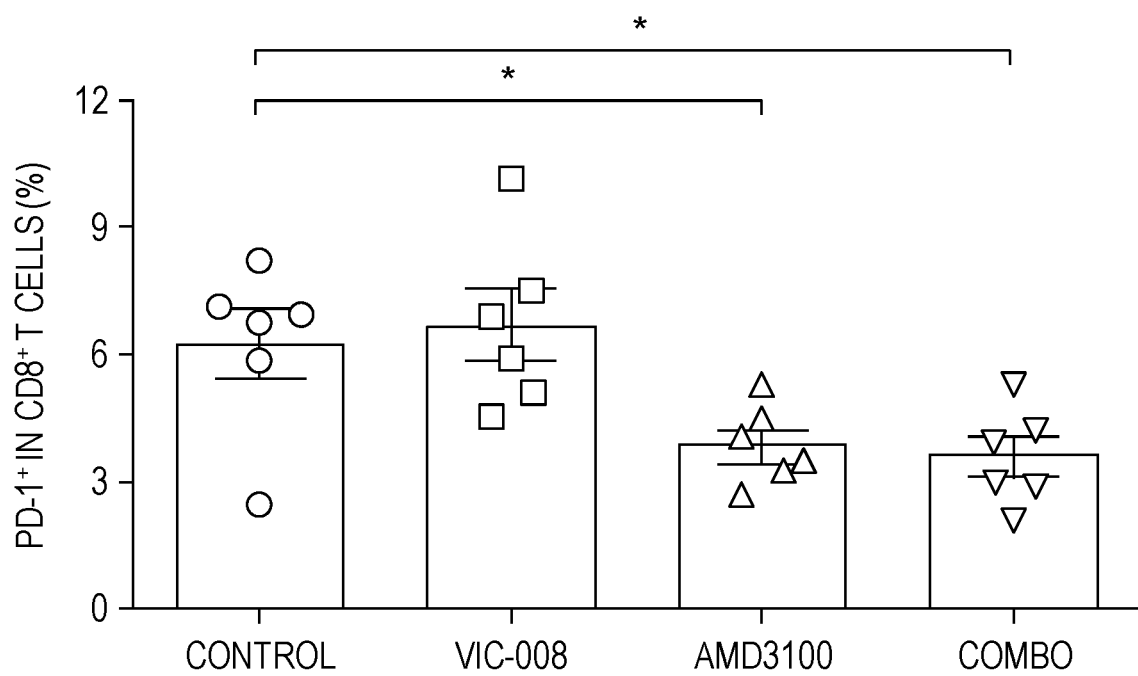
FIGS. 10A-10E show AMD3100 decreased PD-1 expression on CD8$^+$ T cells. The proportion of PD-1-expressing cells in CD8$^+$ T cells in spleens of 40L (n=6) (A) and AE17 (n=5) (B) mice. The proportion of PD-1-expressing cells in CD8$^+$ T cells in lymph nodes of AE17 mice (n=5) (C). The proportion of PD-1-expressing cells in CD8$^+$ T cells in tumors of 40L (n=6) (D) and AE17 (n=5) (E) mice. *P<0.05 and **P<0.01. Data are presented as mean±SEM.
Figure 10B:
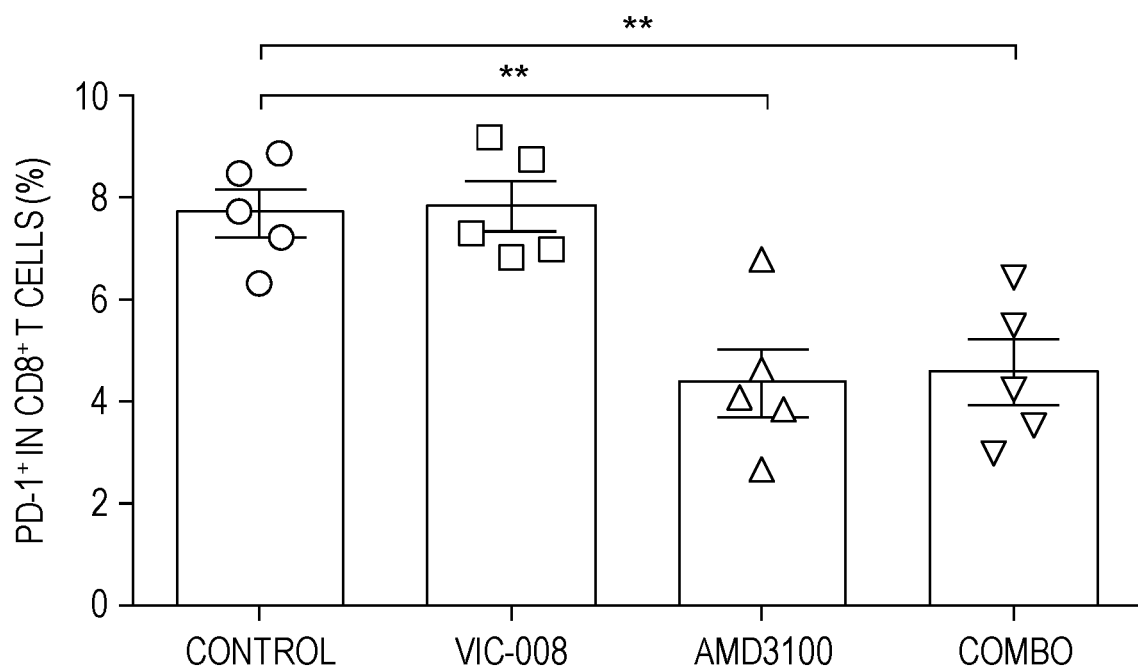
Figure 10C:
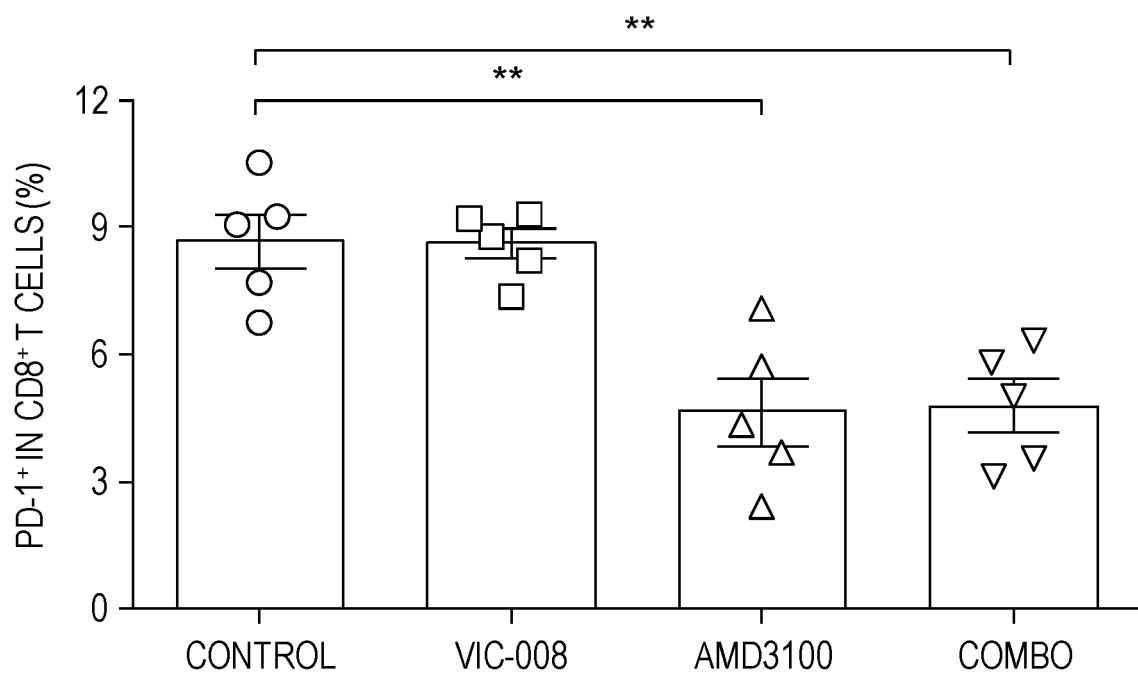
Figure 10D:
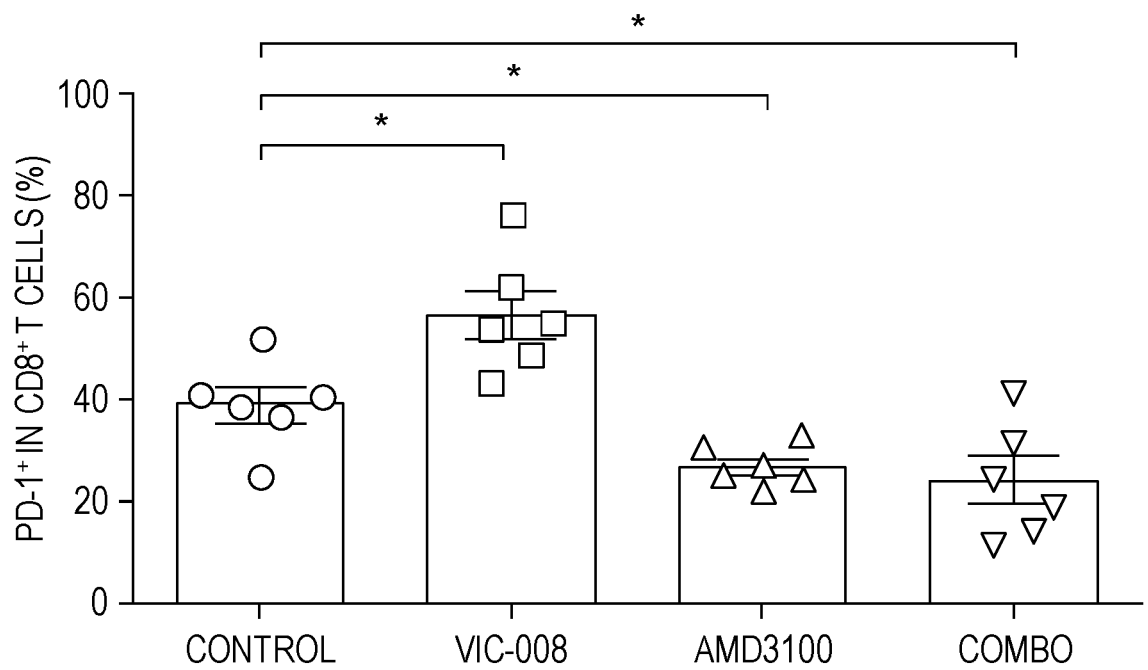
Figure 10E:
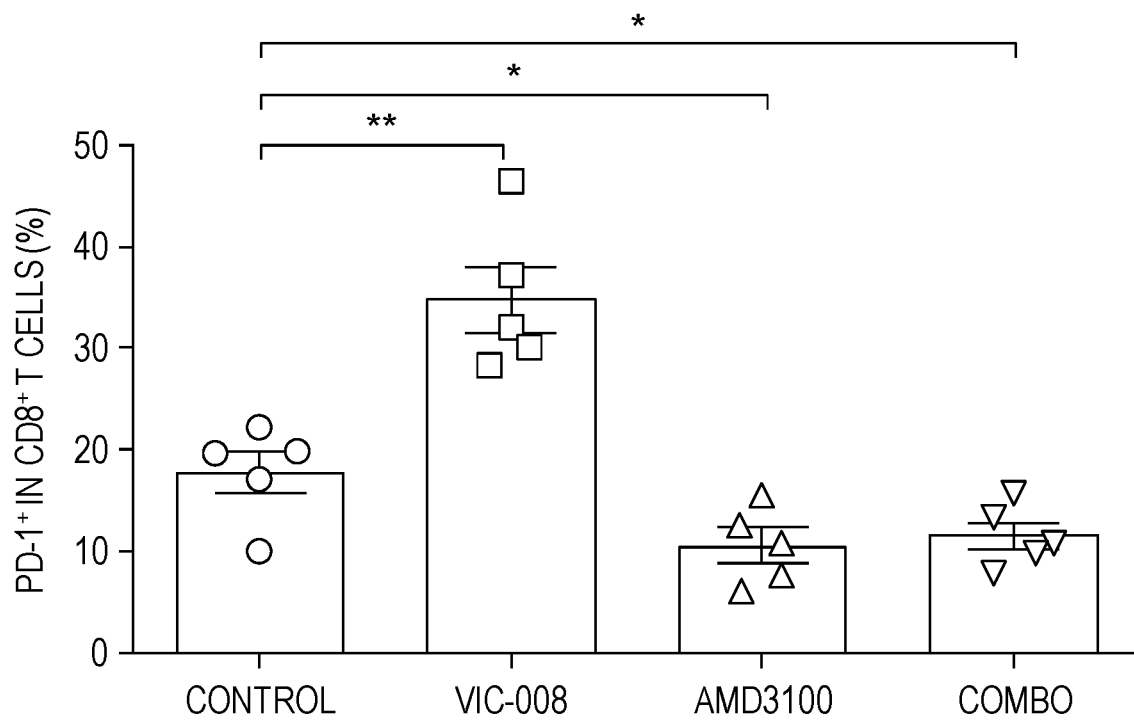

Next, expression of programmed cell death protein-1 (PD-1) on $CD8^+$ T cells was evaluated in spleen, tumor and lymph nodes. There was no significant difference between the VIC-008 treatment group and the saline control group in the proportion of PD-1-expressing $CD8^+$ T cells in spleens in both the 40L and AE17 tumor-bearing mice, and in lymph nodes for AE17 mice (FIGS. 10A-10C). In marked contrast, significantly more intratumoral $CD8^+$ T cells in the VIC-008 treated group expressed PD-1 in the 40L tumors (P<0.05) and AE17 tumors (P<0.01) compared with the saline-treated controls (FIGS. 10D-10E). The percentage of PD-1 expressing $CD8^+$ T cells ranged between 43-76% and 28-47% in the 40L tumors and AE17 tumors respectively compared to only 5-10% in spleen and lymph nodes. These data indicate that the antitumor activity of the $CD8^+$ T cells in the tumor environment induced by VIC-008 treatment could be obstructed by activation of the PD-1/PD-L1 pathway.

Compared to this effect of VIC-008, and surprisingly, it was found that AMD3100 reduced PD-1 expression on $CD8^+$ T cells. AMD3100 treatment alone led to significantly fewer PD-1-expressing $CD8^+$ T cells in spleens (P<0.05 and P<0.01, respectively) and tumors (P<0.05 and P<0.05, respectively) in both the 40L and AE17 tumor-bearing mice, and in lymph nodes (P<0.01) for AE17 mice than in mice treated with saline. In AMD3100 and VIC-008 combination treatment group significantly fewer $CD8^+$ T cells expressed PD-1 in spleens (P<0.05 and P<0.01, respectively) and tumors (P<0.05 and P<0.05, respectively) in both the 40L and AE17 tumor-bearing mice, and in lymph nodes (P<0.01) for AE17 mice compared with the saline-treated controls. There was no significant difference in the proportion of PD-1-expressing $CD8^+$ T cells in these tissues between the AMD3100 monotherapy and AMD3100-VIC-008 combination therapy groups. These data indicated that AMD3100 could inhibit $CD8^+$ T cells from expressing PD-1 in spleens, lymph nodes and tumors.

AMD3100 Reduces Tumor-Infiltrating $T_{reg}$ Cells

Figure 11A:
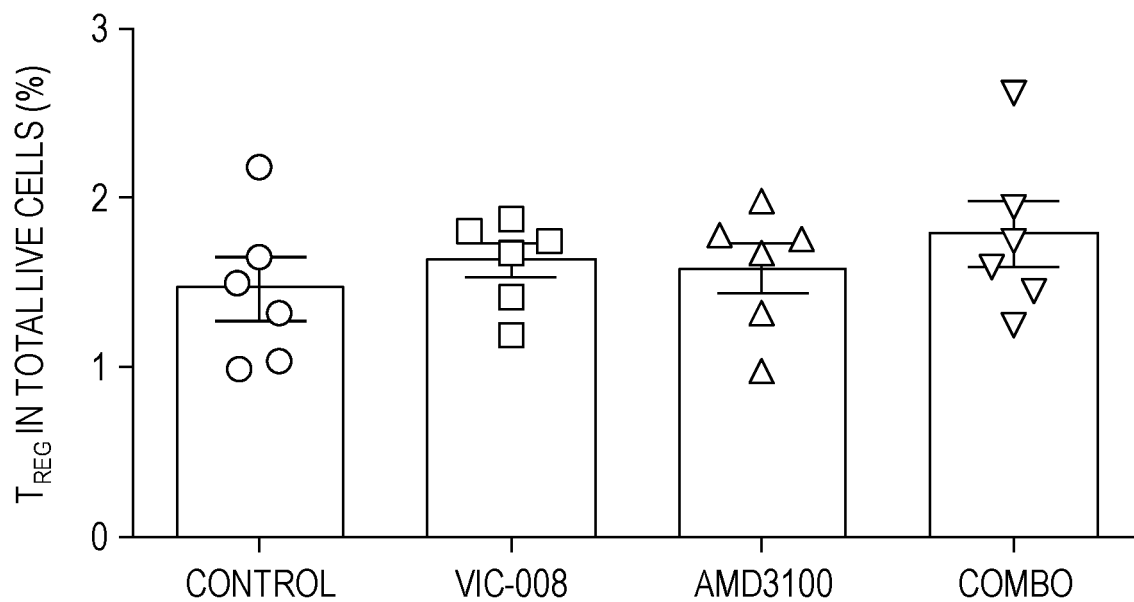
FIGS. 11A-11F show AMD3100 reduced Tumor-infiltrating $T_{reg}$. The proportion of $T_{reg}$ in total live splenocytes in 40L (n=6) (A) and AE17 (n=5) (B) mice. The proportion of $T_{reg}$ in total live cells in lymph nodes of AE17 mice (n=5) (C). The ratio of CD8$^+$ T cells to $T_{reg}$ in lymph nodes of AE17 mice (n=5) (D). The proportion of $T_{reg}$ in total live cells in tumors of 40L mice (n=6) (E). The ratio of CD8$^+$ T cells to $T_{reg}$ in tumors of 40L mice (n=6) (F). *P<0.05, P<0.01, *P<0.001 and ****P<0.0001. Data are presented as mean ±SEM.
Figure 11B:
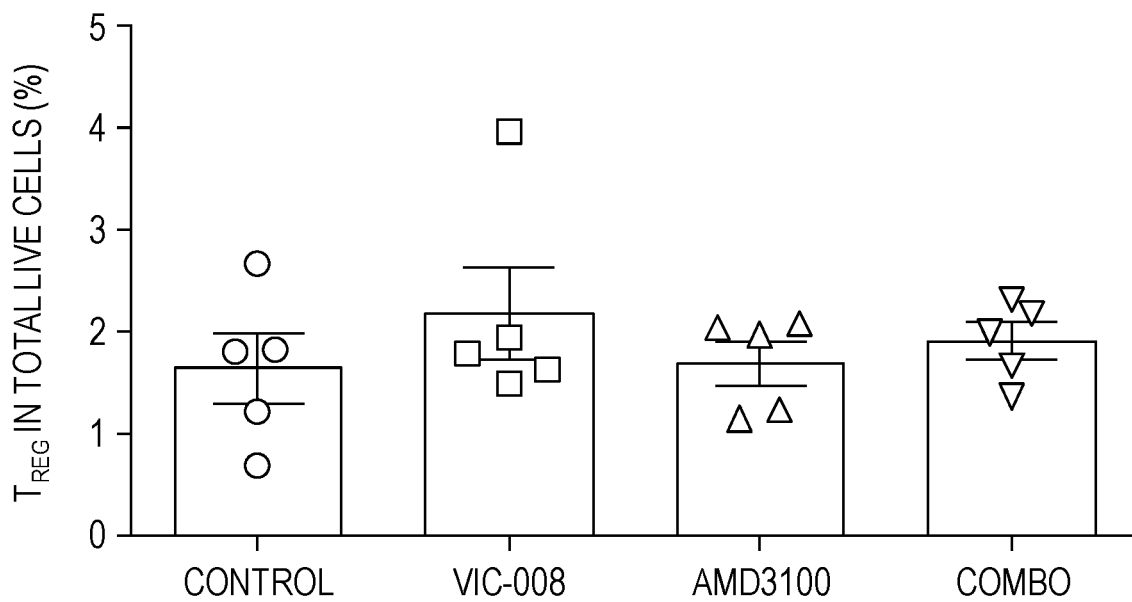
Figure 11C:
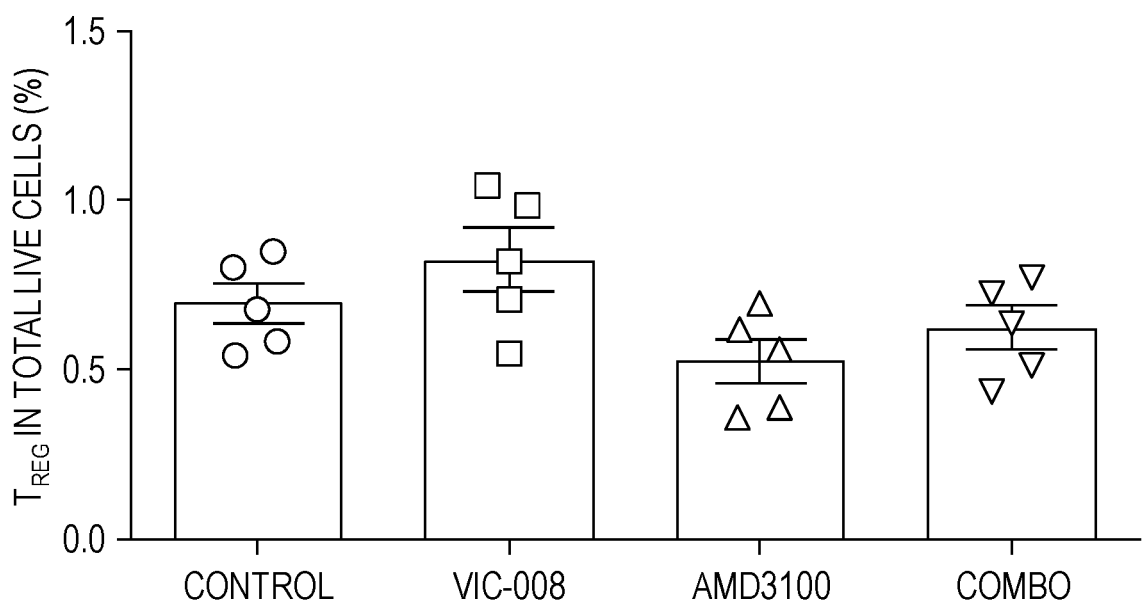
Figure 11D:
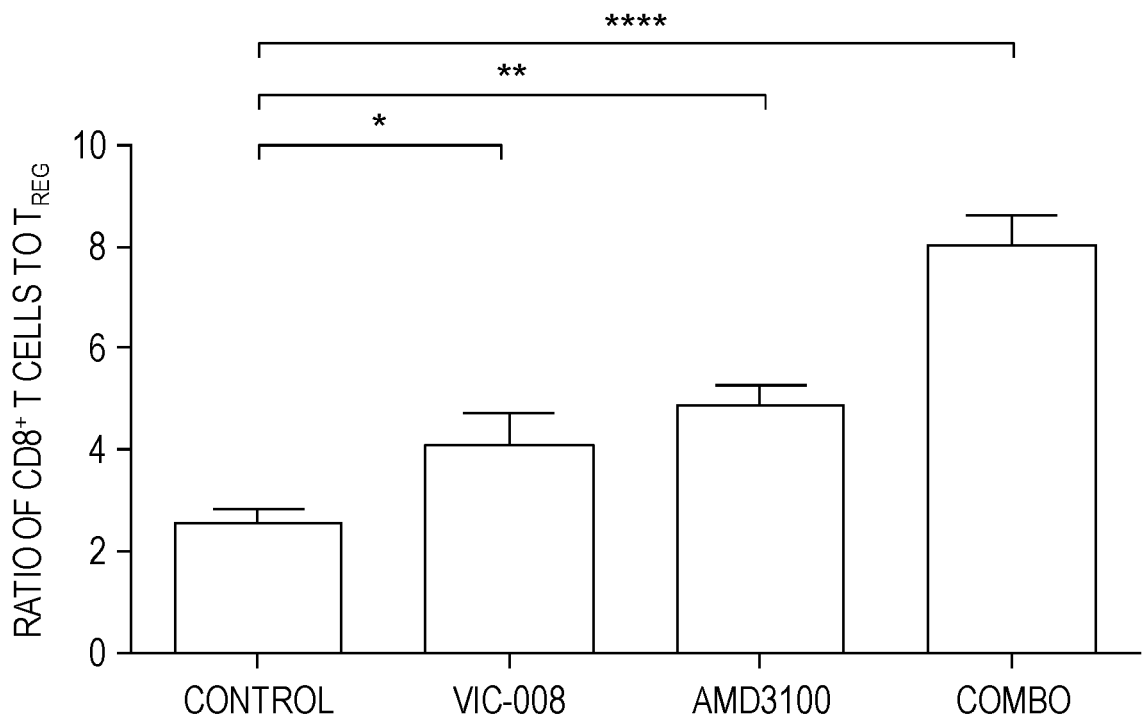
Figure 11E:
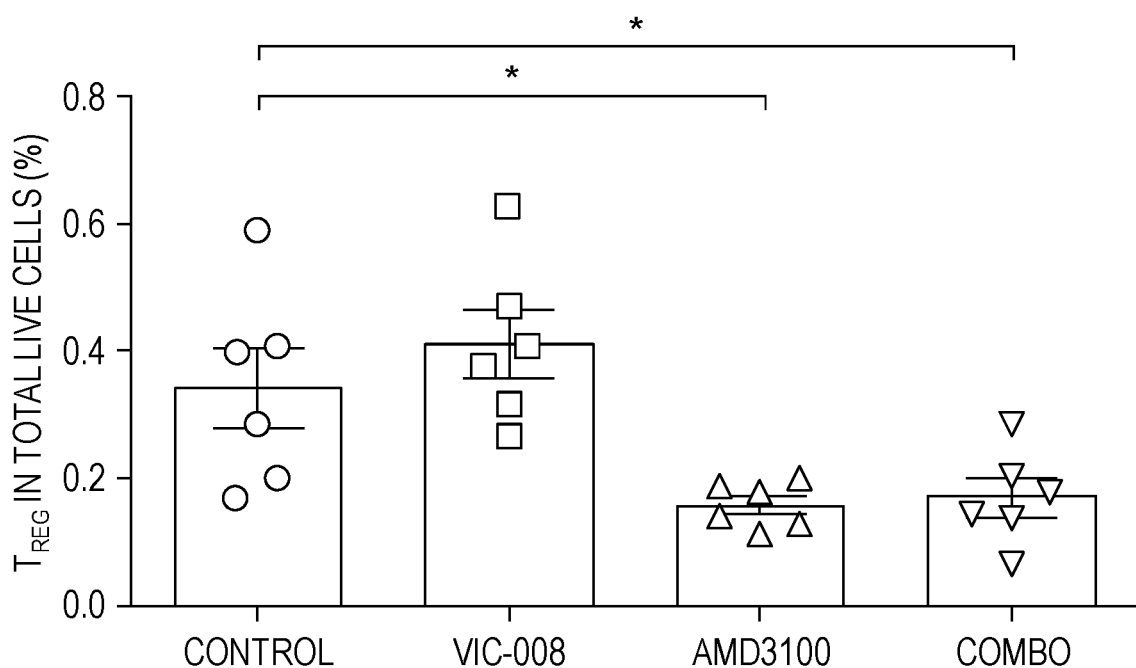
Figure 11F:
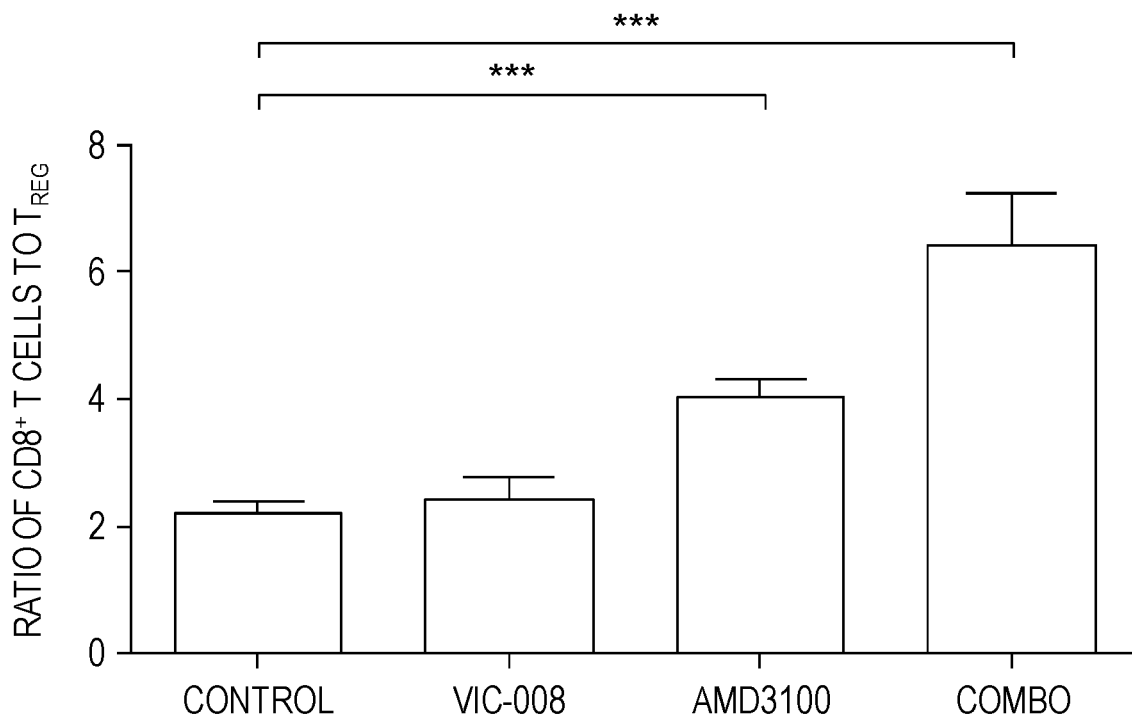

Next, the impact of AMD3100 on $T_{reg}$ cells was evaluated. AMD3100 did not alter the proportions of $T_{reg}$ cells found in spleens of 40L tumor-bearing mice (FIGS. 11A-11B). In AE17 tumor-bearing mice AMD3100 alone generally reduced $T_{reg}$ in the lymph nodes (FIG. 11C) and AMD3100 alone or in combination with VIC-008 significantly increased the cell ratio of $CD8^+$ T cells to $T_{reg}$ cells (P<0.01 and P<0.0001, respectively) compared to saline treatment (FIG. 11D). In tumors from both the 40L and AE17 models, AMD3100 applied as monotherapy significantly decreased the proportions of $T_{reg}$ (P<0.05 and P<0.01, respectively) and increased the ratio of $CD8^+$ T cells to $T_{reg}$ (P<0.001 and P<0.01, respectively) compared to saline treatment (FIGS. 11E-11F). In AMD3100 and VIC-008 combination treatment group the proportions of $T_{reg}$ were significantly decreased (P<0.05 and P<0.05, respectively) and the ratio of $CD8^+$ T cells to $T_{reg}$ increased (P<0.001 and P<0.0001, respectively) compared to saline treatment in both the 40L and AE17 models. In these two murine mesothelioma models, AMD3100 reduced intratumoral $T_{reg}$ infiltration.

AMD3100 Modulates $T_{reg}$ Cells Toward a T Helper Phenotype

Figure 12A:
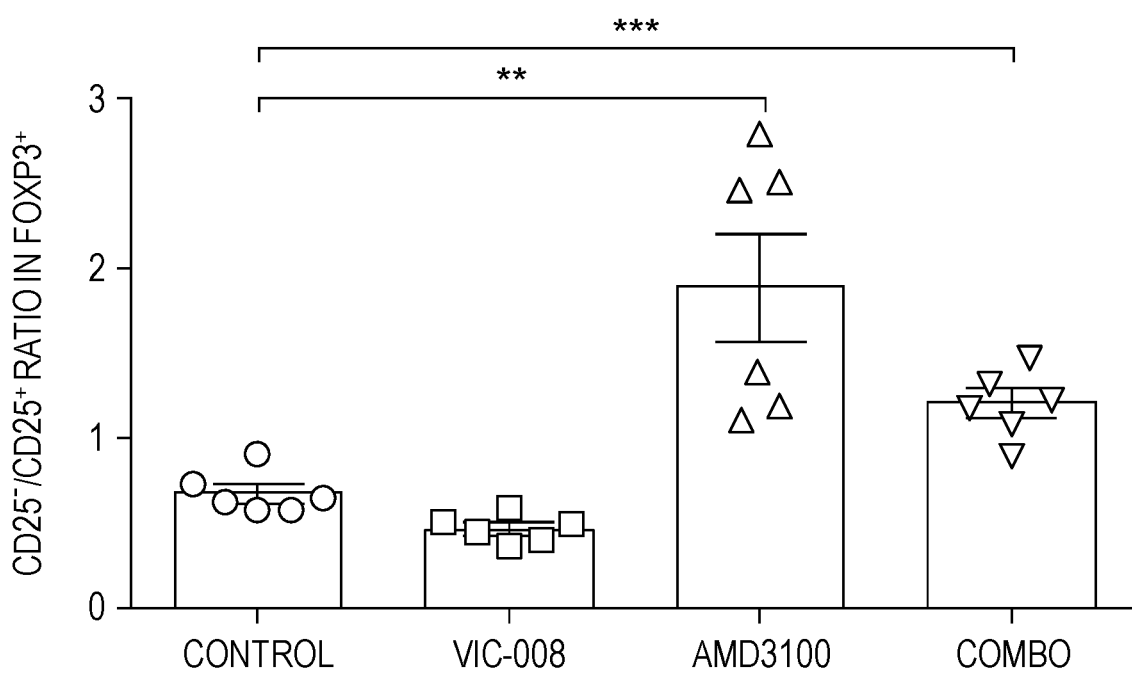
FIGS. 12A-12E show AMD3100 reprogrammed $T_{reg}$ to helper-like cells. The ratio of CD25$^-$ to CD25$^+$ cells in CD4$^+$ Foxp3$^+$ T-cell population in tumors of 40L (n=6) (A) and lymph nodes of AE17 (n=5) (B) mice. Representative density plots of IL-2$^+$ CD40L$^+$ cells in Foxp3$^+$ CD25$^-$ $T_{reg}$ population in different treatment groups (C). The proportion of IL-2$^+$ CD40L$^+$ cells in Foxp3$^+$ CD25$^-$ $T_{reg}$ population in tumors of 40L (n=6) (D) and in lymph nodes of AE17 (n=5) (E) mice. *P<0.05, P<0.01,*P<0.001 and ****P<0.0001. Data are presented as mean±SEM.
Figure 12B:
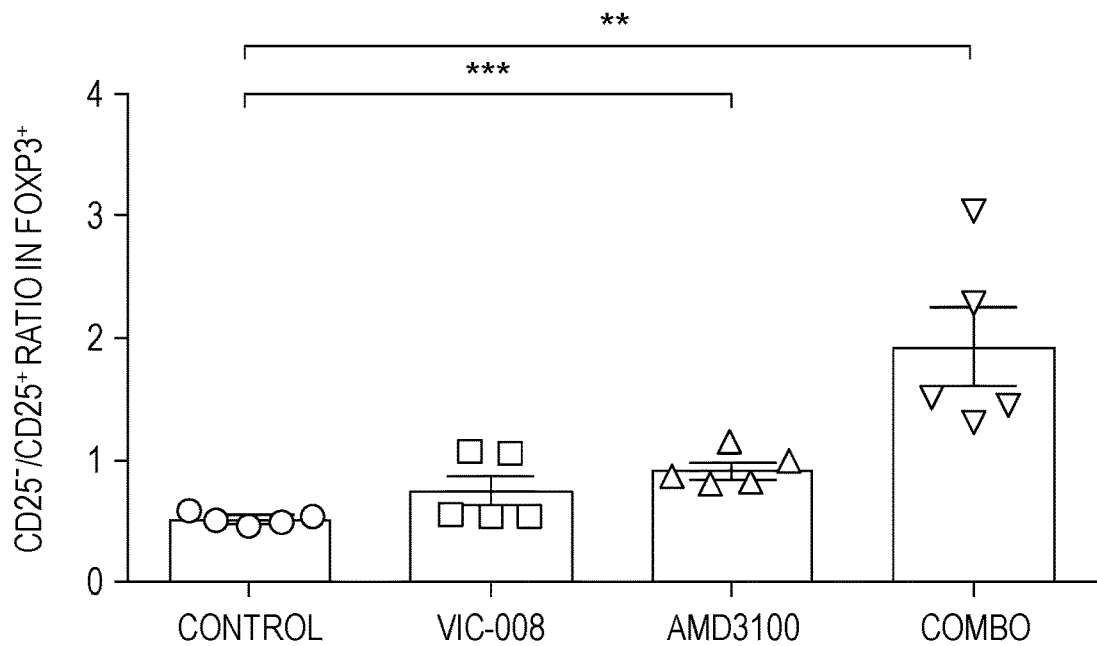
Figure 12C:
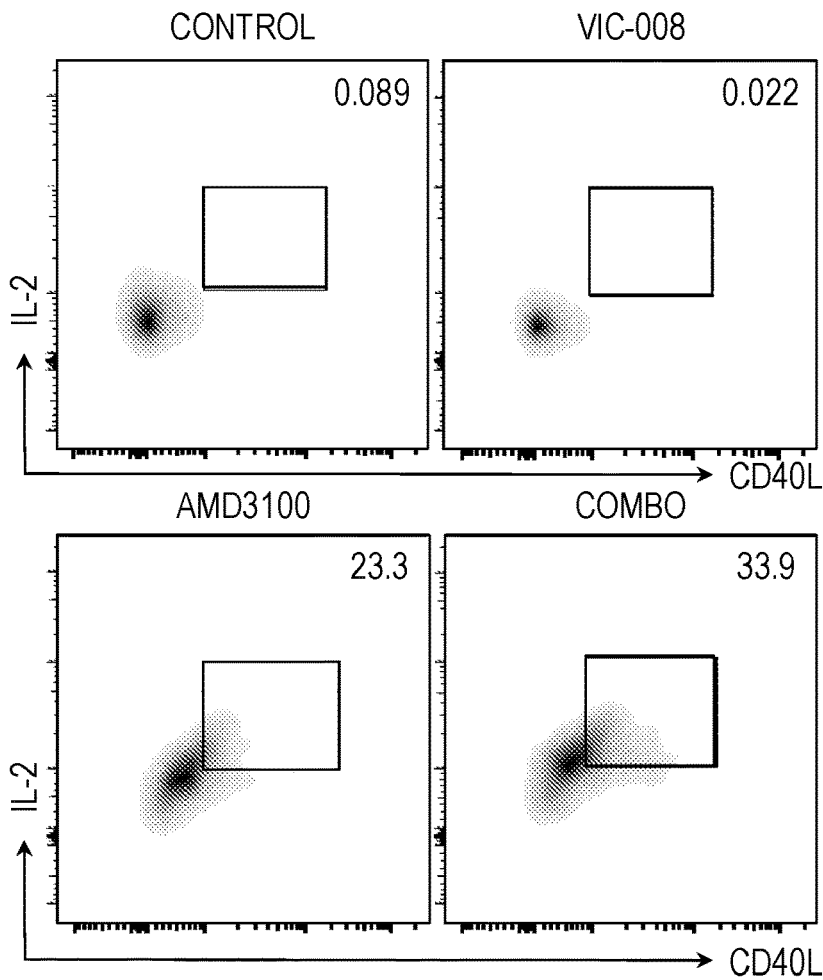
Figure 12D:
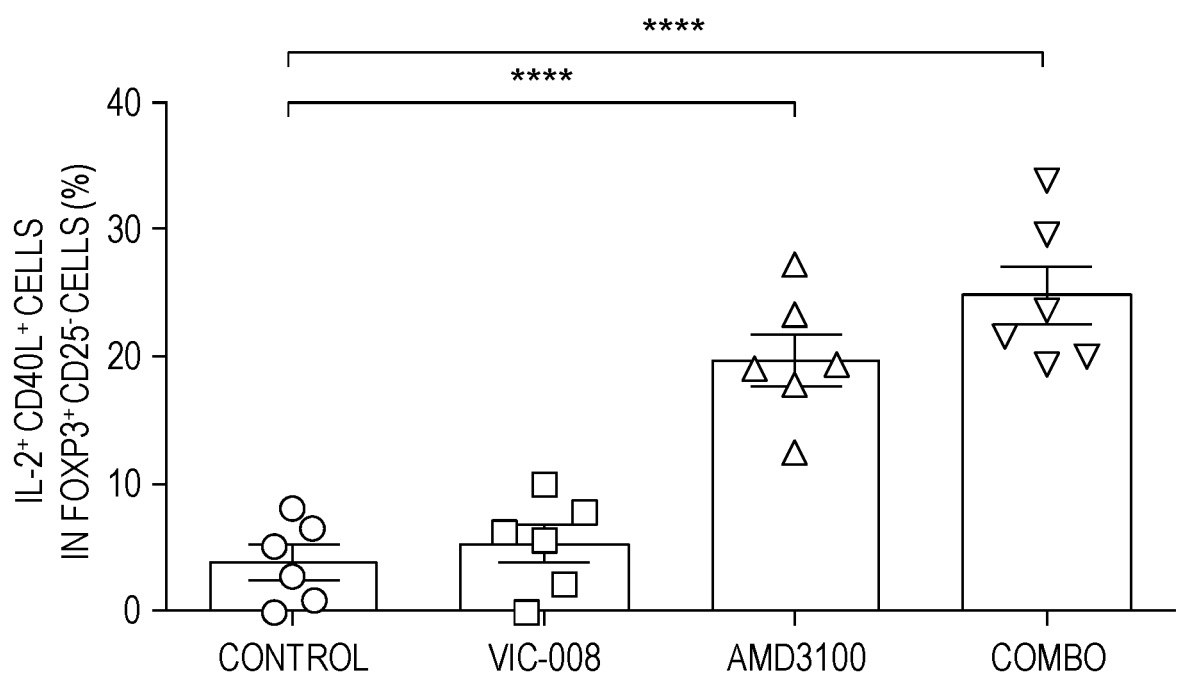
Figure 12E:
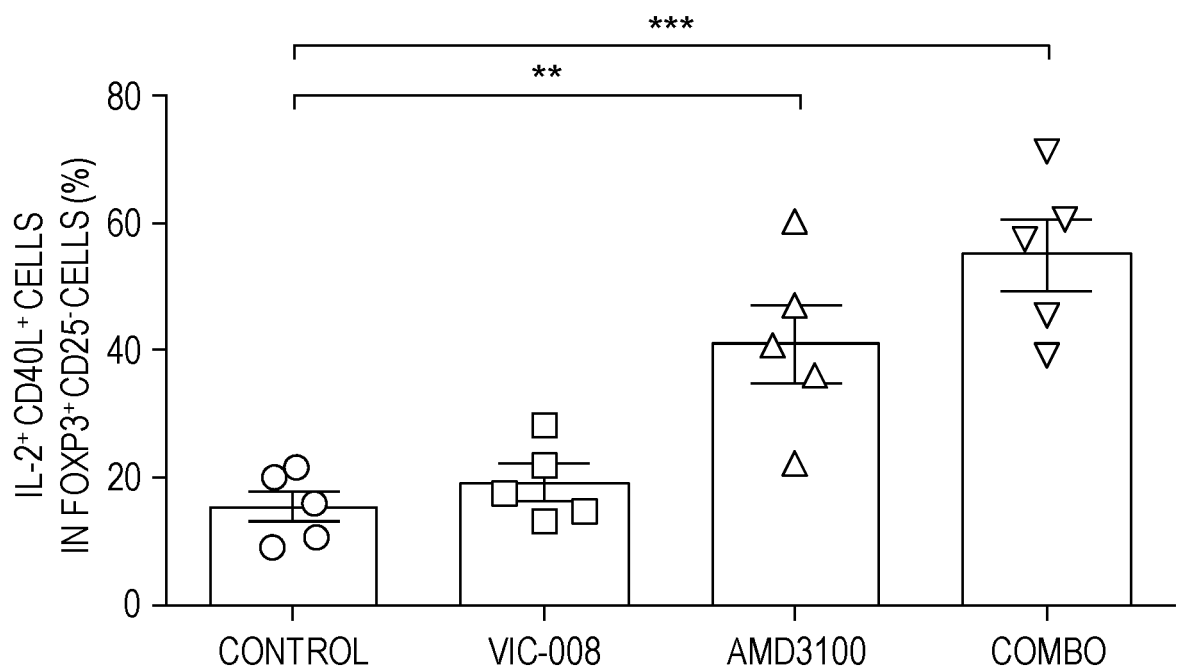

It was observed that AMD3100, alone or in combination with VIC-008, significantly increased the ratio of $CD25^-$ cells to $CD25^+$ cells within the $Foxp3^+$ population in both 40L (FIG. 12A, P<0.01 and P<0.001, respectively) and in the lymph nodes in the AE17 model (FIG. 12B, P<0.001 and P<0.01, respectively). Among the $Foxp3^+$ $CD25^-$ $T_{reg}$ population significantly more cells were phenotypically $IL-2^+$ $CD40L^+$ (FIGS. 12C-12E) after AMD3100 monotherapy and combination therapy with VIC-008, which suggested a change from $T_{reg}$ cells to helper-like cells that had lost CD25 without loss of Foxp3, and may have lost their immunosuppressive function. There was no difference in the proportion of IL-2⁺ CD40L⁺ cells in the Foxp3⁺ CD25⁻ T$_{reg}$ population between AMD3100 monotherapy and combination therapy groups, indicating that AMD3100 treatment may be the major driver of reprogramming of T$_{reg}$ into helper-like cells.

AMD3100-Driven Modulation of T$_{reg}$ Phenotype Requires TCR Activation

Figure 13A:
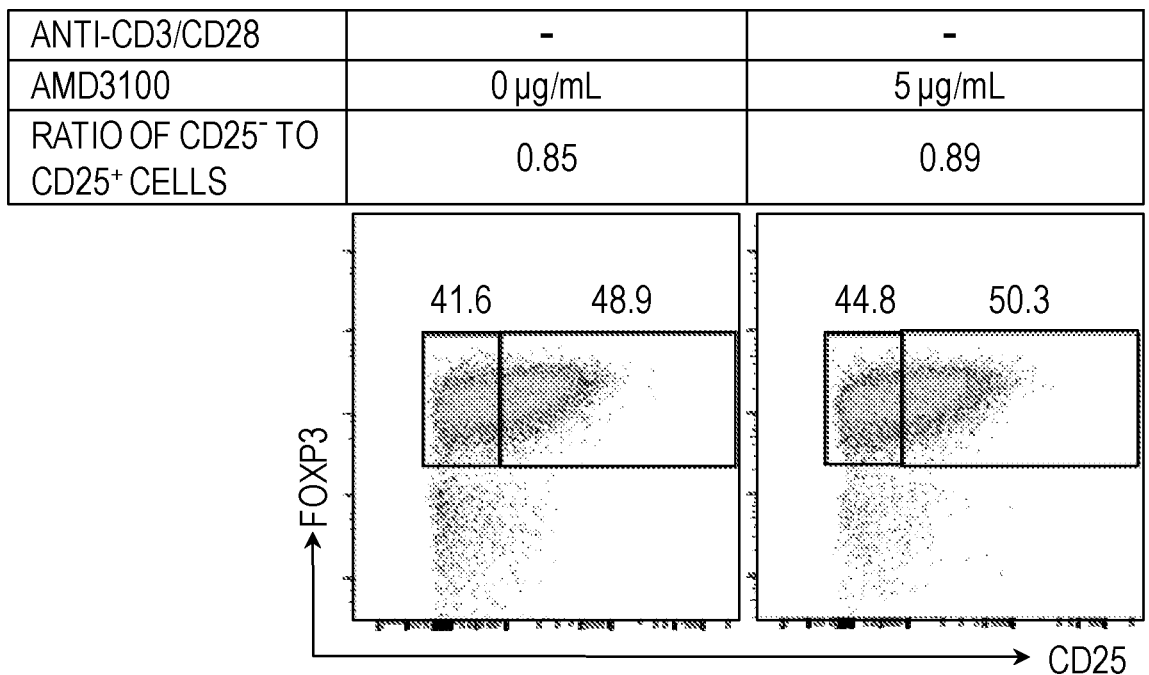
FIGS. 13A-13F show AMD3100-driven $T_{reg}$ reprogramming required TCR activation. (A) Representative dot plots of Foxp3$^+$ CD25$^-$ and Foxp3$^+$ CD25$^+$ population with or without AMD3100 treatment under no anti-CD3/CD28 stimulation (A) and statistical difference was analyzed using unpaired t-test with Welch's correction (n=4) (B). Representative dot plots of Foxp3$^+$ CD25$^-$ and Foxp3$^+$ CD25$^+$ population with or without AMD3100 treatment under anti-CD3/CD28 stimulation (C) and statistical difference was analyzed using unpaired t-test with Welch's correction (n=4) (D). Representative density plots of IL-2$^+$ CD40L$^+$ cells in Foxp3$^+$ CD25$^-$ $T_{reg}$ population with or without AMD3100 treatment under anti-CD3/CD28 stimulation (E) and statistical difference was analyzed using unpaired t-test with Welch's correction (n=4) (F). Data are presented as mean±SEM.
Figure 13B:
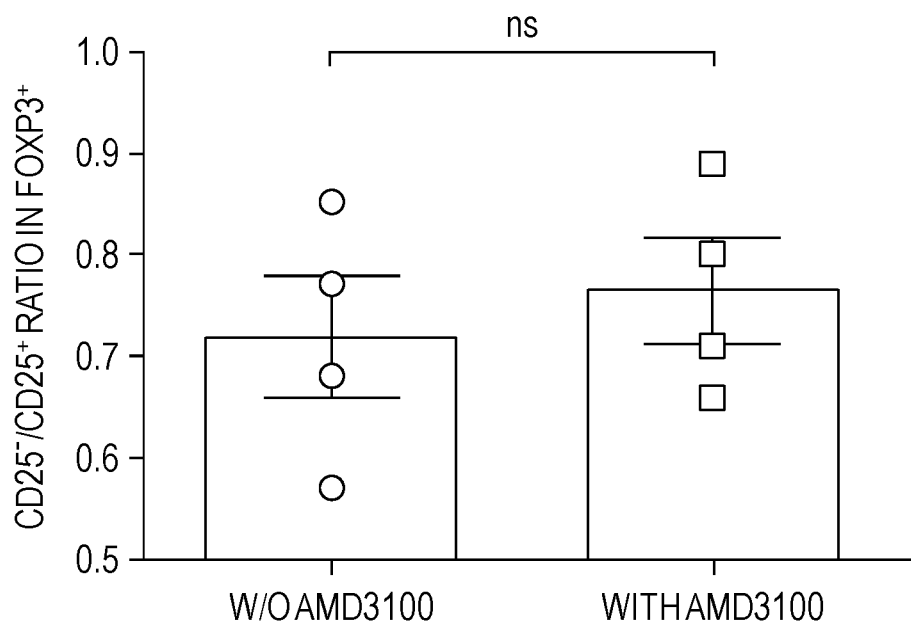
Figure 13C:
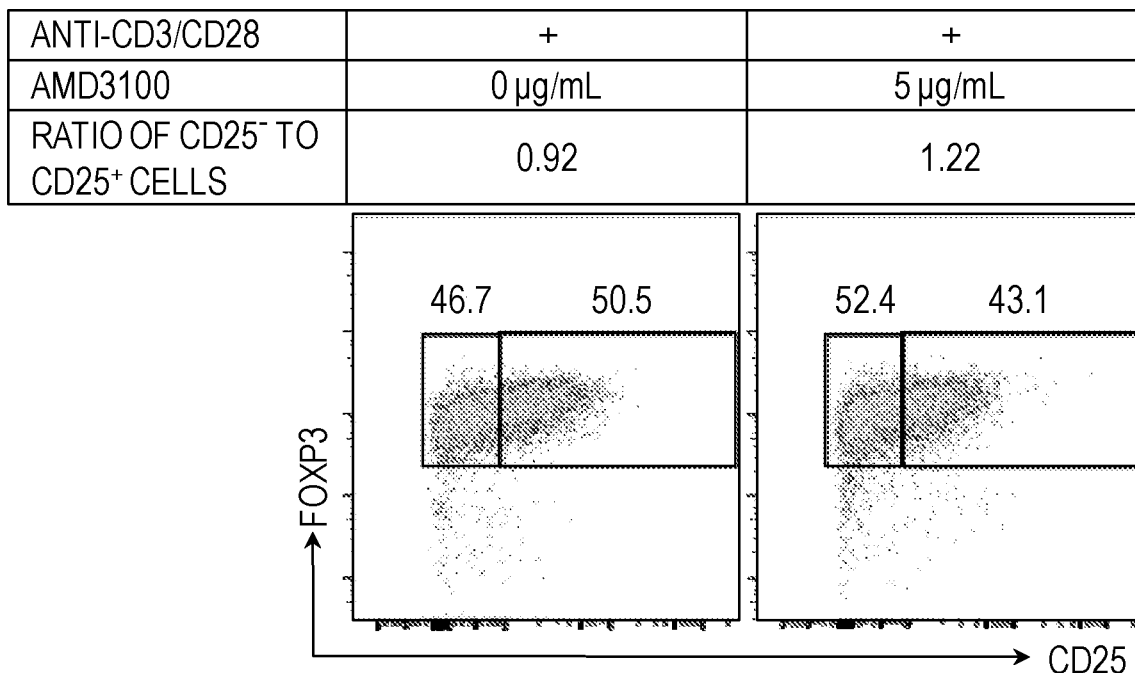
Figure 13D:
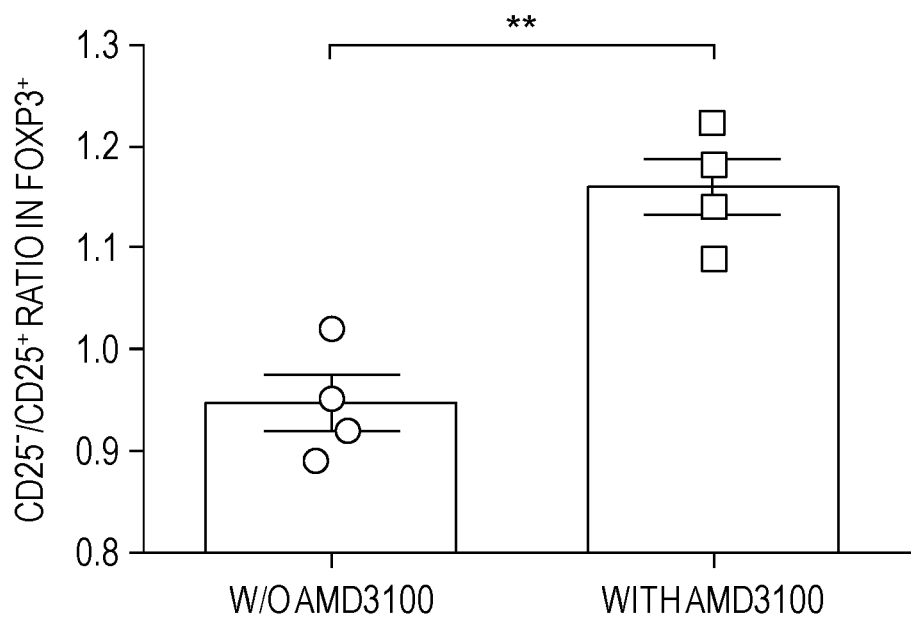
Figure 13E:
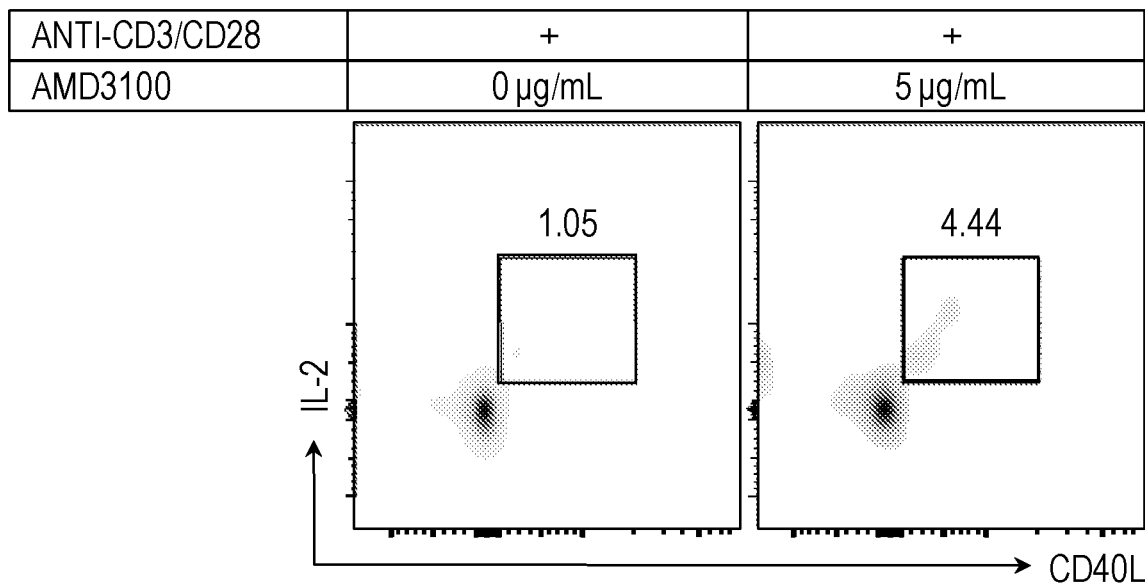
Figure 13F:
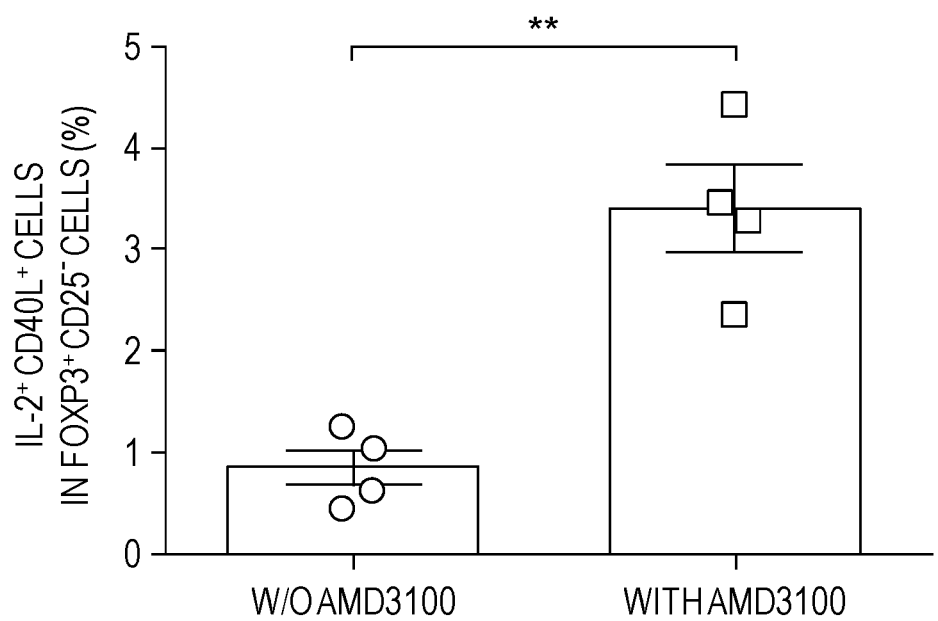

It was next addressed whether AMD3100-driven T$_{reg}$ modulation could be initiated in isolated single cells. Cells expressing GFP-Foxp3 from CD4⁺ splenocytes in T-Red/FoxP3 GFP transgenic mice were sorted and treated in vitro with AMD3100. AMD3100 treatment alone did not change the ratio of the proportion of CD25⁻ cells to CD25⁺ cells in the Foxp3⁺ CD4⁺ population (FIGS. 13A-13B). However, in the presence of stimulation by anti-CD3/CD28 antibodies to trigger TCR activation, AMD3100 treatment significantly increased the ratio of the proportion of CD25⁻ cells to CD25⁺ cells in the Foxp3⁺ CD4⁺ population (FIGS. 13C-13D, P=0.0017) and converted more Foxp3⁺ CD25⁻ T$_{reg}$ into IL-2⁺ CD40L⁺ cells (FIGS. 13E-13F, P=0.0015). These data indicated that the conversion of T$_{reg}$ cells into helper-like cells can be mediated by AMD3100 treatment of single cells upon TCR activation.

The foregoing is illustrative of the present invention, and is not to be construed as limiting thereof. The invention is defined by the following claims, with equivalents of the claims to be included therein.

What is claimed is:

1. A method for preparing activated antigen-presenting cells (APCs), the method comprising:
   a) incubating immune cells comprising APCs ex vivo in presence of cancer cells and a fusion protein for a time period sufficient to produce activated APCs, wherein at least one activated APC displays an antigen derived from the cancer cells; and
   b) isolating the activated APCs;
   wherein the fusion protein comprises an anti-MSLN scFv and a stress protein component, wherein said anti-MSLN scFv binds to mesothelin on one or more of the cancer cells and said stress protein component causes activation of the APCs,
   and wherein the method further comprises contacting the isolated activated APCs with an effective amount of an anti-chemorepellant agent, wherein the anti-chemorepellant agent is AMD3100.

2. The method of claim 1, wherein the stress protein component comprises HSP70 and/or modified sequence thereof.

3. The method of claim 2, wherein the stress protein component comprises *Mycobacterium tuberculosis*-derived HSP70 (MtbHsp70) and/or modified sequence thereof.

4. The method of claim 1, wherein the cancer cells are derived from mesothelioma.

5. The method of claim 1, further comprising expanding the APCs in presence of a growth factor.

6. The method of claim 5, wherein the growth factor is a cytokine.

7. The method of claim 6, wherein the growth factor is selected from a group consisting of Flt-3 ligand, GM-CSF, IL-4, M-CSF, IFNα, IL-1β, IL-4, IL-6, IL-13, IL-15 and TNFα.

8. The method of claim 1, wherein the immune cells comprise dendritic cells, B lymphocytes, and/or mononuclear phagocytes, said mononuclear phagocytes comprising monocytes or macrophages.

9. The method of claim 1, wherein at least one immune cell comprises a CD40 receptor.

10. The method of claim 1, wherein the activated APCs comprise activated dendritic cells.

11. The method of claim 10, wherein the dendritic cells are differentiated or matured from dendritic cell precursors.

12. The method of claim 1, wherein the isolated activated APCs are free or substantially free of the cancer cells and/or the fusion protein.

13. The method of claim 12, wherein the fusion protein comprises the peptide sequence of SEQ ID NO: 2.

14. The method of claim 1, wherein the fusion protein comprises the peptide sequence of SEQ ID NO: 1 or SEQ ID NO: 2.

* * * * *

```
                         SEQUENCE LISTING

<160> NUMBER OF SEQ ID NOS: 2

<210> SEQ ID NO 1
<211> LENGTH: 915
<212> TYPE: PRT
<213> ORGANISM: Artificial
<220> FEATURE:
<223> OTHER INFORMATION: fusion protein

<400> SEQUENCE: 1

Gly Ser Ser Gln Val Gln Leu Gln Gln Ser Gly Pro Gly Leu Val Thr
1               5                   10                  15

Pro Ser Gln Thr Leu Ser Leu Thr Cys Ala Ile Ser Gly Asp Ser Val
            20                  25                  30

Ser Ser Asn Ser Ala Thr Trp Asn Trp Ile Arg Gln Ser Pro Ser Arg
        35                  40                  45

Gly Leu Glu Trp Leu Gly Arg Thr Tyr Tyr Arg Ser Lys Trp Tyr Asn
    50                  55                  60

Asp Tyr Ala Val Ser Val Lys Ser Arg Met Ser Ile Asn Pro Asp Thr
65                  70                  75                  80

Ser Lys Asn Gln Phe Ser Leu Gln Leu Asn Ser Val Thr Pro Glu Asp
                85                  90                  95

Thr Ala Val Tyr Tyr Cys Ala Arg Gly Met Met Thr Tyr Tyr Tyr Gly
            100                 105                 110

Met Asp Val Trp Gly Gln Gly Thr Thr Val Thr Val Ser Ser Gly Ile
        115                 120                 125

Leu Gly Ser Gly Gly Gly Gly Ser Gly Gly Gly Gly Ser Gly Gly Gly
    130                 135                 140

Gly Ser Gln Pro Val Leu Thr Gln Ser Ser Ser Leu Ser Ala Ser Pro
145                 150                 155                 160

Gly Ala Ser Ala Ser Leu Thr Cys Thr Leu Arg Ser Gly Ile Asn Val
                165                 170                 175

Gly Pro Tyr Arg Ile Tyr Trp Tyr Gln Gln Lys Pro Gly Ser Pro Pro
            180                 185                 190

Gln Tyr Leu Leu Asn Tyr Lys Ser Asp Ser Asp Lys Gln Gln Gly Ser
        195                 200                 205

Gly Val Pro Ser Arg Phe Ser Gly Ser Lys Asp Ala Ser Ala Asn Ala
    210                 215                 220

Gly Val Leu Leu Ile Ser Gly Leu Arg Ser Glu Asp Glu Ala Asp Tyr
225                 230                 235                 240

Tyr Cys Met Ile Trp His Ser Ser Ala Ala Val Phe Gly Gly Gly Thr
                245                 250                 255

Gln Leu Thr Val Leu Ser Gly Ile Leu Glu Gln Gln Gly Gly Gly Gly
```

```
            260                 265                 270
Gly Ser Gly Gly Gly Ser Gly Gly Gly Ser Ala Ala Ala Met
            275                 280             285
Arg Ser Met Ala Arg Ala Val Gly Ile Asp Leu Gly Thr Thr Asn Ser
        290                 295             300
Val Val Ser Val Leu Glu Gly Gly Asp Pro Val Val Ala Asn Ser
305                 310                 315                 320
Glu Gly Ser Arg Thr Thr Pro Ser Ile Val Ala Phe Ala Arg Asn Gly
                325                 330                 335
Glu Val Leu Val Gly Gln Pro Ala Lys Asn Gln Ala Val Thr Asn Val
                340                 345                 350
Asp Arg Thr Val Arg Ser Val Lys Arg His Met Gly Ser Asp Trp Ser
            355                 360                 365
Ile Glu Ile Asp Gly Lys Lys Tyr Thr Ala Pro Glu Ile Ser Ala Arg
            370                 375                 380
Ile Leu Met Lys Leu Lys Arg Asp Ala Glu Ala Tyr Leu Gly Glu Asp
385                 390                 395                 400
Ile Thr Asp Ala Val Ile Thr Thr Pro Ala Tyr Phe Asn Asp Ala Gln
                405                 410                 415
Arg Gln Ala Thr Lys Asp Ala Gly Gln Ile Ala Gly Leu Asn Val Leu
                420                 425                 430
Arg Ile Val Asn Glu Pro Thr Ala Ala Ala Leu Ala Tyr Gly Leu Asp
            435                 440                 445
Lys Gly Glu Lys Glu Gln Arg Ile Leu Val Phe Asp Leu Gly Gly Gly
450                 455                 460
Thr Phe Asp Val Ser Leu Leu Glu Ile Gly Glu Gly Val Val Glu Val
465                 470                 475                 480
Arg Ala Thr Ser Gly Asp Asn His Leu Gly Gly Asp Asp Trp Asp Gln
                485                 490                 495
Arg Val Val Asp Trp Leu Val Asp Lys Phe Lys Gly Thr Ser Gly Ile
                500                 505                 510
Asp Leu Thr Lys Asp Lys Met Ala Met Gln Arg Leu Arg Glu Ala Ala
            515                 520                 525
Glu Lys Ala Lys Ile Glu Leu Ser Ser Ser Gln Ser Thr Ser Ile Asn
            530                 535                 540
Leu Pro Tyr Ile Thr Val Asp Ala Asp Lys Asn Pro Leu Phe Leu Asp
545                 550                 555                 560
Glu Gln Leu Thr Arg Ala Glu Phe Gln Arg Ile Thr Gln Asp Leu Leu
                565                 570                 575
Asp Arg Thr Arg Lys Pro Phe Gln Ser Val Ile Ala Asp Thr Gly Ile
                580                 585                 590
Ser Val Ser Glu Ile Asp His Val Val Leu Val Gly Gly Ser Thr Arg
            595                 600                 605
Met Pro Ala Val Thr Asp Leu Val Lys Glu Leu Thr Gly Gly Lys Glu
            610                 615                 620
Pro Asn Lys Gly Val Asn Pro Asp Glu Val Val Ala Val Gly Ala Ala
625                 630                 635                 640
Leu Gln Ala Gly Val Leu Lys Gly Glu Val Lys Asp Val Leu Leu Leu
                645                 650                 655
Asp Val Thr Pro Leu Ser Leu Gly Ile Glu Thr Lys Gly Gly Phe Met
                660                 665                 670
Thr Arg Leu Ile Glu Arg Asn Thr Thr Ile Pro Thr Lys Arg Ser Glu
            675                 680                 685
```

```
Thr Phe Thr Thr Ala Asp Asp Asn Gln Pro Ser Val Gln Ile Gln Val
        690                 695                 700

Tyr Gln Gly Glu Arg Glu Ile Ala Ala His Asn Lys Leu Leu Gly Ser
705                 710                 715                 720

Phe Glu Leu Thr Gly Ile Pro Pro Ala Pro Arg Gly Ile Pro Gln Ile
                725                 730                 735

Glu Val Thr Phe Asp Ile Asp Ala Asn Gly Ile Val His Val Thr Ala
            740                 745                 750

Lys Asp Lys Gly Thr Gly Lys Glu Asn Thr Ile Arg Ile Gln Glu Gly
        755                 760                 765

Ser Gly Leu Ser Lys Glu Asp Ile Asp Arg Met Ile Lys Asp Ala Glu
770                 775                 780

Ala His Ala Glu Glu Asp Arg Lys Arg Arg Glu Glu Ala Asp Val Arg
785                 790                 795                 800

Asn Gln Ala Glu Thr Leu Val Tyr Gln Thr Glu Lys Phe Val Lys Glu
                805                 810                 815

Gln Arg Glu Ala Glu Gly Gly Ser Lys Val Pro Glu Asp Thr Leu Asn
            820                 825                 830

Lys Val Asp Ala Val Ala Glu Ala Lys Ala Ala Leu Gly Gly Ser
        835                 840                 845

Asp Ile Ser Ala Ile Lys Ser Ala Met Glu Lys Leu Gly Gln Glu Ser
850                 855                 860

Gln Ala Leu Gly Gln Ala Ile Tyr Glu Ala Ala Gln Ala Ala Ser Gln
865                 870                 875                 880

Ala Thr Gly Ala Ala His Pro Gly Gly Glu Pro Gly Gly Ala His Pro
                885                 890                 895

Gly Ser Ala Asp Asp Val Val Asp Ala Glu Val Val Asp Gly Arg
            900                 905                 910

Glu Ala Lys
915

<210> SEQ ID NO 2
<211> LENGTH: 898
<212> TYPE: PRT
<213> ORGANISM: Artificial
<220> FEATURE:
<223> OTHER INFORMATION: fusion protein

<400> SEQUENCE: 2

Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Tyr Gly Met Asp Val
            100                 105                 110

Trp Gly Gln Gly Thr Thr Val Thr Val Ser Ser Gly Ile Leu Gly Ser
        115                 120                 125
```

```
Gly Gly Gly Gly Ser Gly Gly Gly Ser Gly Gly Gly Ser Gln
        130             135             140
Pro Val Leu Thr Gln Ser Ser Leu Ser Ala Ser Pro Gly Ala Ser
145                 150             155             160
Ala Ser Leu Thr Cys Thr Leu Arg Ser Gly Ile Asn Val Gly Pro Tyr
                165             170             175
Arg Ile Tyr Trp Tyr Gln Gln Lys Pro Gly Ser Pro Pro Gln Tyr Leu
            180             185             190
Leu Asn Tyr Lys Ser Asp Ser Asp Lys Gln Gln Gly Ser Val Pro
        195             200             205
Ser Arg Phe Ser Gly Ser Lys Asp Ala Ser Ala Asn Ala Gly Val Leu
210             215             220
Leu Ile Ser Gly Leu Arg Ser Glu Asp Glu Ala Asp Tyr Tyr Cys Met
225             230             235             240
Ile Trp His Ser Ser Ala Ala Val Phe Gly Gly Thr Gln Leu Thr
                245             250             255
Val Leu Gly Gly Gly Gly Ser Gly Gly Gly Ser Gly Gly Gly Gly
            260             265             270
Ser Met Ala Arg Ala Val Gly Ile Asp Leu Gly Thr Thr Asn Ser Val
        275             280             285
Val Ser Val Leu Glu Gly Gly Asp Pro Val Val Ala Asn Ser Glu
290             295             300
Gly Ser Arg Thr Thr Pro Ser Ile Val Ala Phe Ala Arg Asn Gly Glu
305             310             315             320
Val Leu Val Gly Gln Pro Ala Lys Asn Gln Ala Val Thr Asn Val Asp
                325             330             335
Arg Thr Val Arg Ser Val Lys Arg His Met Gly Ser Asp Trp Ser Ile
            340             345             350
Glu Ile Asp Gly Lys Lys Tyr Thr Ala Pro Glu Ile Ser Ala Arg Ile
            355             360             365
Leu Met Lys Leu Lys Arg Asp Ala Glu Ala Tyr Leu Gly Glu Asp Ile
370             375             380
Thr Asp Ala Val Ile Thr Thr Pro Ala Tyr Phe Asn Asp Ala Gln Arg
385             390             395             400
Gln Ala Thr Lys Asp Ala Gly Gln Ile Ala Gly Leu Asn Val Leu Arg
            405             410             415
Ile Val Asn Glu Pro Thr Ala Ala Ala Leu Ala Tyr Gly Leu Asp Lys
            420             425             430
Gly Glu Lys Glu Gln Arg Ile Leu Val Phe Asp Leu Gly Gly Thr
        435             440             445
Phe Asp Val Ser Leu Leu Glu Ile Gly Glu Gly Val Val Glu Val Arg
450             455             460
Ala Thr Ser Gly Asp Asn His Leu Gly Gly Asp Asp Trp Asp Gln Arg
465             470             475             480
Val Val Asp Trp Leu Val Asp Lys Phe Lys Gly Thr Ser Gly Ile Asp
            485             490             495
Leu Thr Lys Asp Lys Met Ala Met Gln Arg Leu Arg Glu Ala Ala Glu
        500             505             510
Lys Ala Lys Ile Glu Leu Ser Ser Gln Ser Thr Ser Ile Asn Leu
        515             520             525
Pro Tyr Ile Thr Val Asp Ala Asp Lys Asn Pro Leu Phe Leu Asp Glu
530             535             540
```

```
Gln Leu Thr Arg Ala Glu Phe Gln Arg Ile Thr Gln Asp Leu Leu Asp
545                 550                 555                 560

Arg Thr Arg Lys Pro Phe Gln Ser Val Ile Ala Asp Thr Gly Ile Ser
                565                 570                 575

Val Ser Glu Ile Asp His Val Val Leu Val Gly Gly Ser Thr Arg Met
            580                 585                 590

Pro Ala Val Thr Asp Leu Val Lys Glu Leu Thr Gly Gly Lys Glu Pro
        595                 600                 605

Asn Lys Gly Val Asn Pro Asp Glu Val Val Ala Val Gly Ala Ala Leu
    610                 615                 620

Gln Ala Gly Val Leu Lys Gly Glu Val Lys Asp Val Leu Leu Leu Asp
625                 630                 635                 640

Val Thr Pro Leu Ser Leu Gly Ile Glu Thr Lys Gly Gly Phe Met Thr
                645                 650                 655

Arg Leu Ile Glu Arg Asn Thr Thr Ile Pro Thr Lys Arg Ser Glu Thr
                660                 665                 670

Phe Thr Thr Ala Asp Asp Asn Gln Pro Ser Val Gln Ile Gln Val Tyr
            675                 680                 685

Gln Gly Glu Arg Glu Ile Ala Ala His Asn Lys Leu Leu Gly Ser Phe
        690                 695                 700

Glu Leu Thr Gly Ile Pro Pro Ala Pro Arg Gly Ile Pro Gln Ile Glu
705                 710                 715                 720

Val Thr Phe Asp Ile Asp Ala Asn Gly Ile Val His Val Thr Ala Lys
                725                 730                 735

Asp Lys Gly Thr Gly Lys Glu Asn Thr Ile Arg Ile Gln Glu Gly Ser
                740                 745                 750

Gly Leu Ser Lys Glu Asp Ile Asp Arg Met Ile Lys Asp Ala Glu Ala
            755                 760                 765

His Ala Glu Glu Asp Arg Lys Arg Arg Glu Ala Asp Val Arg Asn
        770                 775                 780

Gln Ala Glu Thr Leu Val Tyr Gln Thr Glu Lys Phe Val Lys Glu Gln
785                 790                 795                 800

Arg Glu Ala Glu Gly Gly Ser Lys Val Pro Glu Asp Thr Leu Asn Lys
                805                 810                 815

Val Asp Ala Ala Val Ala Glu Ala Lys Ala Ala Leu Gly Gly Ser Asp
                820                 825                 830

Ile Ser Ala Ile Lys Ser Ala Met Glu Lys Leu Gly Gln Glu Ser Gln
            835                 840                 845

Ala Leu Gly Gln Ala Ile Tyr Glu Ala Ala Gln Ala Ala Ser Gln Ala
        850                 855                 860

Thr Gly Ala Ala His Pro Gly Gly Glu Pro Gly Gly Ala His Pro Gly
865                 870                 875                 880

Ser Ala Asp Asp Val Val Asp Ala Glu Val Val Asp Asp Gly Arg Glu
                885                 890                 895

Ala Lys
```